US012806668B2

(12) United States Patent
Drori

(10) Patent No.: US 12,806,668 B2
(45) Date of Patent: Nov. 24, 2026

(54) SYSTEM AND METHOD FOR CLEANING WINE AND/OR A BARREL CONTAINING WINE

(71) Applicant: Ariel Scientific Innovations Ltd., Ariel (IL)

(72) Inventor: Elyashiv Drori, Shilo (IL)

(73) Assignee: Ariel Scientific Innovations Ltd., Ariel (IL)

( * ) Notice: Subject to any disclaimer, the term of this patent is extended or adjusted under 35 U.S.C. 154(b) by 72 days.

(21) Appl. No.: 18/278,021

(22) PCT Filed: Mar. 3, 2022

(86) PCT No.: PCT/IL2022/050237
§ 371 (c)(1),
(2) Date: Aug. 21, 2023

(87) PCT Pub. No.: WO2022/185314
PCT Pub. Date: Sep. 9, 2022

(65) Prior Publication Data

US 2024/0123476 A1 Apr. 18, 2024

Related U.S. Application Data

(60) Provisional application No. 63/155,838, filed on Mar. 3, 2021.

(51) Int. Cl.
*B08B 9/08* (2006.01)
*A61L 2/10* (2026.01)
(Continued)

(52) U.S. Cl.
CPC ................ *B08B 9/083* (2013.01); *B08B 9/08* (2013.01); *B08B 9/0804* (2013.01); *C12G 1/005* (2013.01);
(Continued)

(58) Field of Classification Search
CPC .................. B08B 9/08–46; E04H 4/16; E04H 4/1654–1672
See application file for complete search history.

(56) References Cited

U.S. PATENT DOCUMENTS

| | | | |
|---|---|---|---|
| 982,734 | A | 1/1911 | Martinelli |
| 5,130,030 | A | 7/1992 | Lloyd |

(Continued)

FOREIGN PATENT DOCUMENTS

| | | |
|---|---|---|
| CA | 1047417 | 1/1979 |
| CN | 101039880 | 9/2007 |

(Continued)

OTHER PUBLICATIONS

Expert Response and Search Report on Invention Patent Application Dated Oct. 17, 2024 From the National Institute of Industrial Property, INAPI, of Chile Re. Application No. 2023-02587 and its Translation of the Expert Report into English.( 20 Pages).

(Continued)

*Primary Examiner* — Kaj K Olsen
*Assistant Examiner* — Richard Z. Zhang

(57) ABSTRACT

There is disclosed a system and method for processing wine and/or a containing barrel, while keeping a volume of most of the wine in the barrel. The disclosed system and method can provide reduced mixing of different layers of wine in the barrel. An optional scrubbing mechanism cleans an interior surface of the barrel from encrusted matter, and an optional UV sterilization light source sanitizes an interior surface of the barrel that is alongside a cavity in the barrel empty of wine. In some embodiments a pumping and filtering system preserves non-mixing flow of wine in the barrel while effectively filtering wine optionally without the use of a filter cartridge or other interposing medium.

34 Claims, 35 Drawing Sheets

(51) Int. Cl.

| | |
|---|---|
| ***B08B 9/087*** | (2006.01) |
| ***C12G 1/00*** | (2019.01) |
| ***C12H 1/07*** | (2006.01) |
| *A61L 103/00* | (2026.01) |

(52) U.S. Cl.

CPC ................ *C12H 1/063* (2013.01); *A61L 2/10* (2013.01); *A61L 2103/23* (2026.01); *A61L 2202/11* (2013.01); *B08B 9/0808* (2013.01); *B08B 9/087* (2013.01); *B08B 2209/08* (2013.01); *C12G 1/00* (2013.01)

(56) References Cited

U.S. PATENT DOCUMENTS

| | | | | |
|---|---|---|---|---|
| 5,205,174 | A * | 4/1993 | Silverman | E04H 4/1654 376/310 |
| 2002/0133982 | A1* | 9/2002 | Price | E02F 5/28 37/307 |
| 2004/0076946 | A1 | 4/2004 | Trauner et al. | |
| 2007/0196535 | A1 | 8/2007 | Francia | |
| 2009/0056426 | A1 | 3/2009 | Kudlack | |
| 2010/0278980 | A1* | 11/2010 | Tomasello | B01F 23/2362 99/323.1 |
| 2013/0151061 | A1 | 6/2013 | Hong et al. | |
| 2013/0193089 | A1 | 8/2013 | Herberg et al. | |
| 2015/0086674 | A1 | 3/2015 | Gnekow | |
| 2017/0335263 | A1 | 11/2017 | Roussac | |
| 2018/0085798 | A1 | 3/2018 | Starr et al. | |
| 2018/0237732 | A1* | 8/2018 | Drori | C12H 1/165 |

FOREIGN PATENT DOCUMENTS

| | | | |
|---|---|---|---|
| CN | 107921488 | | 4/2018 |
| CN | 211195718 | U * | 8/2020 |
| CZ | 28750 | | 10/2015 |
| DE | 29501036 | | 4/1995 |
| DE | 102017011785 | | 6/2019 |
| FR | 2565597 | | 6/1984 |
| FR | 2712300 | | 5/1995 |
| FR | 2931837 | A1 * | 12/2009 |
| FR | 2968012 | | 6/2012 |
| JP | 06-77723 | | 10/1994 |
| JP | 2021-007924 | | 1/2021 |
| KR | 10-2013-0019286 | | 2/2013 |
| MX | 3758 | | 6/1981 |
| WO | WO 97/46660 | | 12/1997 |
| WO | WO 01/07178 | | 2/2001 |
| WO | WO 03/101636 | | 12/2003 |
| WO | WO 2005/039789 | | 5/2005 |
| WO | WO 2012/150541 | | 11/2012 |
| WO | WO 2016/087783 | | 6/2016 |
| WO | WO 2017/029675 | | 2/2017 |
| WO | WO 2022/185314 | | 9/2022 |

OTHER PUBLICATIONS

Supplementary European Search Report and the European Search Opinion Dated Dec. 13, 2024 From the European Patent Office Re. Application No. 22762740.3. (29 Pages).

Canton Cooperage "500L Puncheon", Canton Cooperage, XP093229417, 1 P., Jul. 31, 2019.

Informe de Busqueda y Parecer Dated Feb. 4, 2025 From the Instituto Nacional de Propiedad Industrial, Ministerio de Economia, Fomento y Turismo, INAPI, Gobierno de Chile Re. Application No. 202302587 and its Translation Into English. (19 Pages).

Applicant-Initiated Interview Summary Dated Aug. 1, 2019 From the US Patent and Trademark Office Re. U.S. Appl. No. 15/752,893. (3 pages).

Communication Pursuant to Article 94(3) EPC Dated Sep. 7, 2018 From the European Patent Office Re. Application No. 16836759.7. (6 Pages).

Communication Pursuant to Article 94(3) EPC Dated Feb. 11, 2019 From the European Patent Office Re. Application No. 16836759.7. (4 Pages).

Examination and Search Report Dated Jun. 14, 2019 From the Ministerio de Economia, Formento y Turismo, Gobierno de Chile Re. Application No. 201800323 and its Summary in English. (10 Pages).

Examination Report Dated Sep. 10, 2020 From the Australian Government, IP Australia Re. Application No. 2019200998. (4 Pages).

Examination Report Dated Dec. 19, 2019 From the Ministerio de Economia, Formento y Turismo, Gobierno de Chile Re. Application No. 201800323 and its Summary in English. (10 Pages).

Examination Report Dated Jul. 30, 2018 From the Australian Government, IP Australia Re. Application No. 2016308801. (10 Pages).

Examiner-Initiated Interview Summary Dated Jan. 24, 2020 From the US Patent and Trademark Office Re. U.S. Appl. No. 15/752,893. (3 pages).

International Preliminary Report on Patentability Dated Mar. 1, 2018 From the International Bureau of WIPO Re. Application No. PCT/IL2016/050910. (7 Pages).

International Preliminary Report on Patentability Dated Sep. 14, 2023 From the International Bureau of WIPO Re. Application No. PCT/IL2022/050237 (6 Pages).

International Search Report and the Written Opinion Dated Nov. 14, 2016 From the International Searching Authority Re. Application No. PCT/IL2016/050910. (9 Pages).

International Search Report and the Written Opinion Dated Jun. 20, 2022 From the International Searching Authority Re. Application No. PCT/IL2022/050237. (9 Pages).

Notice of Acceptance Dated Feb. 22, 2019 From the Australian Government, IP Australia Re. Application No. 2016308801. (4 Pages).

Notice Of Allowance Dated Mar. 5, 2020 From the US Patent and Trademark Office Re. Application No. 151752,893. (12 pages).

Notification of Office Action and Search Report Dated Nov. 3, 2020 From the State Intellectual Property Office of the People's Republic of China Re. Application No. 201680048110.2 and Its Translation of Office Action Into English. (21 Pages).

Notification of Office Action and Search Report Dated Apr. 25, 2021 From the State Intellectual Property Office of the People's Republic of China Re. Application No. 201680048110.2 and its Translation of Office Action Into English. (15 Pages).

Notification of Office Action Dated Mar. 17, 2020 From the State Intellectual Property Office of the People's Republic of China Re. Application No. 201680048110.2 and its Translation Into English. (7 Pages).

Officail Action Dated Apr. 21, 2021 From the Instituto Nacional De La Propiedad industrial Administracion Nacional De Patentes Inpi S República Argentina Re Application No. P200170100426 together with its Translation into English. (5 Pages).

Official Action Dated Jan. 2, 2019 From the US Patent and Trademark Office Re. U.S. Appl. No. 15/752,893. (22 pages).

Official Action Dated Oct. 2, 2019 From the US Patent and Trademark Office Re. Application No. 151752,893. (13 pages).

Official Action Dated Jun. 12, 2019 From the US Patent and Trademark Office Re. U.S. Appl. No. 15/752,893. (12 Pages).

Re-Examination Report Dated Nov. 3, 2020 From the Australian Government, IP Australia Re. Application No. 2016308801. (4 Pages).

Re-Examination Report Dated Mar. 6, 2020 From the Australian Government, IP Australia Re. Application No. 2016308801. (4 Pages).

Re-Examination Report Dated Aug. 10, 2020 From the Australian Government, IP Australia Re. Application No. 2016308801. (4 Pages).

Re-Examination Report Dated Mar. 11, 2021 From the Australian Government, IP Australia Re. Application No. 2016308801. (5 Pages).

Re-Examination Report Dated Dec. 12, 2019 From the Australian Government, IP Australia Re. Application No. 2016308801. (7 Pages).

(56) References Cited

OTHER PUBLICATIONS

Restriction Official Action Dated Sep. 6, 2018 From the US Patent and Trademark Office Re. U.S. Appl. No. 15/752,893. (7 pages).
Supplementary European Search Report Dated Jul. 12, 2018 From the European Patent Office Re. Application No. 16836759.7. (4 Pages).
Chen Shmuel Chemicals "Professional Electric Pump + Filter (Filter-Prize)", Chen Shmuel Chemicals, XP055396051, Equipments for Wine Making Domains, Wine Pump + Wine Filter, 2 P., Oct. 9, 2013. & English Translation.
Gamajet "A Better Way to Clean Barrels That Makes Other Cleaning Methods Obsolete", Gamajet Cleaning Systems, Inc., XP055396055, Portable Barrel Cleaning Equipment for Top-Down Cleaning Convenience, 2 P., Sep. 4, 2009.
OakAgingAndWine "Oak Aging and Wine", Retrieved from fed.us, 6 Pages, 2011.
Wine-4u "Filtering Equipment", Wine Cellars Equipment Catalog, XP055396060, 2 P., Aug. 4, 2014. & English Translation.
Notification of Office Action and Search Report Dated May 31, 2025 From the State Intellectual Property Office of the People's Republic of China Re. Application No. 202280030632.5 and its Summary and Machine Translation of Office Action into English. (25 Pages).
Decision on Rejection Dated Nov. 17, 2025 From the State Intellectual Property Office of the People's Republic of China Re. Application No. 202280030632.5 and its Machine Translation Into English. (20 Pages).
Notification of Office Action and Search Report Dated Sep. 22, 2025 From the State Intellectual Property Office of the People's Republic of China Re. Application No. 202280030632.5 with its Summary and Machine Translation into English. (23 Pages).
Communication Pursuant to Article 94(3) EPC Dated Feb. 11, 2026 From the European Patent Office Re. Application No. 22762740.3 (10 Pages).

* cited by examiner

SYSTEM AND METHOD FOR CLEANING WINE AND/OR A BARREL CONTAINING WINE

RELATED APPLICATIONS

This application is a National Phase of PCT Patent Application No. PCT/IL2022/050237 having International filing date of Mar. 3, 2022, which claims the benefit of priority under 35 USC § 119(e) of U.S. Provisional Patent Application No. 63/155,838 filed on 3 Mar. 3, 2021. The contents of the above applications are all incorporated by reference as if fully set forth herein in their entirety.

FIELD AND BACKGROUND OF THE INVENTION

The present invention, in some embodiments thereof, relates to treatment of liquids and containers and, more particularly, but not exclusively, to cleaning wine (racking) and cleaning a containing barrel.

Several times during the aging of wine in a barrel, clean wine is removed from the barrel and the remaining, sedimented wine, may also be removed and filtered or disposed of. Once empty, the barrel may be cleaned and then the clear wine may be returned to the clean barrel. This process may reduce the wine quality and/or may require significant manpower, extra barrels and/or other resources.

SUMMARY OF THE INVENTION

Following is a non-exclusive list including some examples of embodiments of the invention. The invention also includes embodiments which include fewer than all the features in an example and embodiments using features from multiple examples, also if not expressly listed below.

Example 1. A barrel cleaning system, comprising:

(a) an internal unit sized for insertion into an opening in a wine barrel and including an extraction cleaning head assembly and a return feed;

(b) an external unit;

(c) a first tube coupled to said internal unit and leading to said external unit and a second tube leading from said external unit to said return feed; and (d) at least one pump to drive the wine in said apparatus;

wherein said internal unit comprises a robot comprising a movement mechanism.

Example 2. The barrel cleaning system according to example 1, wherein said first tube and said second tube are flexible tubes.

Example 3. The barrel cleaning system according to example 1 or example 1, wherein said first tube and said second tube are telescopic tubes.

Example 4. The barrel cleaning system according to any one of examples 1-3, further comprising at least one turbidity sensor.

Example 5. The barrel cleaning system according to any one of examples 1-4, wherein said at least one turbidity sensor is located in said robot.

Example 6. The barrel cleaning system according to any one of examples 1-5, wherein said at least one turbidity sensor is located in first tube.

Example 7. The barrel cleaning system according to any one of examples 1-6, wherein said at least one turbidity sensor is located in said external unit.

Example 8. The barrel cleaning system according to any one of examples 1-7, wherein said movement mechanism comprises a plurality of wheels for moving said robot inside said barrel.

Example 9. The barrel cleaning system according to any one of examples 1-8, wherein said wheels are made of elastic material.

Example 10. The barrel cleaning system according to any one of examples 1-9, wherein said sized for insertion is sized for insertion in an opening having a diameter of about 45 mm.

Example 11. The barrel cleaning system according to any one of examples 1-10, further comprising circuitry for controlling said pump and said robot.

Example 12. The barrel cleaning system according to any one of examples 1-11, wherein said at least one turbidity sensor delivers turbidity information to said circuitry.

Example 13. The barrel cleaning system according to any one of examples 1-12, wherein at least two of said plurality of wheels each comprise a motor.

Example 14. The barrel cleaning system according to any one of examples 1-13, wherein said motors are activated by said circuitry.

Example 15. The barrel cleaning system according to any one of examples 1-14, wherein each of said motors are activated independently to each other.

Example 16. The barrel cleaning system according to any one of examples 1-15, wherein said plurality of wheels are configured to rotate forwards and backwards.

Example 17. The barrel cleaning system according to any one of examples 1-16, wherein said first tube and said second tube are connected to a top of said internal unit.

Example 18. The barrel cleaning system according to any one of examples 1-17, wherein said external unit comprises a filtration unit for separating wine from sediments.

Example 19. The barrel cleaning system according to any one of examples 1-18, wherein said first tube is connected to said filtration unit.

Example 20. The barrel cleaning system according to any one of examples 1-19, wherein said external unit comprises a collection tank for receiving filtered wine from said filtration unit.

Example 21. The barrel cleaning system according to any one of examples 1-20, wherein said second tube is connected to said collection tank.

Example 22. The barrel cleaning system according to any one of examples 1-21, further comprising a cable running from said external unit to said internal unit inside said first tube for providing electrical and electronic needs to said internal unit.

Example 23. The barrel cleaning system according to any one of examples 1-22, wherein said cable runs outside said first tube.

Example 24. The barrel cleaning system according to any one of examples 1-23, wherein said circuitry comprises instructions to activate said wheels of said internal unit to move said internal unit towards a second location comprising higher levels of turbidity as sensed by said at least one turbidity sensor in comparison with a first location comprising lower levels of turbidity.

Example 25. The barrel cleaning system according to any one of examples 1-24, further comprising a $SO_2$ sensor.

Example 26. The barrel cleaning system according to any one of examples 1-25, further comprising a $SO_2$ gas unit for adding $SO_2$ into wine as treatment.

Example 27. The barrel cleaning system according to any one of examples 1-26, further comprising UV radiation means.

Example 28. The barrel cleaning system according to any one of examples 1-28, wherein said external unit is configured to treat extracted wine by one or more of filtering, UV radiation and SO2 addition by means of said filtration unit, said UV radiation means and said SO2 gas unit.

Example 29. A method of cleaning a wine barrel, comprising:

a. inserting a robot in a barrel through an opening in said barrel and allowing said robot to reach a bottom of said barrel;

b. moving said robot, thereby cleaning said barrel by means of said robot.

Example 30. The method according to example 29, wherein said cleaning said barrel comprises activating a pump externally to said barrel, therefore extracting materials from said barrel.

Example 31. The method according to example 29 or example 30, further comprising filtering said extracted materials to separate wine from said extracted material.

Example 32. The method according to any one of examples 29-31, further comprising returning said separated wine to said barrel.

Example 33. The method according to any one of examples 29-32, further comprising activating a turbidity sensor to sense said extracted material.

Example 34. The method according to any one of examples 29-33, further comprising further moving said robot when a predetermined level of sensed turbidity of said sensed extracted material is reached.

Example 35. The method according any one of examples 29-34, further comprising treating the wine with UV.

Example 36. The method according any one of examples 29-35, further comprising measuring SO2 levels in said extracted wine before returning to said barrel.

Example 37. The method according any one of examples 29-36, further comprising adding SO2 into said extracted wine when said measuring provides a value below a predetermined value.

Example 38. A method of cleaning a wine barrel, comprising:

a. inserting a robot in a barrel through an opening in said barrel and allowing said robot to reach a bottom of said barrel;

b. activating a turbidity sensor comprising a predetermined turbidity level value;

when sensed turbidity levels are higher than said predetermined turbidity level value, then:

c. activating a pump therefore extracting sediments from said bottom of said barrel;

when sensed turbidity levels reach or are lower than said predetermined turbidity level value:

d. moving said robot to another location in said barrel where turbidity levels are higher than said predetermined turbidity level value;

e. repeating (b) through (d) until said bottom of said barrel is absent of said sediments or until said turbidity sensor cannot find another location where turbidity levels are higher than said predetermined turbidity level value.

Example 39. A barrel cleaning system, comprising (a) an internal unit sized for insertion into an opening in a wine barrel and including a sediment extraction opening, a return feed and (at least one turbidity sensor);

(b) a flexible tube having a first end coupled to said internal unit and a second end coupled to an external unit;

(c) an external unit comprising at least one pump;

(d) a circuitry for controlling said pump and said internal unit;

wherein said circuitry is configured to receive turbidity information from said at least one turbidity sensor and activate said at least one pump and said internal unit according to said received turbidity information.

Some embodiments of the present invention are described in general terms using the following additional examples. Other embodiments may utilize features from several examples and/or omit described features.

Additional Example 1. A method of treating wine in a barrel, comprising:

(a) extracting sediment from the wine while at least 80% by volume of the wine does not leave the barrel during any part of said treating; and (b) topping off the wine in the barrel.

Additional Example 2. A method according to example 1, wherein said topping off comprises filtering wine extracted with the sediment and returning said wine to the barrel.

Additional Example 3. A method according to example 1 or example 2, comprising removing encrustations from a bottom of said barrel as part of said treating.

Additional Example 4. A method according to example 3, comprising removing at least 50% by volume of the encrustations from the bottom of the barrel.

Additional Example 5. A method of treating wine in a barrel, comprising:

(a) extracting less than 50% of the wine from the barrel;

(b) treating said extracted wine; and (c) returning the treated wine into the barrel.

Additional Example 6. The method of example 5, comprising extracting not more than 20% of the wine from the barrel at any time during treating.

Additional Example 7. The method of example 5, comprising extracting not more than 3 liters of the wine from the barrel at any time during treating.

Additional Example 8. The method of example 5, comprising extracting a maximal cumulative amount of not more than 10% of the wine from the barrel.

Additional Example 9. The method of example 5, while said volume is at least 90% of the wine originally in the barrel.

Additional Example 10. The method of any of examples 5-9, wherein during (a)-(c) at least 95% of the volume of the barrel is filled with wine at any time during treating of said wine in a barrel.

Additional Example 11. The method of any of examples 5 to 10, wherein said extracting and said returning comprise extracting while maintaining a flow of wine at less than 30 cm/s inside the barrel.

Additional Example 12. The method of any of examples 5-11, wherein said extracting and said returning comprise maintaining a separate volume of returned wine in said barrel such that less than 20% of said wine in said volume is mixed with other wine in said barrel in a ratio of greater than 1:1.2.

Additional Example 13. The method of any of examples 5-11, wherein said extracting and said returning comprise maintaining a separate volume of returned wine in said barrel such that less than 20% of said wine in said volume has an NTU increased by more than 30% over when it was returned.

Additional Example 14. The method of any of examples 5-13, wherein said extracting and said returning comprise avoiding an increase in NTU of more than 5% in a layer of wine 5 cm above an extraction location.

Additional Example 15. The method of any of examples 5-11, wherein said extracting and said returning comprise maintaining a separate layer of returned wine in said barrel such that less than 20% of sediment in a bottom 10% of height of said barrel is dispersed during said treating.

Additional Example 16. The method of any of examples 5-15, wherein said treating comprises filtering.

Additional Example 17. The method of example 16, wherein said filtering comprises centrifugal filtering.

Additional Example 18. The method of any of examples 5-17, wherein said treating comprises addition of oxygen.

Additional Example 19. The method of any of examples 5-18, wherein said treating comprises irradiating.

Additional Example 20. The method of any of examples 5-19, comprising modifying a parameter of said method in response to a sensor reading on the wine.

Additional Example 21. The method of example 20, comprising extracting until a requisite attribute of the wine is met.

Additional Example 22. The method of example 20, wherein the wine attribute comprises turbidity.

Additional Example 23. The method of example 20, wherein flow rates of extraction and return are decreased with increases in measured turbidity of the wine and increased with decreases in measured turbidity of the wine.

Additional Example 24. The method of any of examples 5-23, comprising repeating (a)-(c) until a cumulative volume of at least 50% of said wine is extracted.

Additional Example 25. The method of any of examples 5-24, comprising repeating (a)-(c) until a cumulative volume of at most 150% of said wine is extracted.

Additional Example 26. The method of any of examples 5-25, comprising completing said treatment before a cumulative volume of at most 30% of said wine is extracted.

Additional Example 27. The method of any of examples 5-26, comprising completing said treatment once a lower sedimented layer having a thickness of less than 20% of a height of said wine in said barrel is treated.

Additional Example 28. The method of any of examples 5-27, comprising wasting less than 5% of said wine in said barrel during said method.

Additional Example 29. The method of any of examples 5 to 28, wherein said extracted wine is returned to an upper layer of the wine in the barrel.

Additional Example 30. The method of any of examples 5 to 29, wherein said extracted wine is returned to a position above an extraction position of the wine.

Additional Example 31. The method of any of examples 5-30, wherein at least 90% of said extraction during said treatment is at a distance of at most 3 cm above a bottom of said barrel.

Additional Example 32. The method of any of examples 5-31, wherein extraction comprises:

(a) positioning an opening of a snout at an extraction layer; and (b) suctioning wine through the snout.

Additional Example 33. The method of example 32, wherein said suctioning is by a pump.

Additional Example 34. The method of any of examples 5-33, comprising treating an interior upper surface of the barrel.

Additional Example 35. The method of example 34, wherein said treating comprises exposing said surface to ultraviolet radiation.

Additional Example 36. The method of any of examples 5-35, comprising opening said barrel to apply (a)-(c), and closing the barrel after applying (a)-(c) and avoiding mixing a top surface of said wine with other parts of said wine from said opening to said closing.

Additional Example 37. The method of example 32, comprising inserting said snout as part of an inner apparatus into said a barrel for said extracting.

Additional Example 38. The method of example 37, wherein said inserting is preceded by blanketing said wine with an inert gas.

Additional Example 39. The method of any of examples 37-38, wherein inserting comprises inserting from a top bung hole of said barrel, with a clearance of less than 10 cm above the barrel.

Additional Example 40. The method of any of examples 37-39, comprising automatically extracting at least an amount of the wine that the inner apparatus, when fully inserted, would cause overflow from the barrel.

Additional Example 41. The method of any of examples 37-40, comprising sensing immersion of at least a portion of said inner apparatus in said wine and initiating (a) only after said sensing.

Additional Example 42. The method of any of examples 37-41, comprising locking to and sealing said inner apparatus to a bung hole of said barrel.

Additional Example 43. The method of any of examples 5-42, comprising scrubbing material attached to an inside bottom of said barrel.

Additional Example 44. The method of example 43, comprising commencing said scrubbing after removing at least 80% of sediment in a bottom 10% of vertical height of the wine, from said barrel.

Additional Example 45. The method of example 43, wherein said treating comprises treating without lateral movement of a snout for wine removal and wherein said scrubbing includes lateral movement along the barrel bottom.

Additional Example 46. The method of example 43, comprising extracting wine including said scrubbed material before said material mixes with other wine in the barrel at a distance of more than 15 cm from a point of scrubbing to cause a change of more than 10% of an NTU of said other wine.

Additional Example 47. The method of example 43, comprising dimensionally reducing said scrubbed material before it leaves the wine barrel.

Additional Example 48. A method for scrubbing encrusted matter off of an interior surface of a barrel that is mostly filled with wine, comprising:

(a) scrubbing off encrusted matter from the interior surface using a scrubbing element;

(b) extracting wine including said material;

(c) filtering said removed wine; and (d) returning said filtered wine into said barrel, thereby maintaining at least 90% of an original volume of wine of said barrel, in said barrel, at all times during a complete process of scrubbing.

Example 49. A wine filtering apparatus, comprising:

(a) an input which receives an inflow of wine;

(b) a filter which filters said received wine;

(c) an output from which said wine leaves the apparatus;

(d) at least one wine reservoir; and (e) at least one pump to drive the wine in said apparatus, wherein a total reservoir volume in said apparatus is less than 20 liters.

Additional Example 50. Apparatus according to example 49, wherein one or more of said reservoirs contains a level sensor.

Additional Example 51. Apparatus according to examples 49 or 50, wherein one of the pumps draws wine from one of the reservoirs at a flow rate higher than a flow rate of inflowing wine to the reservoir.

Additional Example 52. Apparatus according to any of examples 49-51, wherein one of the pumps deposits wine into one of the reservoirs at a flow rate less than a flow rate outflowing wine from the reservoir.

Additional Example 53. Apparatus according to any of examples 49 to 50, wherein the filter comprises a centrifugal filter pump comprises the filter and one of said pumps.

Additional Example 54. Apparatus according to any one of examples 49 to 53, wherein said input is pumped from a barrel containing wine, and said output is pumped to the barrel.

Additional Example 55. Apparatus according to example 49 and external pumps connected to the input and output.

Additional Example 56. Apparatus according to any of examples 49-55, having an empty weight of less than 62 kg.

Additional Example 57. Apparatus according to any of examples 49-56, having a horizontal width of less than 85 cm.

Additional Example 58. A wine filtering system, comprising:

(a) an inner apparatus sized for insertion in to a wine barrel bung hole and including an extraction snout and a return feed;

(b) an outer apparatus including a tube coupled to said snout and leading to a filter and a tube leading from said filter to said return feed; and (c) at least one pump to drive the wine in said apparatus.

Additional Example 59. A system according to example 58, comprising circuitry for controlling said pump and wherein said circuitry and a geometry of said snout and return feed are configured to reduce mixing of extracted wine and returned wine in said barrel.

Additional Example 60. A system according to example 58 or example 59, wherein at least parts of said inner apparatus in contact with wine are detachable from other parts of the inner apparatus and disposable.

Additional Example 61. A system according to any of examples 58-60, wherein said snout is configured to both remove wine and scrub a barrel bottom.

Additional Example 62. A system according to any of examples 58-61, wherein said snout is collapsible to a maximum lateral extent smaller than a diameter of said bung hole from a maximum lateral extent larger than said bung hole diameter.

Additional Example 63. A system according to any of examples 58-62, wherein said snout is mounted on swinging element.

Additional Example 64. A system according to example 63, comprising at least one motor that moves said snout laterally.

Additional Example 65. A system according to any of examples 58-64, wherein said snout is mounted on a self-lengthening telescoping element having a resting length of at least a diameter of a wine barrel.

Additional Example 66. A system according to example 65, comprising a flexible wine extraction tube mounted externally to said element.

Additional Example 67. A system according to any of examples 58-66, comprising a bung-hole lock to which said inner apparatus is mechanically coupled.

Additional Example 68. A system according to any of examples 58-66, having a fluid capacity of less than 16 liters.

Additional Example 69. A method of inserting an apparatus into a wine barrel, comprising:

(a) starting inserting the apparatus into a wine barrel;

(b) detecting a level of wine indicating that the level would increase above a desired threshold due to said insertion;

(c) automatically extracting wine in an amount sufficient to avoid passing said threshold; and (d) completing said insertion.

Additional Example 70. A wine treatment system, comprising:

(a) a wine extraction and treatment subsystem having at least one settable parameter; and (b) circuitry for controlling said parameter.

Additional Example 71. A system according to example 70, comprising a UI for receiving a user input regarding the wine to be treated.

Additional Example 72. A system according to example 70 or example 71 having a memory storing therein at least one parameter or desired attribute or treatment parameter of said wine.

Additional Example 73. A system according to example 58, wherein said snout comprises a rotatable scrubber powered by at least one of a motor, a flexible rotating cable and flow of liquid suctioned through a turbine.

Additional Example 74. A system according to example 58, wherein said snout is mounted on a curved rod.

Additional Example 75. A system according to example 74, wherein, the peak (vertex) of the curve is distanced between 5-15 cm from a base line connecting the ends of the rod.

Additional Example 76. A system according to example 74, wherein said rod is curved along at least two planes.

Additional Example 77. A system according to example 58, wherein said inner apparatus further includes at least one sensor.

Additional Example 78. A system according to example 77, wherein said sensor is at least one of a turbidity sensor and a liquid contact sensor.

Additional Example 79. A system according to example 58, wherein said outer apparatus includes at least one inner-apparatus-driving assembly sized to fit between respective layers of wine barrels.

Additional Example 80. A system according to example 79, wherein said driving assembly is placed on a barrel and aligned with said bung hole.

Additional Example 81. A system according to example 79, wherein said system further comprises at least one harness connecting said outer apparatus and said inner apparatus and including at least one of a liquid removal tube, an electric power cable, a data input/output cable and a flexible rotatable driver cable.

Additional Example 82. A system according to example 79, wherein said inner-apparatus-driving assembly moves said rod in two planes concurrently.

Additional Example 83. A system according to example 58, wherein said inner apparatus includes a cleaning head swing drive assembly.

Additional Example 84. A system according to example 70, wherein said inner-apparatus-driving assembly includes at least one cog rotatingly aligned with said bung hole and a linear actuator and wherein said cog rotates said linear actuator.

Additional Example 85. A system according to example 73, wherein said scrubber further includes at least one caster.

Additional Example 86. A system according to example 58, further comprising a bung-hole lock to which said inner apparatus is mechanically coupled.

Additional Example 87. A system according to example 58, wherein said filter comprises a centrifugal filter pump.

Additional Example 88. A system according to example 58, further comprising at least one reservoir with a total reservoir volume less than 20 liters.

Additional Example 89. A system according to example 58, having a fluid capacity of less than 16 liters.

Additional Example 90. A system according to example 58, wherein said cleaning head includes a scrubber rotatable along a plane parallel to the direction of flow of extracted liquid.

Additional Example 91. A system according to example 58, wherein said cleaning head includes a scrubber rotatable along a plane normal to the direction of flow of the extracted liquid.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

As will be appreciated by one skilled in the art, some embodiments of the present invention may be embodied as a system, method or computer program product. Accordingly, some embodiments of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, some embodiments of the present invention may take the form of a computer program product embodied in one or more computer readable medium(s) having computer readable program code embodied thereon. Implementation of the method and/or system of some embodiments of the invention can involve performing and/or completing selected tasks manually, automatically, or a combination thereof. Moreover, according to actual instrumentation and equipment of some embodiments of the method and/or system of the invention, several selected tasks could be implemented by hardware, by software or by firmware and/or by a combination thereof, e.g., using an operating system.

For example, hardware for performing selected tasks according to some embodiments of the invention could be implemented as a chip or a circuit. As software, selected tasks according to some embodiments of the invention could be implemented as a plurality of software instructions being executed by a computer using any suitable operating system. In an exemplary embodiment of the invention, one or more tasks according to some exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

Any combination of one or more computer readable medium(s) may be utilized for some embodiments of the invention. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium and/or data used thereby may be transmitted using any appropriate medium, including but not limited to wireless, wireline, optical fiber cable, RF, etc., or any suitable combination of the foregoing.

Computer program code for carrying out operations for some embodiments of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Some embodiments of the present invention may be described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Some of the methods described herein are generally designed only for use by a computer, and may not be feasible or practical for performing purely manually, by a human expert. A human expert who wanted to manually perform similar tasks, such as pump control, sensor analysis and/or database retrieval, might be expected to use completely different methods, e.g., making use of expert knowledge and/or the pattern recognition capabilities of the human brain, which would be vastly more efficient than manually going through the steps of the methods described herein.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

Figure 1:
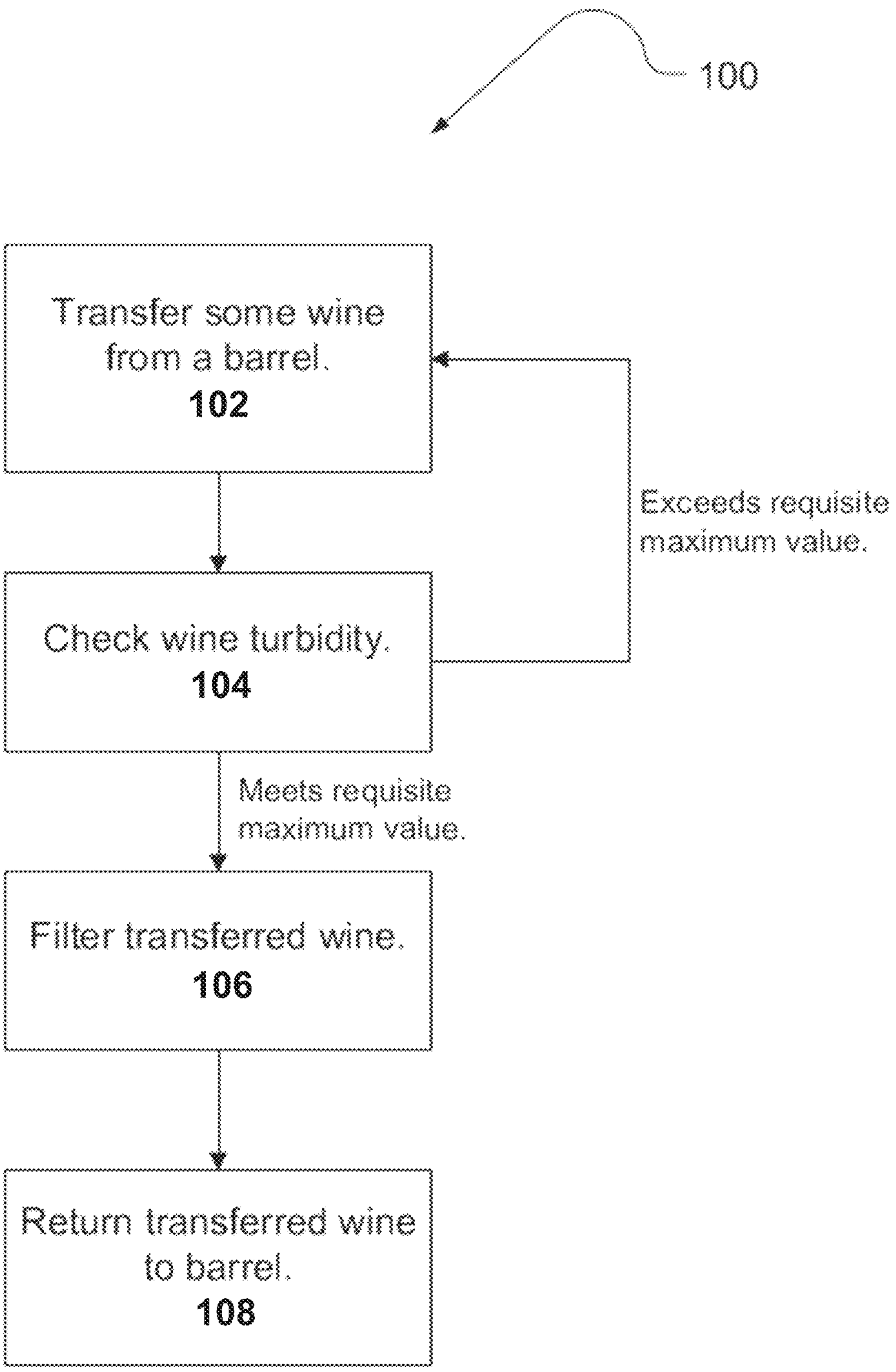
FIG. 1 is a flow chart of an exemplary method for cleaning wine in a barrel while transferring a minority of the wine from the barrel according to some embodiments of the invention.

The present invention, in some embodiments thereof, relates to treatment of liquids and containers and, more particularly, but not exclusively, to cleaning wine (racking) and cleaning a containing barrel.

Overview

A broad aspect of some embodiments of the invention relates to treating wine in a barrel by removing solids (possibly with some wine), rather than by removing clean wine. In some exemplary embodiments of the invention, this allows only a small fraction of the wine to be removed and/or otherwise agitated during cleaning.

A broad aspect of some embodiments of the invention relates to controlling wine quality by removing sediment and/or encrustations from a barrel. Optionally, the sediments and/or encrustations are removed in a manner which affects a further aging of the wine. Optionally or alternatively, encrustation removal exposes parts of a wine barrel to the wine.

An aspect of some embodiments of the invention relates to a robot for cleaning sediments from the inside of a wine barrel. In some embodiments, the robot is small enough to fit in an opening of a wine barrel. In some embodiments, the opening is from about 30 mm to about 50 mm, optionally from about 25 mm to about 60 mm, optionally from about 20 mm to about 100 mm, for example, 25 mm, 30 mm, 35 mm, 40 mm or 45 mm. In some embodiments, the robot pumps out the sediments with some wine while traveling the bottom of the wine barrel. In some embodiments, the robot travels according to levels of turbidity sensed by the robot. In some embodiments, clean wine is returned to the wine barrel after it has been treated, for example by filtration and/or exposure to UV and/or exposure to inert gases, and measured for turbidity.

An aspect of some embodiments relates to a system for cleaning a wine barrel from its sediments, when it is in place, without emptying the wine and with minimal loss of wine and prevention of damage of the wine's aging characteristics.

An aspect of some embodiments of the invention relates to a method of processing wine and/or a barrel, which can be aging wine, in a barrel, while transferring only a fraction of the wine from the barrel to another container. In some exemplary embodiments of the invention, transferred wine is filtered and filtered wine is returned to the barrel. Hereinafter, the method is referred to as "in-place wine cleaning".

In some embodiments, a volume of the wine transferred is not more than 50%, 40%, 30%, 20%, 10% or 5% or smaller or intermediate percentages. Potential advantages of transferring most of the wine may include one or more of: reduction in labor costs; reduction in wine damage due to oxidation and/or mixing; and reduction of wine loss entailed in transferring wine between containers. In some exemplary embodiments of the invention, less than 20% of the wine in total and/or less than 5% of wine from an upper 20% of the barrel (by volume), are transferred.

In some exemplary embodiments of the invention, low mixing is evidenced by avoiding increasing an NTU (Nephelometric Turbidity Units) of a wine volume near a wine extraction location by more than a threshold amount. For example, wine at 5 cm (or 3 cm, 10 cm or 15 cm or intermediate distances) vertically of the extraction location optionally increase in less than 30%, 20%, 10 5%, 3% or intermediate percentages of NTU.

In some embodiments, wine is extracted and transferred from a bottom, sediment-laden layer of wine in the barrel, for example, as discussed in further detail in this application. A potential advantage of extracting wine from a bottom, sediment-layer is preferentially expressing the most turbid wine in the barrel for cleaning.

Additionally, there is a potential advantage of non-mixing of sediment with wine at higher layers, for example, as discussed in further detail in this application.

In some exemplary embodiments of the invention, the bottom of the barrel includes some components that are vertically elevated relative to others. Optionally, the bottom of the barrel comprises all the surfaces that are vertically lower than the two ends of the barrel, when the barrel lies on its side.

In some exemplary embodiments of the invention, the wine is removed at a speed (e.g., slow enough) which allows other sediment to migrate towards a wine removal element, while optionally not requiring too much wine removal.

In some exemplary embodiments of the invention, wine is returned to the barrel away from the sediment carrying layer and/or below a top layer of the wine, and/or otherwise returned in a manner which prevents mixing of wine with wine from one or both of those layers.

In some exemplary embodiments of the invention, wine is removed and/or returned at a low enough speed so as to prevent or reduce unwanted mixing.

Optionally, the filtering system uses an input buffer and/or an output buffer, to allow the filter (e.g., a centrifugal filter) to operate at a higher flow rate than allowed for wine extraction and/or return.

Optionally, transfer concludes when turbidity at or near the sediment-laden layer meets a requisite maximum value; turbidity sensors are discussed in further detail in this application. A potential advantage of transferring wine until wine turbidity meets a maximum value is an assurance of wine clarity, while optionally avoiding over-removal of wine.

In some exemplary embodiments of the invention, the wine treating system includes a portion inserted into the barrel. Optionally, the in-barrel portion is spring-loaded towards the bottom of the barrel and includes a sediment removal element that travels along a bottom of the barrel. Optionally, the in-barrel portion is configured to remove wine from the barrel during insertion thereof, if there is a risk of wine overflow.

In some exemplary embodiments of the invention, wine quality is maintained by injecting Argon (or other non-oxidizing gas) into the barrel to take the place of removed wine and/or to provide a blanket protecting the wine from contact with the atmosphere. Optionally or alternatively, the in-barrel portion includes a position lock and/or air seal where it is inserted into a bung-hole of the barrel.

In some exemplary embodiments of the invention, an upper cavity between the wine and the barrel is sterilized by the in-barrel system, for example, using UV light.

While in some embodiments wine removal is (only) from or near the bottom (e.g., spaced from the bottom of the barrel by between 0.2 and 3 cm, in an exemplary embodiment of the invention, an in-place wine cleaning system extracts wine in a barrel for cleaning at one or more layers other than at a barrel bottom. Optionally, extraction is at one or more layers that often form during wine aging. For example, the system extracts wine at a layer near the floor of the barrel, which often contains an elevated concentration of sediment. Additionally, for example, the system extracts wine from a layer near a top surface of the wine, which often contains an elevated concentration of aerobic microorganisms and/or floating particles. Additionally, for example, the system extracts wine from a layer anywhere throughout the wine, where suspended particles are often dispersed. Optionally, the system extracts wine for cleaning at one or more layers in sequence. For example, an opening of a snout is positioned at one or more layers in sequence. Optionally, a control unit of the system selects each layer. Optionally, a telescoping member positions the snout.

In some embodiments, a cycle of transfer, filtering, and return is repeated one or more times at a layer. Optionally, the cycle is repeated until turbidity of wine in the barrel meets a requisite maximum value; for example, for young wine with an especially large quantity of sediment. A potential advantage of repeating the cycle until wine turbidity meets a maximum value is an assurance of wine clarity. It is noted that in some embodiments the extraction and return is continuous, optionally punctuated by stops. In other embodiments, extraction, filtering and return is perfume din steps, optionally each one manually initiated by a user.

As will be described herein, the wine can be processed other than or in addition to filtering, for example, sterilization and/or adding of materials thereto, such as gases and/or materials which affect suspension and/or sediment formation. Also, while the description uses wine and wine barrels as its main embodiments, it may also be applied to other fermenting beverages, such as sake, soy sauce, beer, cider, mead, liquor and perry and/or to aging alcoholic beverages, such as brandy and whiskey.

In an exemplary embodiment of the invention, an in-place wine cleaning system includes one or more sensors, for example, a turbidity sensor disposed in wine in a barrel. Optionally, one or more turbidity sensors(s) monitor the cleanliness of the wine. Optionally, after sensor readings indicate that turbidity of the wine is at or below a requisite maximum, wine extraction concludes; and/or, for example, in an iterative embodiment, iterations end; and/or, for example, in a multi-layer cleaning embodiment, the method ends at that layer and moves to a next layer. Optionally, turbidity sensor reading(s) are used to determine a degree of mixing of wine layers, for the purpose of controlling flow rates of wine extraction and/or return, as discussed in further detail in this application.

In some exemplary embodiments of the invention, turbidity measurements are used to estimate an allowed flow rate (e.g., higher rate allowed if low turbidity, as less contamination caused by turbulence).

In some exemplary embodiments of the invention, turbidity measurements are used to control filtering, for example, slower and/or otherwise more effective filtering being applied if the wine is more turbid.

In some exemplary embodiments of the invention, an in-place wine cleaning system controls flows of wine in a barrel. Optionally, the control of wine flows reduces the mixing between a bottom layer of wine and higher layers of wine. For example, the system reduces mixing between wine in a bottom sediment-laden layer with wine in higher layers containing low levels of sediment. Non-mixing of a bottom layer with higher layers of wine potentially enables effective and quick in-place wine cleaning; for example, efficiently extracting wine from a sediment-laden bottom layer with reduced mixing of sediment with higher, cleaner layers and with reduced amounts of wine from a higher layer mixed in and extracted. In-place wine cleaning to a turbidity of 10 NTU (and/or other desired amount) in less than, for example, 20, 15, 10 or 5 minutes is thereby potentially achieved. Other degrees of cleaning may be used instead, for example, reduction of 10, 20, 30, 40 or intermediate or smaller number of units and/or other turbidity targets, such as 5, 15, 22, 33, 50, 70, 93 and/or intermediate or smaller or larger targets. An addition potential advantage is prevention of bacteria and/or chemicals from sediment at a bottom layer from interacting with others parts of the wine.

Optionally, the control of wine flows reduces mixing between a top layer near a bung hole and lower layers of wine. A potential advantage of reducing or avoiding mixing between a top layer and lower layers is to prevent mixing that encourages migration of bacteria from a top layer to lower levels of the wine.

In an exemplary embodiment of the invention, mixing of layers caused by extraction and return flows of wine is reduced. Optionally, to reduce mixing of layers the system reduces flow velocities, presence of eddy currents, drag, and/or other agents of mixing.

In some embodiments, flow rate of extraction and/or return of wine in an in-place wine cleaning method are adjusted in a closed loop in response to the degree of mixing. Optionally, the degree of mixing is evaluated according to a turbidity value of wine. For example, an elevated turbidity value at a wine layer above a sedimentary layer may indicate mixing of sediment with the upper wine layer, so a flow rate of extraction is lowered in order to reduce mixing. Optionally, turbidity is measured and compared at different layers of wine, in order to evaluate the degree of mixing and adjust the flow rate of wine extraction and/or return accordingly. For example, turbidity is measured in or near a bottom sediment-laden layer and in a higher, cleaner layer. Optionally, if the two turbidity values start to converge, possibly indicating increased mixing of layers, flow rate(s) are accordingly reduced.

In some exemplary embodiments of the invention, the snout is used to remove material encrusted on the bottom of the barrel and such material is optionally immediately extracted for filtering and preventing contamination of wine. Optionally, a same snout is used for extracting and for scrubbing. Optionally, a separate scrubber is provided. Optionally, the scrubber is disposed inside the snout.

In some exemplary embodiments of the invention, the snout and mechanism, e.g., cleaning head assembly is attached to is flexible enough and/or resilient, so it can be constricted and inserted through a small clearance (e.g., less than 10, less than 5 and/or less than 3 cm) above a barrel and/or through an existing orifice of the barrel such as a bung hole with a diameter of, for example, 50 mm.

In some exemplary embodiments, before insertion of an inner apparatus of a wine cleaning system into wine in a barrel, an air cavity in the barrel above the wine is purged with a slow flow of an inert gas such as Argon, or a layer of non-oxidizing gas (e.g., heavier than air and/or colder than air) is deposited above the wine. A potential advantage is preventing oxidation of the top surface layer of wine and of the first amount of wine extracted. In some embodiments, an oxygenating gas such as air flows out of the snout. Optionally, the oxygenating gas is filtered air. Optionally, the oxygenating gas flows out of the snout when the snout is at a specific layer of wine, such as a middle layer. Optionally, an oxygen sensor monitors the oxygen level in a closed-loop control of the flow of oxygenating gas. Optionally, the system oxygenates the wine after (or during) the cleaning process is completed, for example, by providing gas flow through the snout into a bottom layer of the wine and/or via mixing in the filtering system.

In an exemplary embodiment of the invention, an in-place wine cleaning system, upon immersion of an extracting apparatus of the system into wine in a barrel, extracts enough wine to prevent overflow of wine displaced by the inner apparatus. A potential advantage is reducing loss of wine. Optionally, the system extracts only while the inner apparatus is adequately immersed, for example, when a snout opening is fully immersed. Extracting only when the snout opening is fully immersed potentially prevents air from entering and oxidizing wine. Additionally, extracting only when the opening is fully immersed potentially prevents splattering and loss of wine apt to occur with a partially immersed opening. Optionally, a liquid contact sensor of the inner apparatus detects and reports whether or not the extraction apparatus is adequately immersed. Optionally, during a wine cleaning method, extraction of wine in the barrel stops when the liquid contact sensor reports non-contact with wine. Optionally, after stopping of extraction due to a report of non-contact by the liquid contact sensor, cleaning of wine extracted from wine in the barrel continues.

Optionally, the amount of initial wine removal is selected to maintain a level of wine within, for example, 10 cm, 5 cm, 3 cm from the bung hole.

In some embodiments, an annular lock mechanism secures the inner apparatus. Optionally, the lock mechanism is used as a cannel for the inner apparatus and/or to serve as a base against which the inner mechanism is pressed down towards the barrel bottom. Optionally or alternatively, the lock mechanism is used to provide an air lock and/or gas insertion. In some exemplary embodiments of the invention, the lock mechanism contacts an inner surface of a bung hole of the barrel and seals the bung hole. Optionally, a silicone layer between the inner apparatus and the lock mechanism seals the lock mechanism opening. An potential advantage of sealing the lock mechanism at the bung hole and inner apparatus interfaces is prevention of oxygen from entering the barrel and an ensuing oxidation damage to the wine.

An aspect of some embodiments of the invention relates to a wine filtering system containing one or more reservoirs that buffer unequal flow rates across the system. A potential advantage of buffer reservoirs is allowing flows from various pumps to operate independently at different flow rates selected to optimize their own performance or system performance, thereby enabling an in-place, low-mixing wine cleaning system. For example, an extraction pump and a return pump are optimized at the highest flow rate consistent with low mixing, while a filter pump operates at its designed flow rate, which may be significantly higher than the extraction and/or the return. Optionally, the reservoirs contain level sensors. Optionally, a control unit schedules operation of the pumps (and/or the filtering operation) in a closed loop, for example, based on such sensor readings.

In some exemplary embodiments of the invention, one or more energy sources, disposed inside a barrel containing wine, treat an interior surface of the barrel. Optionally, energy from an energy source is incident on a region of the interior surface that is alongside an empty cavity in the barrel. In one example, a UV sterilization light source inside the barrel is used to sanitize barrel surfaces surrounding a cavity above the wine level. Optionally, an energy source is disposed inside a cavity when in use. Optionally, the energy source is deactivated at other times. In some exemplary embodiments of the invention, the source is aimed to irradiate the walls of the barrel and/or the area near the bung hole. Optionally or alternatively, the upper surface of the wine is irradiated.

An aspect of some embodiments of the invention relates to a barrel cleaning system for cleaning encrusted matter off the inside surface of a wine barrel while the barrel contains wine, for example, clearing 10%, 20%, 30%, 50%, 60% or intermediate or greater percentages of the bottom of the barrel and/or of the volume of encrustations. It is noted that encrustation often comprises a significant component of inorganic materials, such as salts, and suspended sediment often comprises a significant component of organic debris. In some exemplary embodiments, the barrel cleaning system is integrated together with an in-place wine cleaning system. For example, a scrubber of the barrel cleaning system is disposed inside a snout of an in-place wine cleaning system, for example, as described in further detail in the application.

In some exemplary embodiments of the invention, scrubbing is combined with and coordinated with wine extraction so that wine containing the debris caused by scrubbing is extracted before it can mix with other wine in the barrel. Optionally, a chopper is used to reduce the size of scrubbed debris.

In some exemplary embodiments of the invention, the scrubber moves, for example, to cover the entire bottom of the barrel, optionally use an automated mechanism.

Optionally, the scrubber is disposed inside a snout of an in-place wine cleaning system. A potential advantage of the scrubber inside the snout of an in-place wine cleaning system is that one apparatus performs both in-place wine cleaning and barrel cleaning and/or serves to extracted encrusted material from the barrel.

Optionally, movement is by a pendulum mechanism which swings the scrubber. Optionally, the scrubber is mounted on an elastically telescoping rod, which ensures contact with a bottom surface and/or conforms to changes in distance between the bung hole and the barrel bottom. In some embodiments, a similar movement mechanism is used during sediment removal. Alternatively, sediment removal has no or less movement.

In some exemplary embodiments of the invention, the scrubber spaces a bottom of the snout from the barrel bottom, to allow sedimented wine ingress.

Optionally, the scrubber is in the form of a spiral brush. Optionally, a motor spins the spiral brush during scrubbing. Optionally, flow of extracted wine through a turbine spins the spiral brush during scrubbing.

In some exemplary embodiments of the invention, the brush includes one or more scrapers or bristles which is softer than wood, so as not to damage wood panels of the barrel. In some embodiments, the brush spins along a plane parallel to the direction of flow of the extracted wine. In some embodiments, the brush spins along a plane normal to the direction of flow of the extracted wine.

In an exemplary embodiment of the invention, a gear mechanism is provided for converting single-directional rotation to bi-directional swinging of a pendulum rod supporting a scrubber. Optionally, a motor drives an originating gear in one direction of rotation. The originating gear is toothed along an arc of the originating gear.

Optionally, the toothed arc alternately engages and rotates two pinion gears.

Optionally, rotation of a first of the two pinion gears causes extension rod to swing upwards. Optionally, upon disengagement of toothed arc from a first of two pinion gears, the extension rod is free to swing downwards. Optionally, a rotation speed of a swing-drive motor is timed so that when the toothed arc reaches a second of two pinion gears, the extension rod has freely swung back down to substantially its vertically extended position. Optionally, engagement of second of two pinion gears by the toothed arc causes the same sequence of movements of the extension rod, in the opposite direction of swinging.

In some embodiments of the invention, an aging wine barrel cleaning system comprises a wine cleaning system and/or a barrel cleaning apparatus.

Optionally, the wine cleaning system cleans wine in a barrel while the barrel contains a volume of the wine comprising most of the wine. Optionally, during wine cleaning, a maximum of 10% of wine is outside the barrel. Optionally, during wine cleaning, the barrel is 90-100% full, for example, about 95% full.

Optionally, barrel cleaning methods include UV sterilization of an interior surface adjacent to an unfilled cavity in the barrel and/or scrubbing and removing encrusted matter from an encrusted interior surface.

Optionally, an inner apparatus is installable with a clearance of only 20 cm or 10 cm or less above the barrel. Optionally, the inner apparatus contains a snout for wine cleaning, UV sterilization light source(s), a scrubbing element for barrel cleaning, and a movement mechanism for scanning the barrel bottom.

Optionally, the aging wine barrel cleaning system contains an extraction pump, a filtering system, a return pump, and a control unit. Optionally, the filtering system comprises an input reservoir, a filter pump, and an output reservoir, and/or interconnecting tubing. Optionally, the input pump, output pump, and/or filtering system are inside the barrel during wine cleaning. Alternatively, one or more of these are disposed in an outer apparatus, external to the barrel. Optionally, the outer apparatus weighs no more than 35 kg, potentially allowing the outer apparatus to be transportable on a cart that is moved by one person without automotive power assistance. Optionally, any such reservoir has a volume of less than 100, 50, 20, 10 liters or intermediate volumes.

Optionally, the system is transportable with only 80 cm of clearance between rows.

An aspect of some embodiments of the invention relates to an in-barrel-portion driver assembly. In some embodiments, the driver assembly is placed on a barrel. In some embodiments, the driver assembly is placed on an outer system portion. In some embodiments, the driver assembly is a low profile driver assembly. In some embodiments, the driver assembly is coupled to an in-barrel-portion prior to insertion of the in-barrel-portion into the barrel.

An aspect of some embodiments of the invention relates to an in-barrel-portion that includes a curved rod. In some embodiments, the peak (vertex) of the curve is distanced between 5-15 cm, 6-10 cm, 7-8 cm or any distance in between, from a straight line connecting the ends of the rod. In some embodiments, the rod is curved along at least two planes. In some embodiments, the coupling between the rod and the driver assembly allows insertion of the rod into the bung hole while connected to the drive assembly.

An aspect of some embodiments of the invention relates to powering the outer system portion and/or inner system portion with pneumatic and/or hydraulic pressure. In some embodiments of the invention one or more system pumps are powered by pneumatic and/or hydraulic pressure. In some embodiments of the invention the in-barrel-portion driver assembly is powered by pneumatic and/or hydraulic pressure. In some embodiments of the invention the in-barrel-portion cleaning head is powered by pneumatic and/or hydraulic pressure. In some embodiments of the invention the system includes a gearbox instead of or in addition to the in-barrel-portion driver assembly, powered by pneumatic and/or hydraulic pressure.

An aspect of some embodiments of the invention relates to a harness that connects the outer system portion to the in-barrel-portion. In some embodiments, the harness includes at least a flexible rotatable driver cable. In some embodiments, the harness includes at least one of a liquid withdrawal conduit, a power cable, a data input/output cable, hydraulic and/or pneumatic hose and a flexible rotatable driver cable.

In some exemplary embodiments of the invention, the system includes circuitry to automate its operation. For example, one or more or all of the following may be automated: during insertion, gas injection may proceed automatically as the inner mechanism or in-barrel portion is inserted and then wine extraction provided to ensure that no wine overflow, thereafter, detection of contact of the snout against the barrel bottom is optionally detected (e.g., using a contact sensor). Optionally, scanning (e.g., scrubbing) starts automatically when the telescoping rod is locked against the inner lock and/or when the snout contacts the bottom. Optionally, wine is filtered until a desired cleanliness is detected, at which point a user may be alerted (e.g., using a sound generating sub-system). Optionally, removing the inner mechanism or in-barrel portion causes any excess wine in the system to be returned to the barrel, optionally in response to detection of exposure of the snout.

An aspect of some embodiments of the invention relates to using a centrifugal filter to separate particles out of wine. A first potential advantage of using a centrifugal filter is that filtering parameter (e.g., time, speed) may be adjusted to select the sizes of removed particles. A second potential advantage of centrifugal filtering is the avoidance of media which may adsorb and/or otherwise affect wine flavor materials. In some exemplary embodiments of the invention, the maximum acceleration in the filter is limited, to avoid damaging the wine, for example, acceleration may be limited to, for example, 50 g, 10 g, 5 g, 3 g or intermediate or smaller forces. In some cases, the acceleration limitation depends on a duration thereof and may be controlled, for example, by a controller, for example, as described herein.

In some exemplary embodiments of the invention, a feed in buffer is used to accumulate wine for fast flow through a filter. Optionally or alternatively, a feed out buffer is provided, for example, to allow wine to remain a desired time in the filter before being passed to the feed out buffer. In some exemplary embodiments of the invention, the pump is a fully auto vertical clean ic45-av—centrifuge, by Interfil, Australia or a food grade pump, for example, a tubular bowl centrifuge GQ150 (optionally reduced in volume) by Lilong of China. Other designs may be used as well. Optionally, what is desired is a lower volume, optionally an increase in filtering time is allowed. Optionally, for example as described herein, the pump can be used at multiple speeds and/or residence time (e.g., until wine is clean) and/or appropriate control circuitry for such functioning is provided.

In some exemplary embodiments of the invention, filtering is increased for more turbid wine and reduced for less turbid wine, for example, by increasing speed and/or dwell time (or reducing thereof, to reduce filtering effect). Optionally, a sensor is used to sense particle amount and/or size, and fed to circuitry for choosing filtering parameters.

An aspect of some embodiments of the invention relates to a wine management system. In some exemplary embodiments of the invention, a wine treatment system is transported to wine barrels for treatment of wine and/or thereof.

Optionally, the system stores a record of the type of wine and/or other treatment parameters and/or history. In some exemplary embodiments of the invention, the wine barrel is identified (e.g., using a machine readable code such as a barcode and/or using an RFID reader and/or by human entry of a human readable code) and the system outputs a desired treatment and/or parameters and/or sets parameters of a treatment system (e.g., time, turbidity target) automatically.

Optionally or alternatively, treatment of the wine, for example, filtering includes measuring eth wine (e.g., turbidity) which data is stored by the system. Storage may be on the mobile unit and/or on a remote and/or central unit.

In some exemplary embodiments of the invention, the system includes a user interface whereby a user can indicate a wine type and/or wine parameters and receive instructions and/or setting of the system.

Before explaining at least one embodiment of the invention in detail, it is to be understood that the invention is not necessarily limited in its application to the details of construction and the arrangement of the components and/or methods set forth in the following description and/or illustrated in the drawings. The invention is capable of other embodiments or of being practiced or carried out in various ways.

Exemplary System and Method for Cleaning Wine and/or a Containing Barrel

The present invention, in some embodiments thereof, relates to treatment of liquids and containers and, more particularly, but not exclusively, to cleaning wine (racking) and cleaning a containing barrel.

Cleaning Wine in a Barrel During In-Barrel Containment

Reference is now made to FIG. 1, which shows a flow chart of a method 100 for cleaning wine which is in a barrel, while transferring only a minority of the wine from the barrel, according to some exemplary embodiments of the present invention.

In method (100), some wine is transferred from a barrel (step 102); for example, to an external container or reservoir of a wine cleaning system. Optionally, wine is transferred by siphoning or by inserting a pressurized gas line into the barrel.

Alternatively, wine is transferred by pumping; for example, using a hand pump or a positive displacement pump. In some exemplary embodiments of the invention, an initial removal of wine is to prevent overflow of wine from the wine barrel when an in-barrel cleaning mechanism is inserted thereto.

In some embodiments, wine transfer occurs with a low contribution to mixing of wine layers in the barrel; for example, avoiding mixing sediment in a lower level of the wine with other wine, for example, as discussed in further detail in this application.

In some embodiments, wine turbidity is monitored (step 104). Optionally, transferring of wine optionally continues until the wine turbidity is below a maximum requisite value. Optionally, wine turbidity is monitored outside the barrel; for example, within a tube that transfers wine from the barrel. Alternatively, turbidity is monitored inside the barrel.

In some embodiments, wine is extracted and transferred from sediment-laden wine at a bottom layer of wine in the barrel. Optionally, wine turbidity is monitored at or near the bottom layer. For example, sediment-laden wine is transferred from the barrel until the wine turbidity is below a requisite maximum, e.g. about 10 NTU.

Optionally or alternatively, the turbidity is defined based on the maximum size of suspended particle (e.g., fewer than 10% of particles being larger than 30 microns, 20 microns, 10 microns 5 microns or intermediate sizes.

In some exemplary embodiments of the invention, transferred wine is filtered from particulate matter (step 106); for example, as discussed in further detail in this application. Optionally, wine is filtered with an interposing medium, such a strainer or filter paper. Alternatively, wine is filtered with no medium, for example, by centrifugation, with a device such as a centrifugal filter pump.

After filtration, wine is returned to wine in the barrel (step 108). Optionally, wine is returned by siphoning. Alternatively, wine is returned by pumping; for example, using a peristaltic pump. Optionally, wine is returned to a top layer of wine in the barrel.

Alternatively, wine is returned by spraying. Returning wine by spraying is potentially advantageous where addition of oxygen to the wine is needed. Optionally, whether to return by pumping or by spraying is decided in a closed-loop control depending, for example, based on reporting from reduction process detector(s) placed by the winemaker. In some embodiments, wine return occurs with a low contribution to mixing of wine layers in the barrel; for example, as discussed in further detail in this application.

In some embodiments, a volume of at most 20% of the wine is transferred from the barrel during in-place wine cleaning 100. Optionally, a volume of at most 10% of the wine is transferred. Potential advantages of transferring not more than 10% or 20% of the wine, or transferring a minority of the wine, compared with the prior art method of most to all of the wine, are reductions in labor costs and in possibility of wine damage due to oxidation and of wine loss entailed in transferring wine between containers. Additionally, in-place wine cleaning renders unnecessary a container with capacity as large or almost as large as the barrel, reducing the size and weight of a racking installation; for example, where the barrel is nearly full (e.g., 95-100% full), a container with capacity of only 10% or 20% of the barrel's capacity can be used. In some embodiments, the capacity can be smaller, for example, 1%-10%, for example, less than 5%, for example, if wine is extracted and returned multiple times during cleaning.

In some embodiments, blocks 102-108 are repeated; for example, until a requisite value of turbidity is achieved. Optionally, wine turbidity is monitored outside the barrel; for example, in a collection reservoir outside of the barrel.

Alternatively, turbidity is monitored inside the barrel. During the method, cleaned and unclean wine are both in the barrel. Optionally, a transfer and return of wine occurring with low contributions to mixing of wine layers in the barrel—for example, as discussed in further detail in this application—minimizes mixing of cleaned wine with unclean wine, thereby recontaminating the cleaned wine.

In some exemplary embodiments of the invention, the filtering system has a capacity that allows continuous removal of wine, filtering and return thereof.

In some exemplary embodiments of the invention, filtering is repeated every few days (e.g., 1-10, for example, 5-7), weeks (e.g., 1-10, for example, 3-6) or months (e.g., 1-4, for example, 2).

In some exemplary embodiments of the invention, the barrel used is one of a stand size of barrels, for example, as in table I below:

efficient if at the same time there is avoidance of mixing of wine layers which may spread the sediment and thereby undo the stratifying effect of natural settlement.

A wine cleaning system that reduces mixing between layers of wine in a barrel potentially prevents cleaner wine from becoming contaminated by mixing with dirtier wine. For example, preventing wine from a bottom sediment-laden layer 203 from transporting low-mass particles to a cleaner middle layer 202 above. Optionally or alternatively, for example, preventing microorganisms in wine from a top layer 201 from contaminating lower middle layers 202. Additionally, for example, low mixing of a cleaned layer 207 with dirtier layers prevents cleaned wine from becoming unclean.

Furthermore, a low-mixing wine cleaning system potentially renders an in-place wine cleaning more efficient, for example as discussed in further detail in the application. In some exemplary embodiments of the invention, once dirtier layers of wine are cleaned, a flow rate of wine is allowed to increase, potentially allowing faster cleaning throughput. This can allow an optimization of cleaning rate vs. wine dirtying rate (due to mixing), whereby wine dirtying rate is inversely related, in general, to the turbidity of the "dirty" wine.

Figure 3:
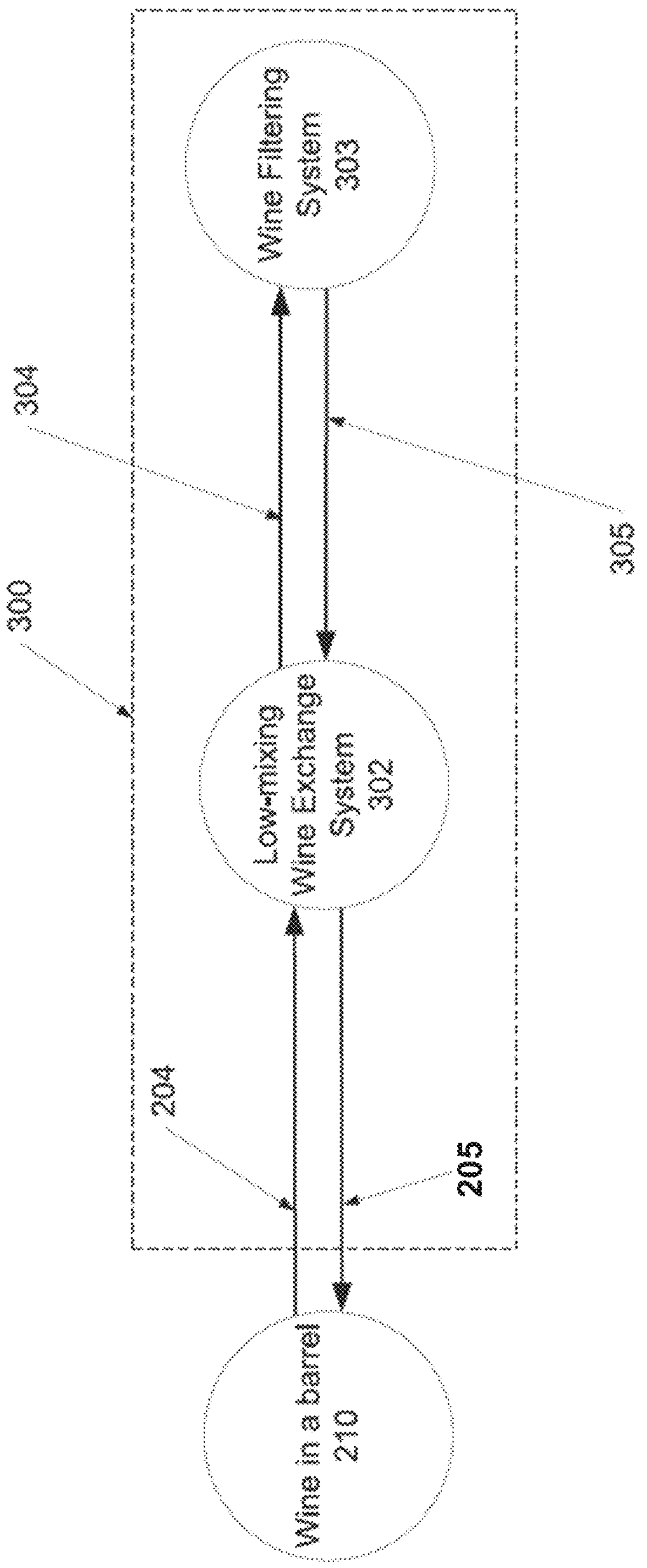
FIG. 3 is a block diagram of an in-place, low-mixing wine cleaning system, according to some embodiments of the invention.

Reference is now also made to FIG. 3, which shows a block diagram of an in-place, optionally low-mixing wine cleaning system 300, according to some exemplary embodiments of the invention.

TABLE I

| Metric Specs | BORDEAUX | BURGUNDY | 200 Liter | 265 Liter | HOGSHEAD | 114 Liter |
|---|---|---|---|---|---|---|
| Volume | 225 liters | 228 liters | 200 liters | 265 liters | 300 liters | 95 liters |
| Height | 93.35 cm | 88.9 cm | 87.6 cm | 93.35 cm | 99.6 cm | 73.6 cm |
| Bilge Circumference | 215.9 cm | 219.7 cm | 201.9 cm | 229.8 cm | 236.2 cm | 158 cm |
| Head Thickness | 2.54 cm | 2.54 cm | 2.54 cm | 2.54 cm | 2.54 cm | 2.54 cm |
| Stave Thickness | 2.54 cm | 2.54 cm | 2.54 cm | 2.54 cm | 2.54 cm | 2.54 cm |
| Bunghole Diameter | 5.4 cm | 5.4 cm | 5.1 cm | 5.4 cm | 5.4 cm | 3.8 cm |

Reduced Mixing of Layers

Figure 2:
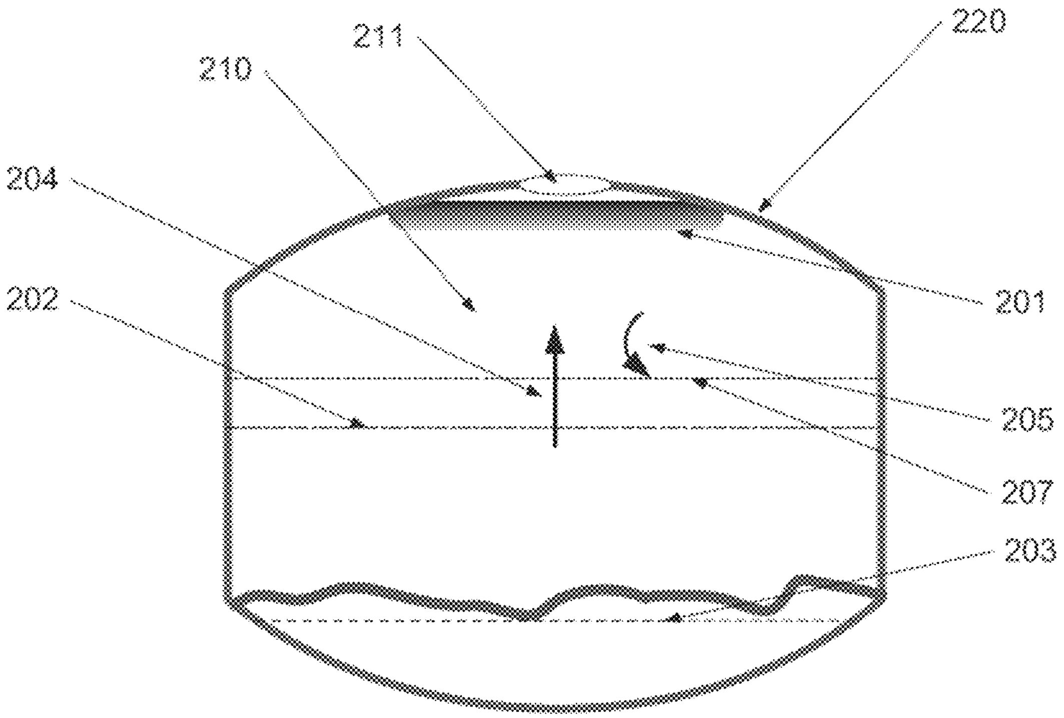
FIG. 2 is a side view simplified illustration of a barrel filled with wine during an in-place, low-mixing wine cleaning method, showing extraction of unclean wine, return of cleaned wine and types of layers of wine, according to some embodiments of the invention.

Reference is now made to FIG. 2, showing extraction 204 of unclean wine and return 205 of cleaned wine in a non-limiting example of a system for cleaning wine 210 in a barrel 220 with low mixing between wine layers, according to some exemplary embodiments of the invention.

In some exemplary embodiments of the invention, barrel 220 is a wooden barrel and/or includes flavor giving portions, such as wood portions. Such barrels often have an opening only on top.

Wine 210 in a barrel 220 is often separated into different layers. The aging process may have separated wine 210 in the barrel 220 into different layers. For example, a bottom layer 203 containing sedimentary deposits and/or particles; a top layer 201 potentially contaminated with organic matter, such as yeast and aerobic microorganisms, and floating debris; and a middle layer 202 possibly containing some suspended particles. Additionally, for example, there is a layer 207 of cleaned wine being returned 205 to wine in the barrel.

In some exemplary embodiments of the invention, use is made of natural (e.g., slow) settlement processes and wine and sediment is extracted substantially only from a bottom layer of the barrel. However, this method may be more A low-mixing wine exchange system 302 controls mixing between layers in wine 210 that is induced by extraction 204 and/or return 205 of wine 210 in the barrel 220. The extent of mixing between layers is lessened by reducing agents of mixing, such as flow velocities, presence of eddy currents, and drag.

In some embodiments, in-place wine cleaning system 300 includes a transfer 304 of extracted wine 210 to a wine filtering system 303. Optionally, in-place wine cleaning system 300 includes a return 305 of filtered wine from the filtering system 303 to the low-mixing wine exchange system 302. Components of low-mixing wine exchange system 302 and wine filtering system 303 are discussed in further detail in this application.

Optionally, in-place wine cleaning system 300 performs with access to the interior of the barrel 220 restricted to a bung hole 211 of the barrel, with a diameter, for example, of about 50 mm.

Low-Mixing Wine Exchange System

Figure 4:
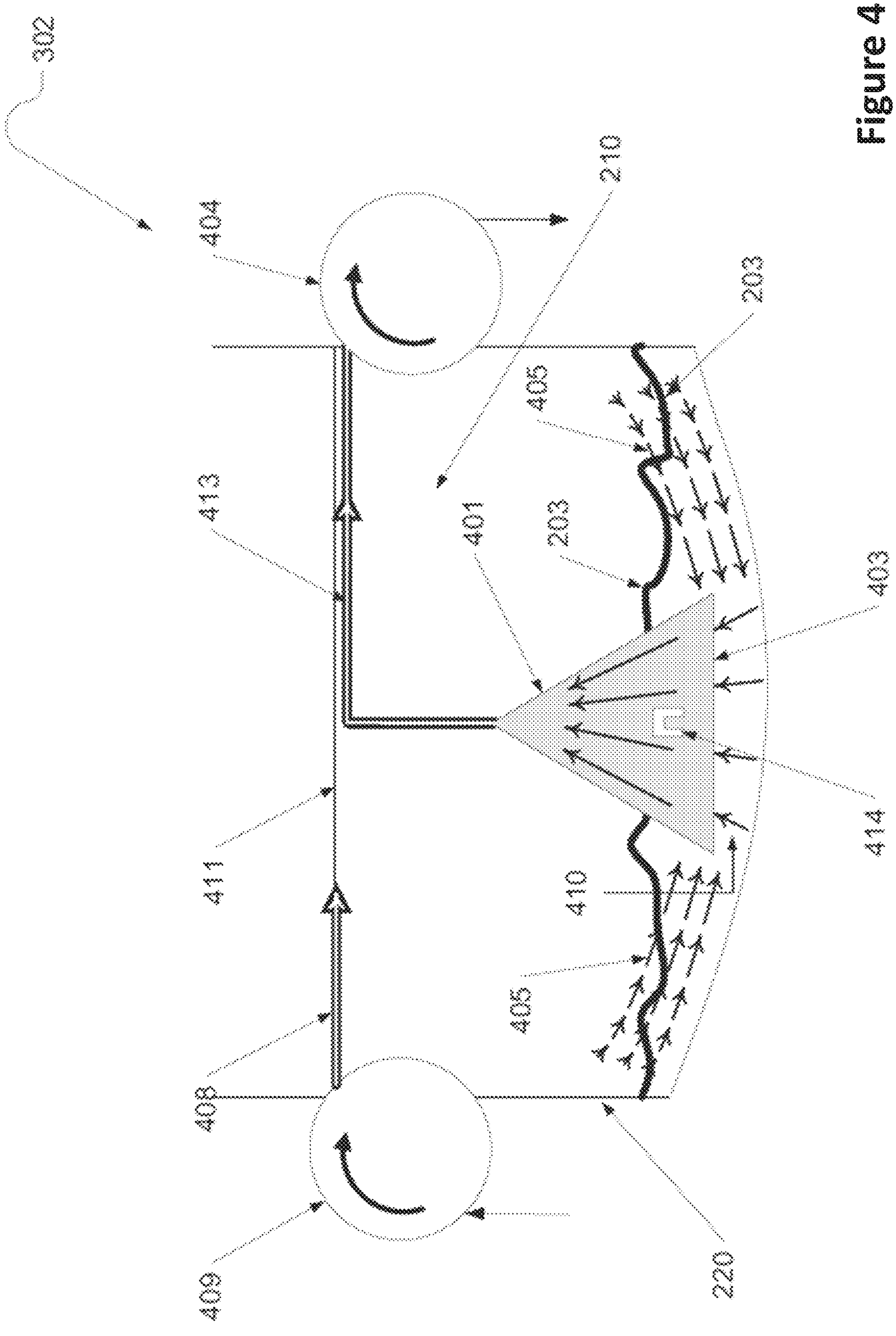
FIG. 4 is a diagram of a low-mixing wine exchange system, according to some embodiments of the invention.

Reference is now also made to FIG. 4, which shows a low-mixing wine exchange system 302, containing an extracting snout 401, optionally optimized for low mixing, according to some exemplary embodiments of the invention. Optionally, an opening 403 of snout 401 is positioned at a bottom, sediment-laden layer 203 of wine 210 in barrel 220, for example as discussed in further detail in the application.

In some embodiments, configuration of snout 401, such as size, shape, and orientation, is selected for minimizing mixing flows within wine 210 in the barrel 220 caused by extraction. Optionally, snout opening 403 has an area as large as 50 mm, 60 mm, 100 mm or intermediate or smaller sizes. Optionally, material of snout 401 is flexible so as to allow its entry into a bung hole 211 of the barrel, e.g. as discussed further in this application. A large area snout opening 403 has the potential advantage of minimizing flow velocities 410 near the opening 403, for a given extraction flow rate 413, and of outlying currents 405, thereby potentially reducing the extent of eddy currents and mixing of wine layers.

Optionally, the snout is aligned so that a plane normal to a direction of flow across snout opening 403 is generally horizontally oriented (e.g., within 20 degrees of the horizontal). A horizontally oriented snout opening has a potential advantage of extracting wine at only one layer, minimizing mixing due to wine entering snout 401 over a range of layers.

In some embodiments, extraction flow rate 413 and/or return flow rate 408 is adjusted according to degree of mixing. A potential advantage of adjusting flow rates is that it may allow faster and/or more, efficient in-place wine cleaning. For example, flow rate is lowered to reduce mixing; snout 401 thereby extracts sediment-laden wine with a minimal amount of cleaner wine. When tendency for mixing is lower, flow rate(s) optionally increase to speed up the wine cleaning process.

In some exemplary embodiments of the invention, snout 401 scans at least part of the bottom of the barrel. Optionally or alternatively, stationary suction allows sediment particles to flow down to where the snout is located (e.g., if the bottom of the barrel is concave and the snout is at a lowest part thereof).

Optionally or alternatively, the degree of mixing allowed is evaluated according to wine turbidity. Optionally a turbidity sensor 414 is placed in the wine; for example, near snout opening 403, with flow rates optionally elected (e.g., using a table in memory) based on the sensor measurements.

In some exemplary embodiments of the invention, turbidity is measured and compared at different layers of wine, in order to evaluate the degree of mixing and adjust the flow rate of wine extraction and/or return accordingly. For example, turbidity is measured in or near a bottom sediment-laden layer 203 and in a higher, cleaner layer 202. If the two turbidity values start to converge (e.g., at a higher level), possibly indicating increased mixing of layers, flow rate(s) are accordingly reduced. A low level of turbidity in both layers may indicate that filtering of the lower level is progressing as desired. Optionally or alternatively, the absolute level of turbidity is also used to determine mixing level and/or allowed mixing rate.

In some embodiments, cleaned extracted wine is returned to wine 210 in the barrel 220 at a top layer 411 of wine in the barrel. Returning wine to a top layer 411 of wine in the barrel has the potential advantage that there is no opportunity above the cleaned wine to mix with unclean wine. Additionally, cleaned wine being returned at a top layer is farthest away and least subject to mixing with wine from a bottom layer 203, laden with sediment and among the most turbid wine in the barrel. Optionally, the return is below the wine surface, for example, at least 1-5 cm below, so as to avoid mixing wine and/or debris and/or bacteria from the upper surface of the wine with wine in the body of the wine.

Optionally, wine is returned to the top layer 411 by spraying (e.g. from above the wine surface). A potential advantage of returning wine by spraying is addition of oxygen to the wine, if needed, where air in the barrel was not purged with an inert gas, as described in further detail in the application.

While in some embodiments filtered wine is returned before all the sedimented wine is removed from the barrel, in some embodiments, wine return does not begin until extraction is complete. A potential advantage of not returning wine until extraction is complete is avoidance of turbulence that could mix layers of wine. A potential disadvantage is that a larger out-of-barrel storage may be needed.

In some embodiments, either or both extraction and return are driven by an extraction pump 404 and a return pump 409, respectively. Optionally, either or both pumps 404, 409 are peristaltic pumps. A peristaltic extraction or return pump has the potential advantages of being accurately controllable (e.g., desired speed) and/or being self-priming and speed-controlled movement of wine.

In some embodiments, extraction pump 404 is provided inside the barrel, for example, within the snout.

Exemplary Systems

Figure 5A:
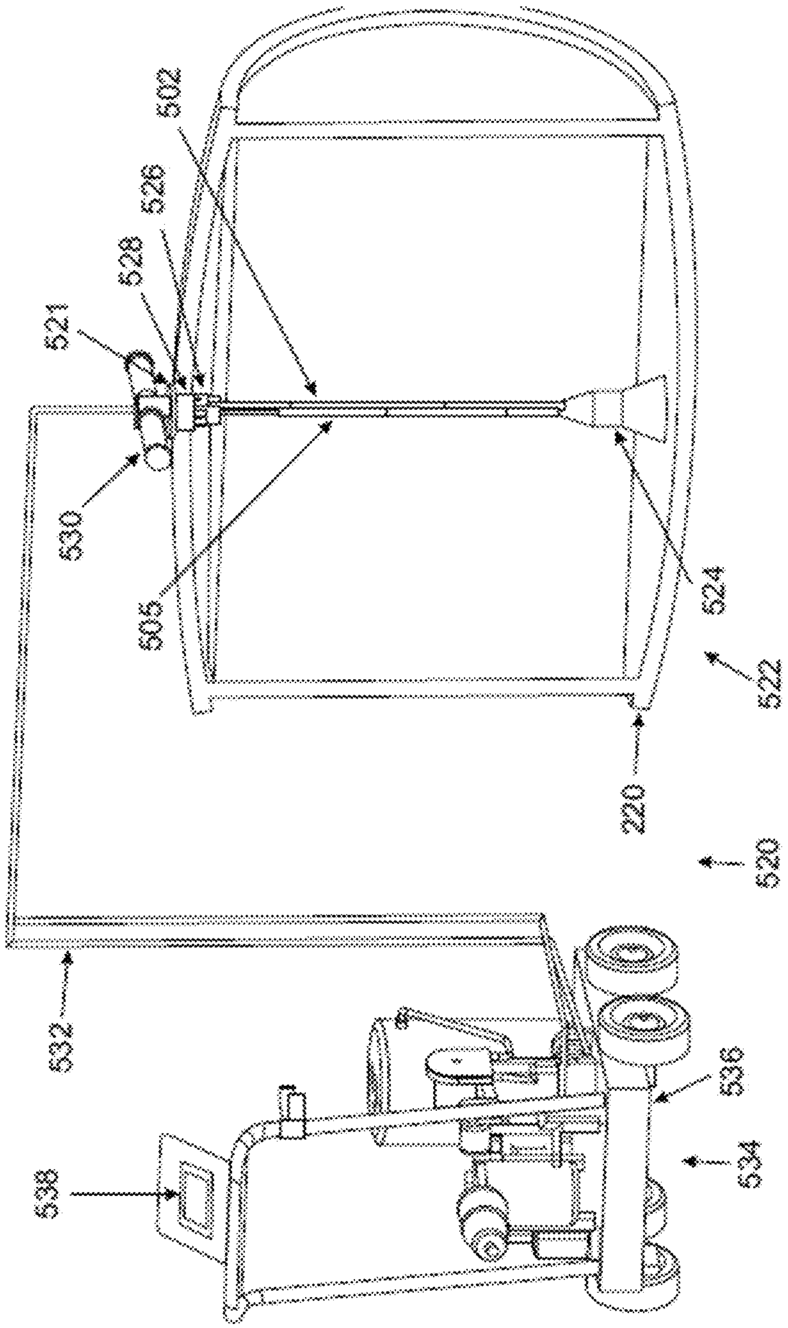
FIG. 5A is a schematic of an exemplary embodiment of a wine cleaning system, in accordance with an exemplary embodiment of the invention.

FIG. 5A is a schematic showing of a wine cleaning system 520, in accordance with an exemplary embodiment of the invention. An in-barrel portion 522 is inserted into a barrel 220 and optionally locked in a bung-hole 521 thereof, using an optional lock 528 (see also FIG. 5C). An outer system portion 534 is optionally connected to in-barrel portion 522 via one or more bendable and/or flexible tubes 532. As shown, outer system portion 534 may include a wine processing portion 536 and an optional controller and/or user interface 538.

Optionally, a handle 530 is provided for manipulating in barrel portion 522, for example, during insertion and extraction thereof.

Referring in more detail to in-barrel portion 522, in some embodiments of the invention portion 522 includes a lower mechanism or cleaning head assembly 524 mechanically coupled by a rod 505 to an upper mechanism or assembly 526 (e.g., for swinging) and also including a wine removal tube 502.

Figure 5B:
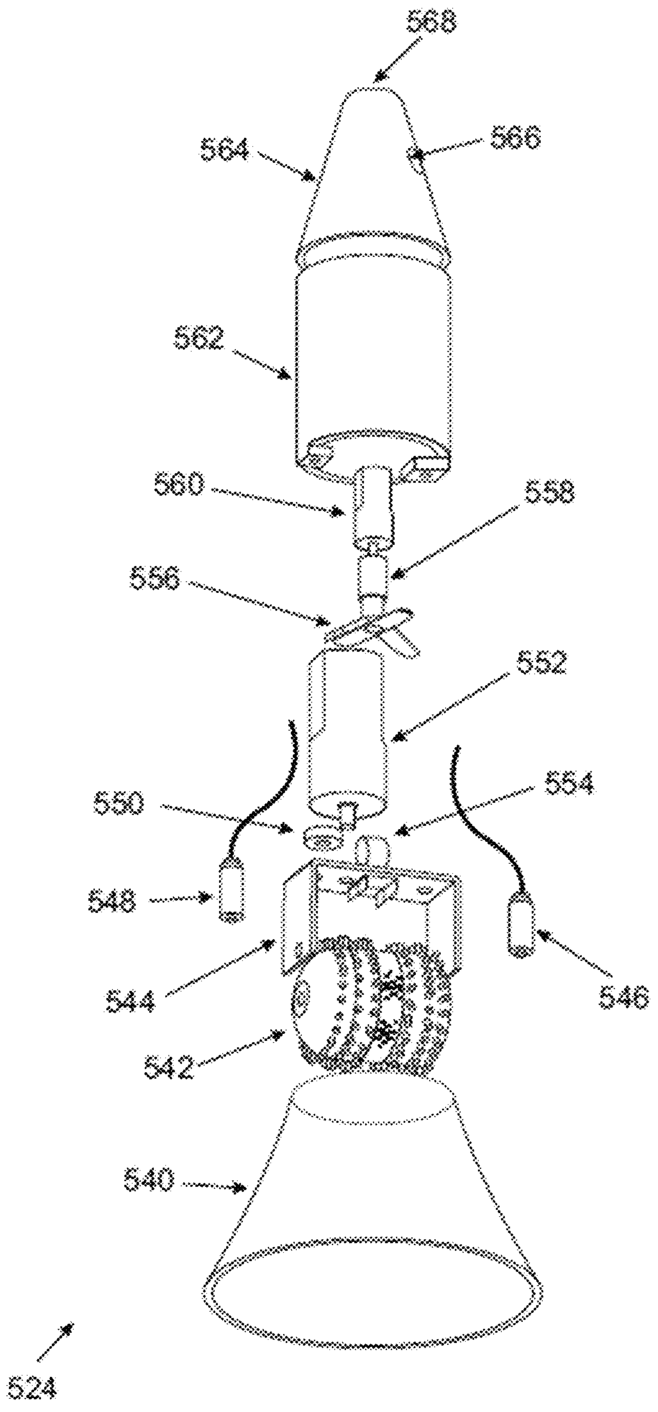
FIG. 5B is an exploded view simplified illustration of a lower mechanism of an in-barrel portion of a wine cleaning system in accordance with an exemplary embodiment of the invention.

FIG. 5B is an exploded view of a lower mechanism or cleaning head assembly 524 of an in barrel portion 522 of a wine cleaning system 520 in accordance with an exemplary embodiment of the invention.

In some exemplary embodiments of the invention, mechanism or cleaning head assembly 524 includes a housing with mechanical elements inside and one or more optional sensors, optionally on the outside of the housing. In some exemplary embodiments of the invention, the housing comprises a snout 540, for example, in the form of a truncated cone, a cylindrical portion 562 (e.g., to house a motor and/or chopper) and a conical cap portion 564. In some embodiments, a single piece housing is provided.

In some exemplary embodiments of the invention, for example as described below, mechanism 524 includes one or more scrubbing elements 542, for example, wheels with protrusions, positioned to contact the bottom of the barrel when snout 540 is pushed towards the barrel bottom. Optionally, when such scrubbers 542 turn, they remove encrusted matter form the barrel bottom and into the volume of snout 540. If suction is applied, e.g., via tube 502, then such encrusted matter is removed from the barrel and does not intermix with wine outside the snout. Optionally, a chopper 556 is provided to chop up any large pieces of sediment and/or scrubbed encrusted matter, which may prevent clogging of tube 502. Optionally, scrubber 542 is powered using an inbarrel DC motor 552, connected via a gear train 550, 554 to a gear coupled to scrubber 542. Other powering methods may be used as well. Chopper 556 is optionally powered by a second DC motor 560, optionally coupled via a mechanical link 558 to blades of chopper 556. While the system is described with multiple motors, in some embodiments fewer motors are provided, for example, only one electrical motor and a power train is used to convey power to the various parts of the inner apparatus (e.g., using rotating rods and/or chains) and/or using pneumatic and/or hydraulic power sources.

Optionally, one or more sensors are provided, for example, a fluid level sensor 548 (e.g., to ensure operation is coordinated with insertion in liquid and/or a turbidity sensor 546, for example, an optical sensor, optionally for providing feedback on cleaning progress and/or mixing. Optionally, such sensors are within snout 540.

Alternatively, at least one sensor may lie outside of the snout.

Wiring for the sensors and DC motors (e.g., instead of optional wireless transmission and in-barrel electrical or mechanical storage systems), is optionally provided along or within rod 505. Optionally, the pole itself is used for power transfer and/or data is modulated on the power line.

Referring to cap element 564, an axial coupler 568 is optionally provided for coupling mechanism or cleaning head assembly 524 to rod 505. Optionally or alternatively, an opening 566 is provided for linking the inner volume of the housing to tube 502, for wine extraction.

In some exemplary embodiments of the invention, some or all of in-barrel portion 522 is disposable. Optionally, only the plastic parts and/or parts in contact with wine are disposed of. Optionally, some parts are sterilized. For example, the tubing and scrubbing elements may be disposable, while the wiring and motors may be encased in disposable portions. The chopper and/or sensors are optionally disposable too. Optionally, portion 522 includes one or more openings, optionally tearable or self-closing, through which the motors are removed and inserted.

Optionally, the wires are also replaced.

Optional Exemplary Cleaning Head Assemblies

Still referring to FIG. 5B, in some embodiments and as explained herein, in-barrel portion 522 lower mechanism 524 includes cleaning head assembly 590 with one or more scrubbers 542. Optionally, scrubber 542 is circular. Optionally, scrubber 542 is a brush. Optionally, a flexible drive cable spins the brush during scrubbing. Optionally, scrubber 542 is collapsible, for example, for insertion through the bung hole. Optionally or alternatively, scrubber 542, or a portion thereof that contact the barrel are softer than the barrel materials (e.g., wood) so as to reduce damage thereto. Optionally, scrubber 542 is disposed in a snout 401 of a low-mixing wine cleaning.

In some exemplary embodiments of the invention, cleaning head assembly 590 includes one or more turbidity sensors 546. Optionally turbidity sensor 546 detects an amount of matter removed by scrubbing possibly indicating when scrubbing is completed. Optionally, cleaning head assembly 590 includes one or more liquid contact sensors 701 as explained in further detail elsewhere in this disclosure.

Figure 5C:
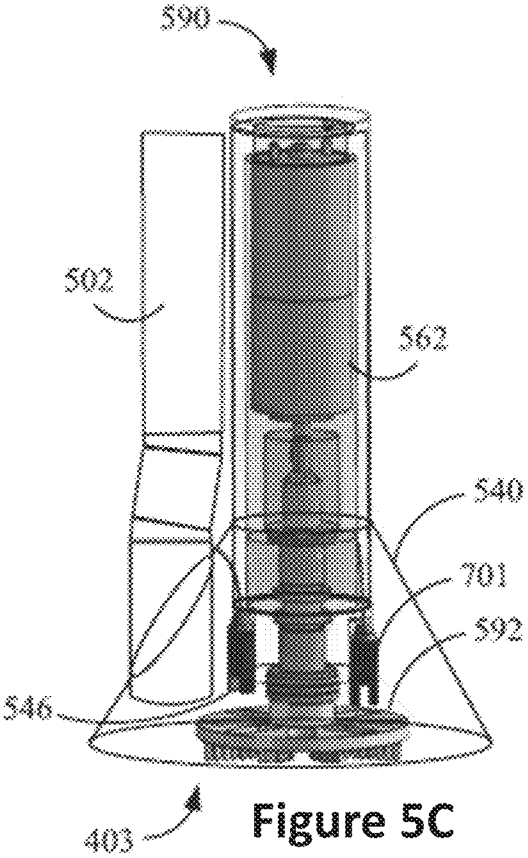
FIGS. 5C and 5D are side view and cross-section view simplified illustrations of exemplary embodiments of cleaning head assemblies in accordance with the invention.

In some exemplary embodiments of the invention and shown in FIGS. 5B-5C, a cleaning head assembly 590 includes a rotating scrubber or brush 590 aligned along a plane of rotation parallel to a direction of flow across snout opening 403. A potential advantage in the configuration of brush 592 and configurations similar thereto is in the limited contact area between brush 592 and an inner surface of a barrel. Limited contact control the volume of liquid in which removed sediment may be suspended before being completely suctioned and removed via snout 401 out of the barrel. A brush such as brush 592 can be employed, for example, for localized spot treatment.

A potential advantage in the configuration of brush 592 and configurations similar thereto is in that brush 592 can be used as a wheel and assist in relocating cleaning head assembly 590 within the barrel.

In the exemplary embodiment of FIGS. 5B-5C, sensors 546/701 may be disposed to one side of rotating brush 592 or each on an opposite side of rotating brush 592.

As shown in FIG. 5C, which is an exemplary embodiment of a cleaning head assembly 524 in accordance with the invention, assembly 524 includes a scrubber or brush 592 aligned along a plane of rotation normal to a direction of flow across snout opening 403. Optionally, rotating brush 592 may be sized at varying sized radii. In some embodiments, rotating brush 592 may be sized to have a small radius. For example and as explained above, a potential advantage of a small radius brush 592 is in the limited contact area between a small radius brush 592 and an inner surface of a barrel. Limited contact controls the volume of liquid in which removed sediment may be suspended before being completely suctioned and removed via snout 540 out of the barrel. A brush such as small radius brush 592 can be employed, for example, for localized spot treatment.

In some exemplary embodiments, rotating brush 592 may be sized, for example, to have a large radius. A potential advantage of a large radius brush 592 is in the increased surface "coverage" (i.e., cleaned area per given period of time) of an inner surface of a barrel. The increased "coverage" of exemplary embodiment of FIG. 5C may shorten cleaning time of a barrel.

Figure 5D:
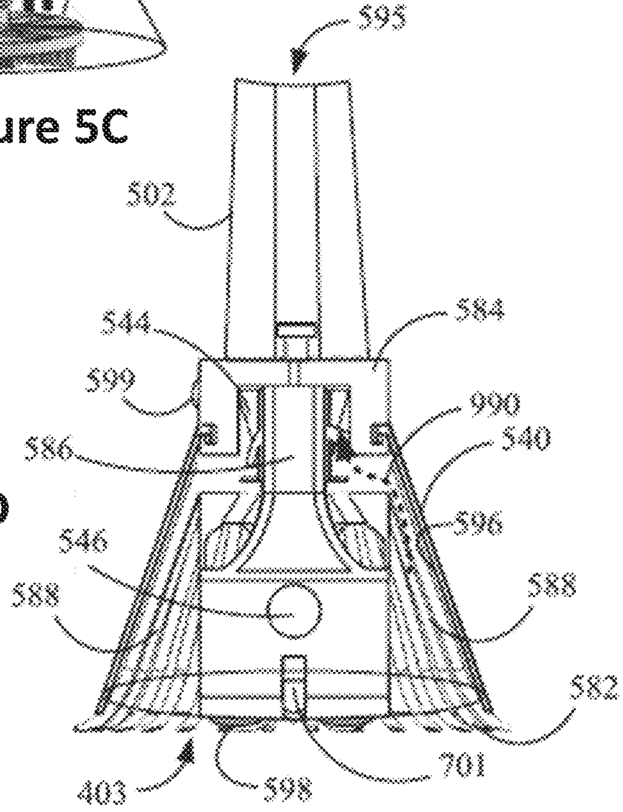

FIG. 5D, which is a cross-section view simplified illustration of an exemplary embodiment of a cleaning head assembly 524 in accordance with the invention, illustrates an embodiment of cleaning head assembly 595 in which scrubber or brush 582 is powered by the flow of liquid suctioned from the barrel through a turbine 544. In some embodiments, rotating brush 582 is aligned along a plane of rotation normal to a direction of flow across snout opening 403.

In some embodiments, rotating brush 582 is coupled to a hollow bearing 584. Optionally, bearing 584 is rotationally coupled to an axis 586 and turbine 544. In some embodiments, turbine 544 is disposed within a path of flow indicated by arrow 990 of liquid suctioned out of the barrel. In some embodiments, turbine 544 rotates about axis 586. In some embodiments, turbine 544 is aligned along a plane of rotation normal to a direction of flow of the suctioned liquid across snout opening 403.

In some embodiments, bristles 588 of brush 582 are attached on one side thereof to a circumference of hollow bearing 584 and extend towards snout opening 403 along an inner wall 596 of a snout 540. In some embodiments, axis 586 includes one or more casters or wheels 598. Optionally, casters 598 protrude beyond snout opening 403. Optionally, sensors 546/701 may be disposed centrally to rotating brush 582.

A potential advantage of casters 598 is in that when casters 598 are in contact with the interior surface of a barrel, snout 540 is slightly elevated off the surface. This elevation prevents edges of snout 540 from collapsing after becoming wedged in cracks and crevices and allows for a smoother translation of cleaning head assembly 595 along the curved interior surface of a barrel.

Additionally, a potential advantage of casters 598 is in that when casters 598 are in contact with the interior surface of a barrel, casters 598 bear the weight of in-barrel portion 522 and remove load from of bristles 588. This allows to reduce wear of bristles 588.

In some embodiments, bearing 584 includes a UV sterilization light source 599 for sterilization inside the barrel of barrel surfaces surrounding a cavity above the wine level.

Additional structural details of exemplary embodiments of system 520 are described herein, including hereinbelow.

Cleaning a Wine Layer

Reference is now also made to FIG. 5D, which shows an inner apparatus 501 of an in-place wine cleaning system 300 whose snout 401 extracts wine from a sediment-laden bottom layer 203 of wine 210 in a barrel 220 for cleaning, with wine returned at a top surface layer 411, according to some exemplary embodiments of the invention. Optionally, a turbidity sensor 414 monitors and reports wine turbidity to a controller; for example, as discussed in further detail within this application. As can be appreciated, mechanism or cleaning head assembly 524 and sensor 546 (of FIG. 5B) may serve in some embodiments of the invention.

During cleaning, top layer 411 usually contains the most sediment-free wine among wine 210 in the barrel 220 (though the upper surface of the wine may be contaminated with bacteria and/or debris). Middle layers (such as 202) get gradually higher in turbidity with increasing depth within wine 210 in barrel 220. Among the highest turbidities of wine 210 in the barrel 220 is at a bottom layer 203. A turbidity profile vs. depth of wine 210 in barrel 220 is characterized by a transition region, a range of layers where the wine turbidity profile turns sharply higher with increasing depth.

In long standing wine, it is often expected that the majority of sediment is at or near the bottom of the barrel. In some exemplary embodiments of the invention, only wine near the bottom is cleaned, optionally reducing damage to the wine.

If more than a small amount of wine is removed and wine is returned near the top, the transition region may shift downwards as unclean wine is extracted from a bottom layer 203 and cleaned wine is added to top layer 411. Optionally, the transition layer continues shifting downwards until reaching snout opening 403.

Optionally, a low-mixing wine exchange system 302 limits mixing of wine across layers in the transition region. Optionally, the transition region becomes narrower with continued cleaning and remains narrow, limited mainly by unavoidable mixing due to diffusion and a small extent of eddies.

A potential advantage of a wine cleaning system with an opening 403 of a snout 401 extracting unclean wine at a bottom layer and return of clean wine at a top layer 411, is the ability to selectively clean different volumes of wine. For example, as wine extraction progresses and the lower layers of wine are extracted, higher layers of wine may migrate downwards to be cleaned.

In some exemplary embodiments of the invention, a low-mixing wine exchange system 302 enables effective in-place wine cleaning, since, wine with high amounts of turbidity are cleaned first, and this turbidity does not spread or spreads a small amount, due to the act of cleaning. Optionally, over-cleaning is avoided by automatically measuring wine turbidity. It is noted that with low mixing, a transition region between sedimented wine and un- or less-sedimented wine and/or between cleaned and unclean wine is sharper than might otherwise be the case.

An additional potential advantage of positioning snout opening 403 near a bottom layer 203 is that wine near a bottom layer 203, laden with sediment and among the dirtiest, most turbid wine in the barrel is quickly extracted for cleaning.

Additionally, snout opening 403 extracts sedimented wine directly, with less opportunity to mix with cleaner wine. Optionally, for example, as described below, such wine can be removed together with encrusted material which is mechanically removed from a bottom of the barrel. Optionally, a spacing between the snout and the barrel is selected to allow wine inflow into the snout, for example, at a low speed and/or high enough volume and/or low turbulence level. Optionally, the spacing is selected so that all the sedimented wine that it is desired to extract and clean is sucked into the snout. This may depend on the snout design and/or flow speeds.

In some exemplary embodiments, snout 401 is held in place in wine 210 in barrel 220 by suspension from a bung hole 211 of barrel 220.

In an exemplary embodiment of the invention, a supporting member (e.g., rod 505) holds the snout 401 in position. Optionally, member 505 is elastically pre-disposed to lengthen and pushes snout 401 towards a bottom of the barrel. Optionally, a lock 570 serves to stabilize an opposite end 511 of member 505.

Optionally, extraction hose 502 carries extracted wine out of wine 210 in the barrel 220. Optionally, a return hose 509 returns cleaned wine to wine 210 in the barrel 220.

Figure 5E:
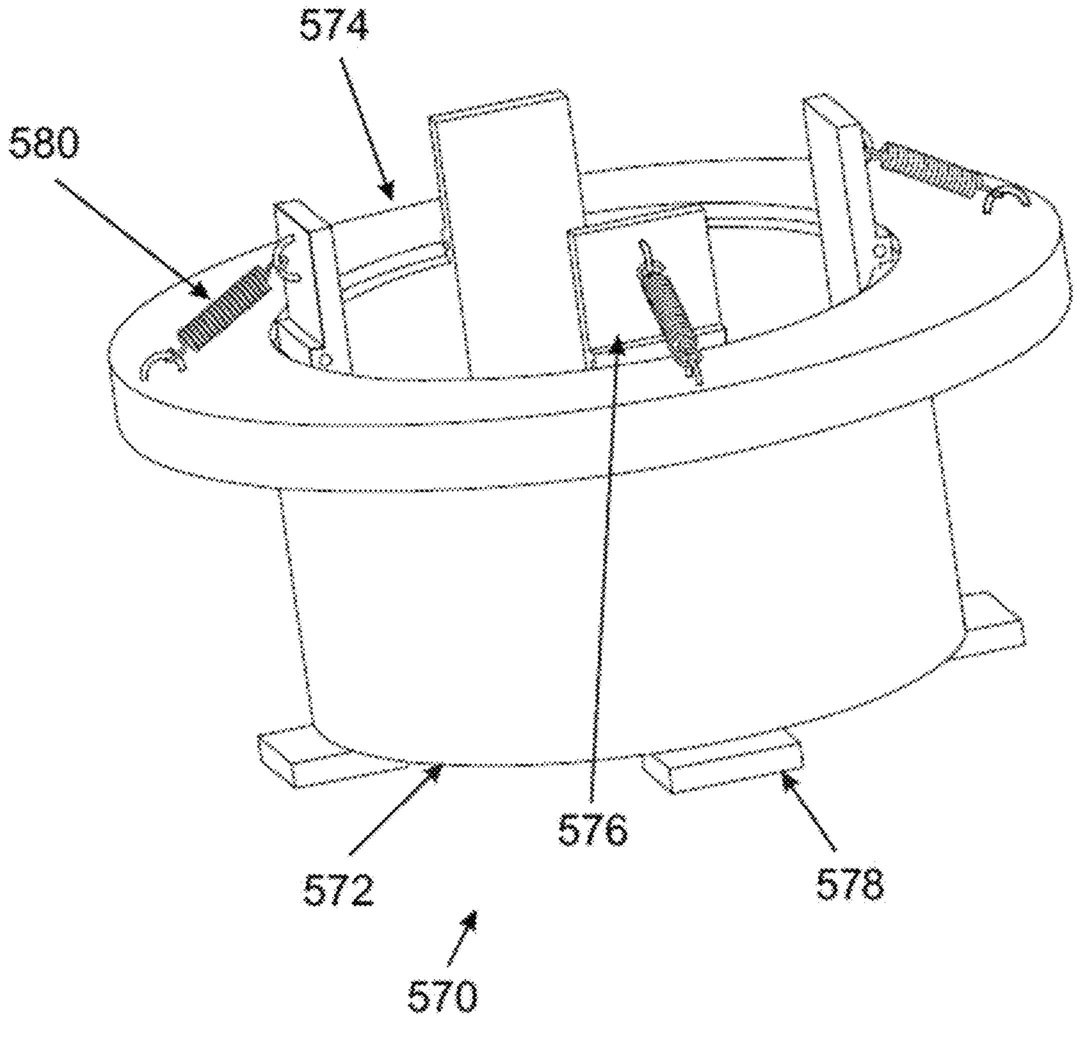
FIG. 5E is perspective view simplified illustration of a lock mechanism, of an in barrel portion of a wine cleaning system in accordance with an exemplary embodiment of the invention.

FIG. 5E is perspective view of a lock mechanism 570, of an in-barrel portion of a wine cleaning system in accordance with an exemplary embodiment of the invention.

In some exemplary embodiments of the invention, mechanism 570 includes a body 572 sized to fit in a bung-hole. Optionally, multiple mechanisms 572 are provided, so as to match various sized bung holes. Optionally or alternatively, body 572 is radially inflatable so as to expand and fit various sized bug-holes. Optionally or alternatively, a cylindrical adaptor (not shown) is mounted on body 572 for larger bung-holes. Optionally, (not shown) a silicon layer (e.g., a ring) is provided on body 572 to seal against the bung hole.

A ring 574 having an outer diameter larger than the bung hole prevents over insertion of mechanism 570 and also serves for locking, for example, as described below. Optionally, a sealing layer (e.g., a silicon ring, optionally compressible) is provided on body 572 so as to fit between body 572 and the outer surface of the barrel.

In some exemplary embodiments of the invention, locking is by one or more (e.g., 3 or 4) L shaped tabs 576 having a lip 578 which fits against an inner surface of the barrel, when mechanism 570 is inserted into the barrel. Optionally, a tab 576 is spring loaded, using a spring 580. Optionally, lips 578 are wedge shaped (thicker near their attachment to tab 576 and/or inclined, so as to encourage friction locking against the inner surface of the barrel.

As noted herein, the in-barrel portions 522 are optionally inserted into the barrel via an aperture in ring 574 and 572. Once in place, rod 505 optionally rests against lock 570 and/or is otherwise restrained vertically, so as to allow rod 505 to push snout 401 towards a bottom of the barrel and/or take part in repositioning thereof.

Vertical Snout Movement

While in some preferred embodiments of the invention only a small amount of wine is extracted (e.g., only wine in the lower 30%, 20% or 10% or less of the height of the barrel), for example from the bottom of the barrel, in some embodiments, more wine is extracted. In some embodiments, for example, as noted above, leaving the snout at the bottom of the barrel and returning wine to the top of the wine will possibly cause the uncleaned (or otherwise unprocessed) wine to migrate down to the snout.

Figure 5F:
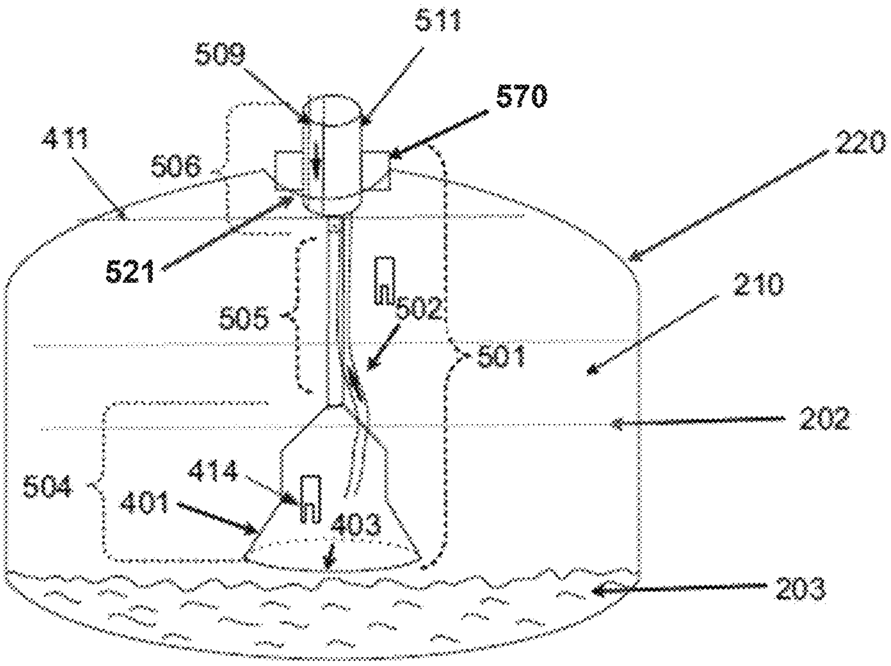
FIGS. 5F-5H are side view simplified illustrations of an inner apparatus installed in wine in a barrel, extracting wine at different layers of wine in the barrel, according to some embodiments of the invention.
Figure 5G:
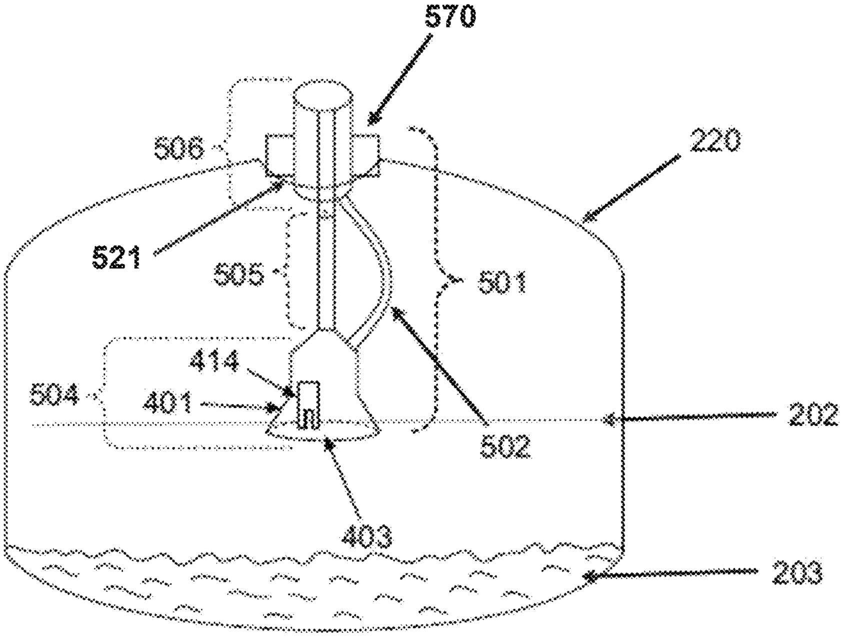
Figure 5H:
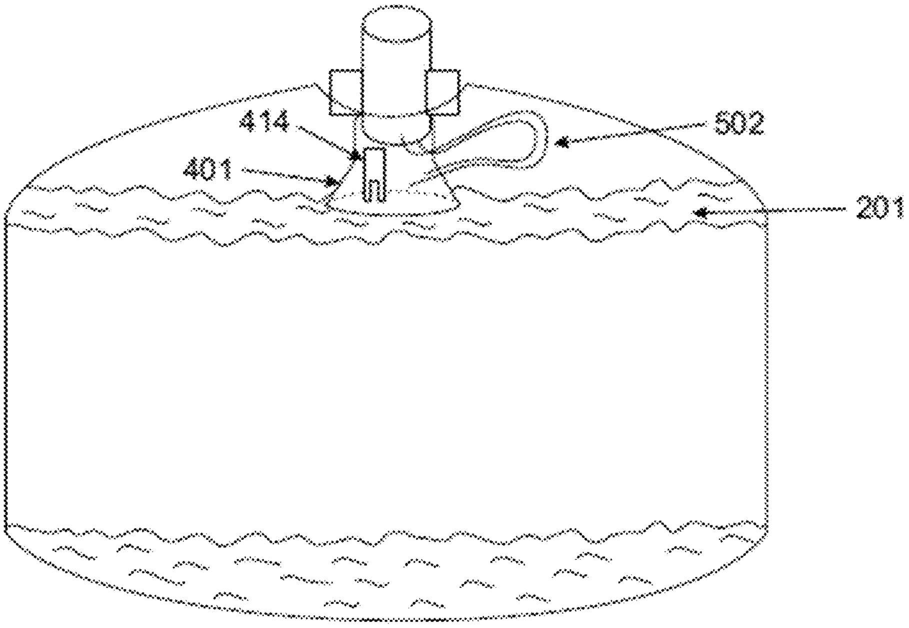

In some embodiments of the invention, cleaning is provided only at some layers of the wine (e.g., not only the bottom) and/or at multiple layers. Reference is now made to FIGS. 5E-5F, showing a snout 401 movable over a range of layers of wine 210 in barrel 220, according to some exemplary alternative embodiments of the invention. A potential advantage of a movable snout 401 is the ability to extract suspended particles from a range of middle layers 202 below snout opening 403, as shown in FIG. 5E. Another potential advantage is the ability to extract wine at a top layer 201 containing floating debris, as shown in FIG. 5F.

Optionally, snout 401 is repositioned by retracting and/or shortening rod 505 (e.g., via a pull wire which optionally which acts against a self-lengthening feature thereof and/or an actuator optionally provided therein). Optionally, supporting member 505 is telescoped to an adjustable length (e.g., less than 150% of a diameter of the barrel, for example, based on table I above) in order to position snout 401.

Optionally, a controller repositions snout 401 in an automated closed loop. It is noted that in a bottom-located snout, such repositioning can be a consequence of a self-lengthening rod design.

Figure 6:
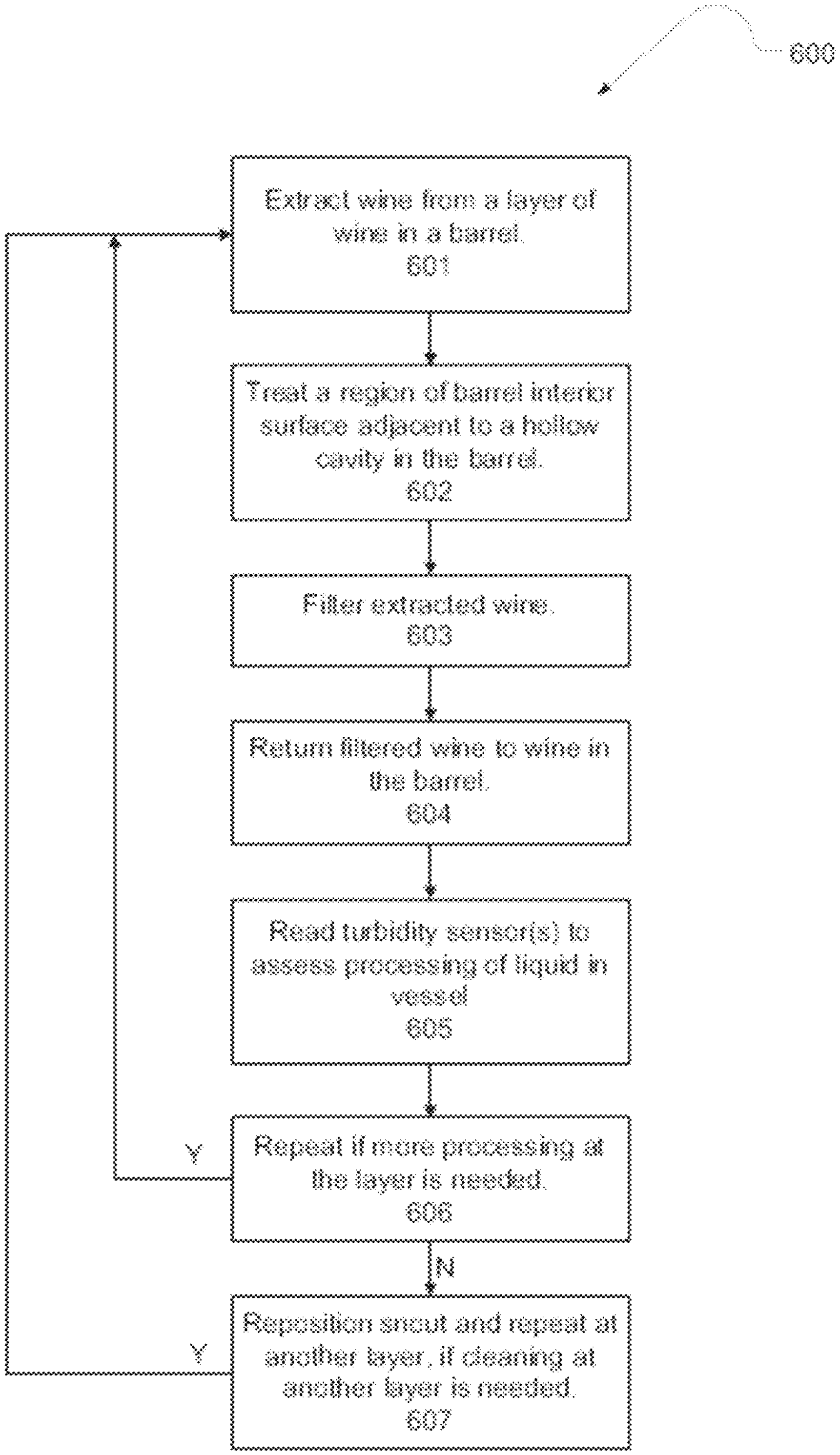
FIG. 6 is a flow chart of an exemplary method for cleaning wine in a barrel at different layers of wine in the barrel, according to some embodiments of the invention.

Reference is now made to FIG. 6, which shows a flow chart of a wine cleaning method 600 for cleaning wine at one or more layers of wine in a barrel, according to some exemplary embodiments of the invention.

Wine is extracted from a layer of wine (step 601). The layer can be, for example, a bottom layer laden with sediment. Optionally, extracting is done with a low-mixing extraction system 300.

Optionally, a region of the barrel interior surface alongside a hollow cavity in the barrel is treated (step 602); for example, using a UV sterilization apparatus, for example, as described in further detail below.

Extracted wine is filtered (step 603).

Filtered wine is returned to the wine (step 604) in the barrel.

Each of blocks (steps 601-604) is continuous and/or stepwise.

Optionally, a measurement of wine turbidity is made (step 605), for example, by reading one or more turbidity sensors. Optionally, the assessment is made of wine at or near the layer of wine being extracted. Steps 601-605 are optionally repeated if necessary (step 606). For example, if an assessment of turbidity of wine in the barrel does not meet a requisite value. In some embodiments, cleaning method 600 is complete.

In some embodiments, in one or more iterations of the method, wine extracted and filtered in a preceding iteration is not returned to the barrel until extracting wine (step 602). Such take-before-return embodiments can enhance non-mixing benefits by keeping some cleaned wine physically separated from wine in the barrel during wine extraction. Upon completion of processing wine in the barrel, wine extracted in a last iteration can be returned to wine in the barrel.

In some exemplary embodiments of the invention, steps 602-606 repeated at one or more layers (step 607). In some embodiments, multiple layer cleaning is achieved using a stationery snout inside of wine in barrel. Layers below a downwards migrating transition region are cleaned, until the transition layer reaches the snout opening. Optionally, the snout opening is positioned near a bottom layer of wine in the barrel.

In some alternative embodiments, a snout can be repositioned to a different height in the barrel in order to clean a layer at that height. Cleaning is then performed with extraction at another layer. Optionally, processing method 600 is first performed at a top layer. Optionally, cleaning method is repeated at least once at successively lower layers.

Exemplary Inner Apparatus Insertion

Figure 7:
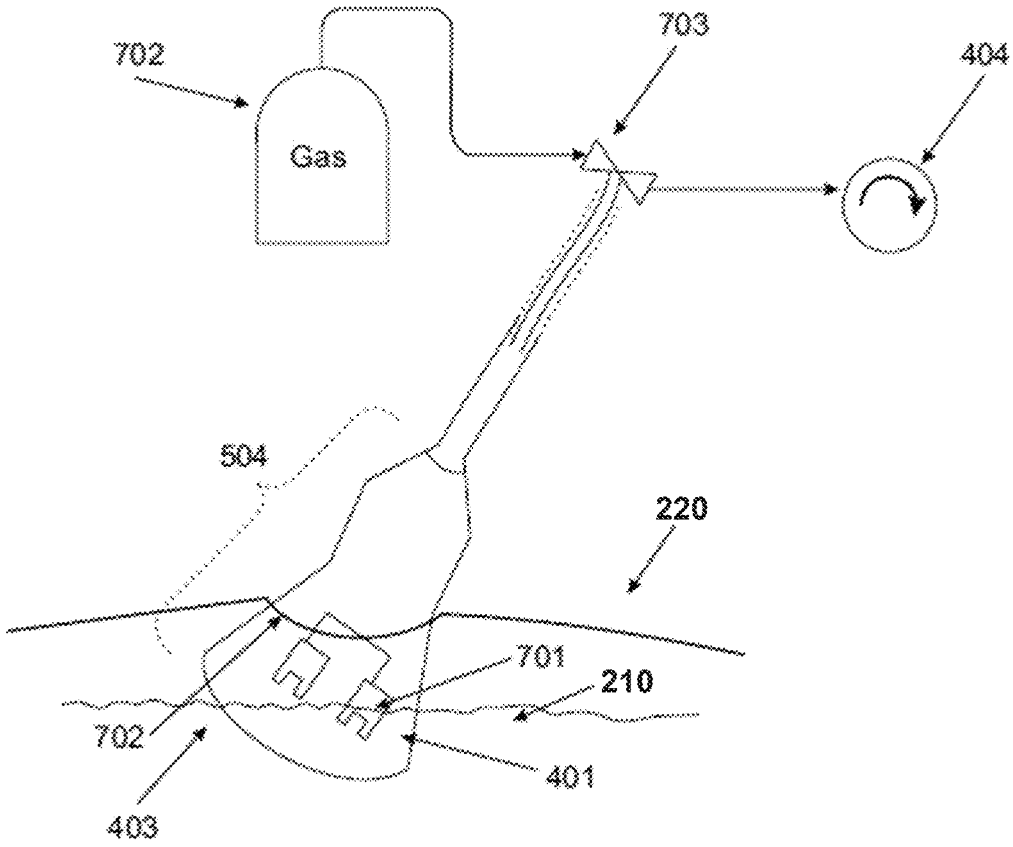
FIG. 7 is a simplified diagrammatic illustration of insertion of a low-mixing wine cleaning system into wine in a barrel, according to some embodiments of the invention.

Reference is now also made to FIG. 7, which shows details of a lower segment 504 of a wine cleaning system being inserted into a barrel 220, in accordance with some embodiments of the invention. For clarity, the locking mechanism, if any, is not shown, but it is noted that segment 504 may be inserted through the aperture in lock mechanism 570, after attachment thereof to barrel 220. A noted below, in some midpoints, lock mechanism 570 is attached only after the snout is inserted into the barrel.

In some embodiments, before insertion of inner apparatus 501 into the wine, a slow flow of gas 702 purges air from a cavity in the barrel 220 above the wine 210 and/or blankets the wine. Optionally, the flow is slow enough to avoid causing wine mixing.

Optionally, supplied gas 702 is an inert gas, such as argon, co2 or nitrogen. A potential advantage of blanketing the wine with an inert gas is preventing oxidation of the top surface layer of wine and of the first amount of wine extracted. Optionally, the gas is provided in a fixed amount, for example, 0.1-0.5 liters, for example, 0.25 liters. In some embodiments, a valve which releases a fixed amount of gas per operation is used. Alternatively a controller and/or flowmeter are used to control the amount of delivered gas.

In some embodiments, a slow flow of gas 702 is supplied to the wine 210.

Optionally, supplied gas 702 is an oxygenating gas such as filtered air. A potential advantage of supplying an oxygenating gas to the wine 210 is an ability to elevate oxygen levels in wine when necessary. Optionally, the oxygenating gas is supplied to a specific layer of wine, such as a middle layer 202. Optionally, an oxygen sensor (e.g., in the barrel or in the path of the extracted wine) monitors the oxygen level in the wine and a control unit controls supply of oxygenated gas in a closed loop. Optionally, the system oxygenates wine after a cleaning completion of a cleaning method, for example, as described herein.

In some embodiments, supply of gas 702 is conveyed through snout 401.

Optionally, supply of gas 702 is conveyed through extraction hose 502.

Optionally, a valve 703 controls connection of extraction hose 502 to gas supply or to an extraction pump 404. Optionally, valve 703 has two gas openings; for example, allowing selection of an inert gas supply or an oxygenating gas supply.

In some exemplary embodiments, snout 401 of inner apparatus 501 is inserted through an opening of the barrel 220, such as a bung hole 211, and into wine 210.

Optionally, snout 401 is made of a flexible, resilient material, such as silicone, in order to be temporarily folded or compressed, enabling entry into bung hole 211 that is smaller than a maximal snout diameter 403. Optionally, such compression reduces the snout maximal diameter by between 5% and 50%, for example, between 10% and 30%.

In some exemplary embodiments, upon insertion of inner apparatus 501, a sufficient volume of wine is extracted to prevent overflow of wine displaced by inner apparatus 501. Optionally, the volume of wine is equal or less than to the displacement volume of inner apparatus 501. Optionally, the volume of wine is 2 liters. Optionally, extraction is stopped when the volume is extracted. Optionally, extraction occurs only when snout 401 is adequately immersed. For example, extraction occurs only when snout opening 403 is fully immersed, potentially advantageous in preventing wine oxidation which might be caused by suctioning air with the extracted wine. An additional potential advantage is preventing splattering and wine loss accompanying extraction with a partially immersed snout opening 403.

Optionally, the initial removal of wine also removes material from the top surface of the wine collected by the snout, to the filtering system.

In some embodiments, lower segment 504 includes a liquid contact sensor 701. Liquid contact sensor 701 can be positioned at a level of lower segment 504 at which lower segment 504 is adequately immersed (e.g., and the inserted volume of apparatus 501 is not too large); for example, at which snout opening 403 is fully immersed. Optionally, liquid contact sensor 701 is positioned inside of snout 401.

Optionally, liquid contact sensor 701 reports to a control unit in a closed-loop; the control unit is discussed in further detail in this application.

Optionally, an extraction pump 404 drives the extraction. Optionally, the control unit activates extraction pump 404 in a closed loop. Optionally, the control unit activates extraction pump 404 only while liquid contact sensor 701 is in contact with wine 210 in barrel 220.

Optionally, during wine cleaning, when contact of liquid contact sensor 701 with wine is lost, the control unit deactivates extraction pump 404; for example, when inner apparatus 501 is removed after completion of cleaning. Optionally, upon loss of contact of liquid contact sensor 701 with wine, processing continues for wine that was transferred.

Figure 8:
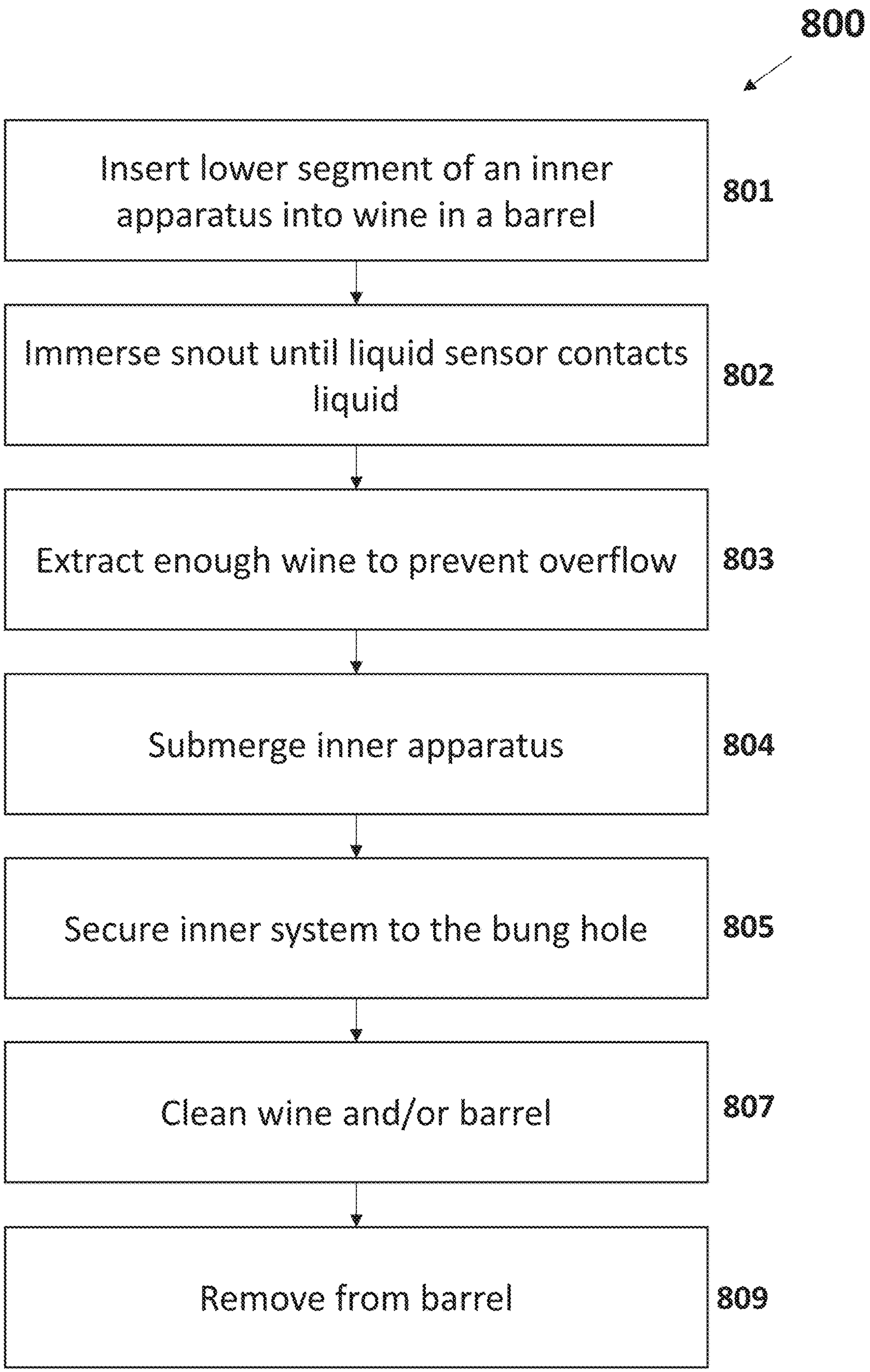
FIG. 8 is a flow chart of an exemplary method of installing an inner apparatus into a barrel containing wine, according to some embodiments of the invention.

Reference is now made to FIG. 8, which shows a flow chart 800 of a method of installing an inner apparatus of a wine processing system into a barrel containing wine, according to some embodiments of the present invention.

An inner apparatus is immersed into wine in a barrel (step 801). Optionally, the inner apparatus is inserted through a bung hole of the barrel. A snout of the inner apparatus can be folded and/or compressed, if its opening is larger than the bung hole. In some embodiments, gas is injected during and/or before such insertion, for example, as described herein.

In some exemplary embodiments of the invention, the inner apparatus is inserted until a wine sensor makes contact with the wine (step 802). Optionally wine is extracted (step 803) upon contact of the liquid contact sensor with wine, potentially preventing overflow of wine from the barrel by displacement of the inner apparatus when fully inserted; for example, the volume of the inner apparatus is extracted.

Optionally, the extraction of an overflow volume of wine is interrupted when contact between the liquid contact sensor and wine is lost and/or when a volume (e.g., depending on a known displacement of the inner apparatus) is removed.

Optionally, during installation, inner apparatus is submerged (step 804) until a sleeve of the upper segment of the inner apparatus reaches the bung hole (e.g., this may be done if insertion is before attaching lock mechanism 570). The sleeve is secured to the bung hole, holding the inner apparatus in place (step 805). Optionally, it is secured by a locking mechanism.

After insertion, the wine and/or barrel are cleaned (step 807) and/or otherwise processed.

After processing is completed, the inner apparatus is optionally slowly removed (step 809), optionally after removal of the locking mechanism. In some embodiments, the inner apparatus remains in the barrel for a later processing event, for example, after 1-5 hours, days or weeks, and/or longer.

Exemplary Wine Treatment System

Figure 9A:
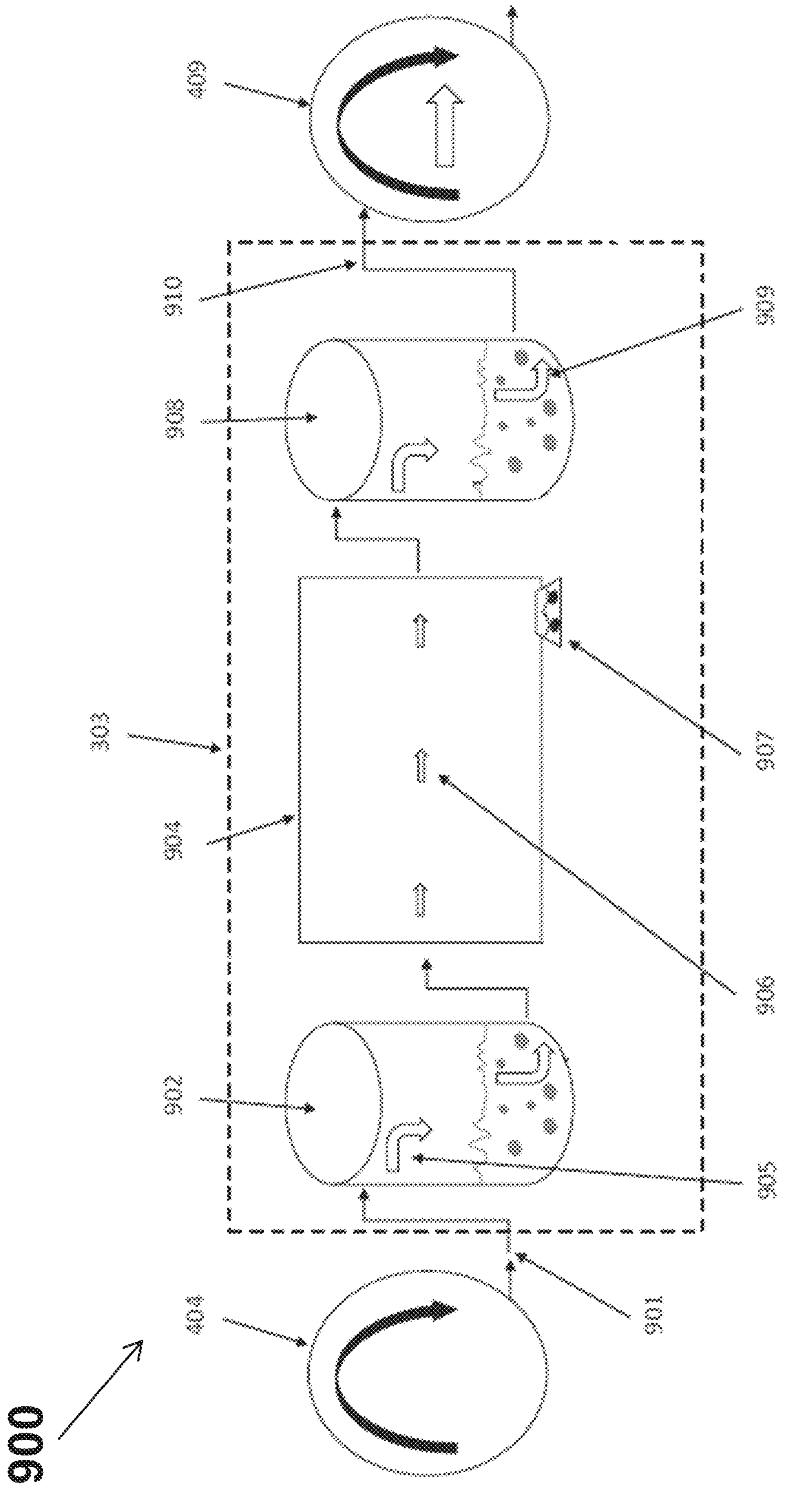
FIG. 9A is a schematic illustration of a wine filtering system, according to some embodiments of the invention.

Reference is now also made to FIG. 9A, showing a wine treatment system 900, receiving an input flow 905 and generating an output flow 909, according to some exemplary embodiments of the invention. In some exemplary embodiments of the invention, optional input and/or output reservoirs 902, 908 (respectively) are provided to buffer unequal flow rates of a treatment pump 904 and input and/or output flows 905 and 909. A potential advantage of the buffer reservoirs is enabling the extraction pump 404 and return pump 409 to be optimized at a flow rate consistent with low mixing, while a treatment pump 904 operates at its designed flow rate, which may be higher, for example, if a centrifugal filter is used. Optionally or alternatively, a cartridge filter is used. Optionally, the flow rates are adjusted according to a degree of clogging of the cartridge, which may be manually and/or automatically set.

It is noted that at a start of filtering the removed wine is laden with large and small particles, which tend to block filter media. This is a potential advantage of using centrifugal filtration. Another potential advantage of reduction of flavor adsorption by the filter media. Another potential advantage is the option of changing filtering parameter to match the turbidity and particle size of the wine. This may be useful for removal of particles of sizes of 10 microns, 5 microns and/or less.

The flow rates of the input flow 905 and of the output flow 909 need not be the same, for example, the flow rate of input flow 905 may be lower.

Optionally, wine collected in input reservoir 902 primes a treatment pump 904.

In some embodiments, the treatment system comprises a filtering system 303 and the treatment pump 904 is a filter pump. Optionally, input flow 905 is an output of an extraction pump 404 (or siphoning from) of a low-mixing exchange system 302.

Optionally, the output flow 909 is an input of a return pump 409 for a low-mixing exchange system 302. Optionally, filtering system 303 and low-mixing exchange system 302 comprise an in-place, low-mixing wine cleaning system 300 (or 520), for example, as described herein.

In some embodiments, an input reservoir 902 collects wine entering through a treatment system inlet 901. Optionally, input reservoir 902 contains one or more level sensors. Optionally, input reservoir level sensors report to a control unit that controls the wine cleaning system 300 in a closed loop.

In some embodiments, treatment pump 904 is a filter pump that filters debris from extracted wine. Optionally, treatment pump 904 includes a filter with an interposing medium, such as filter paper. Alternatively, treatment pump 904 is a type of filter pump that collects debris without use of an interposing medium. Non-use of an interposing medium offers a potential advantage of filtering not suffering from damage to wine taste and color and reduced filtering efficiency due to clogging of the interposing medium. Optionally, treatment pump 904 is a type of filter pump that collects debris in a debris cell 907. Optionally, treatment pump 904 is a centrifugal filter pump.

In some embodiments, treated wine is deposited into an output reservoir 908.

Optionally, output reservoir 908 contains one or more level sensors.

Optionally, output reservoir level sensors report to a control unit that controls the wine cleaning system 300 in a closed loop. Output reservoir 908 acts as a buffer, allowing a treatment pump 904's flow rate 906 and the rate of the output flow 909 to be unequal.

In some embodiments, wine exits output reservoir 908 through an outlet 910.

Optionally, wine deposited in output reservoir 908 primes a return pump 409.

Figure 9B:
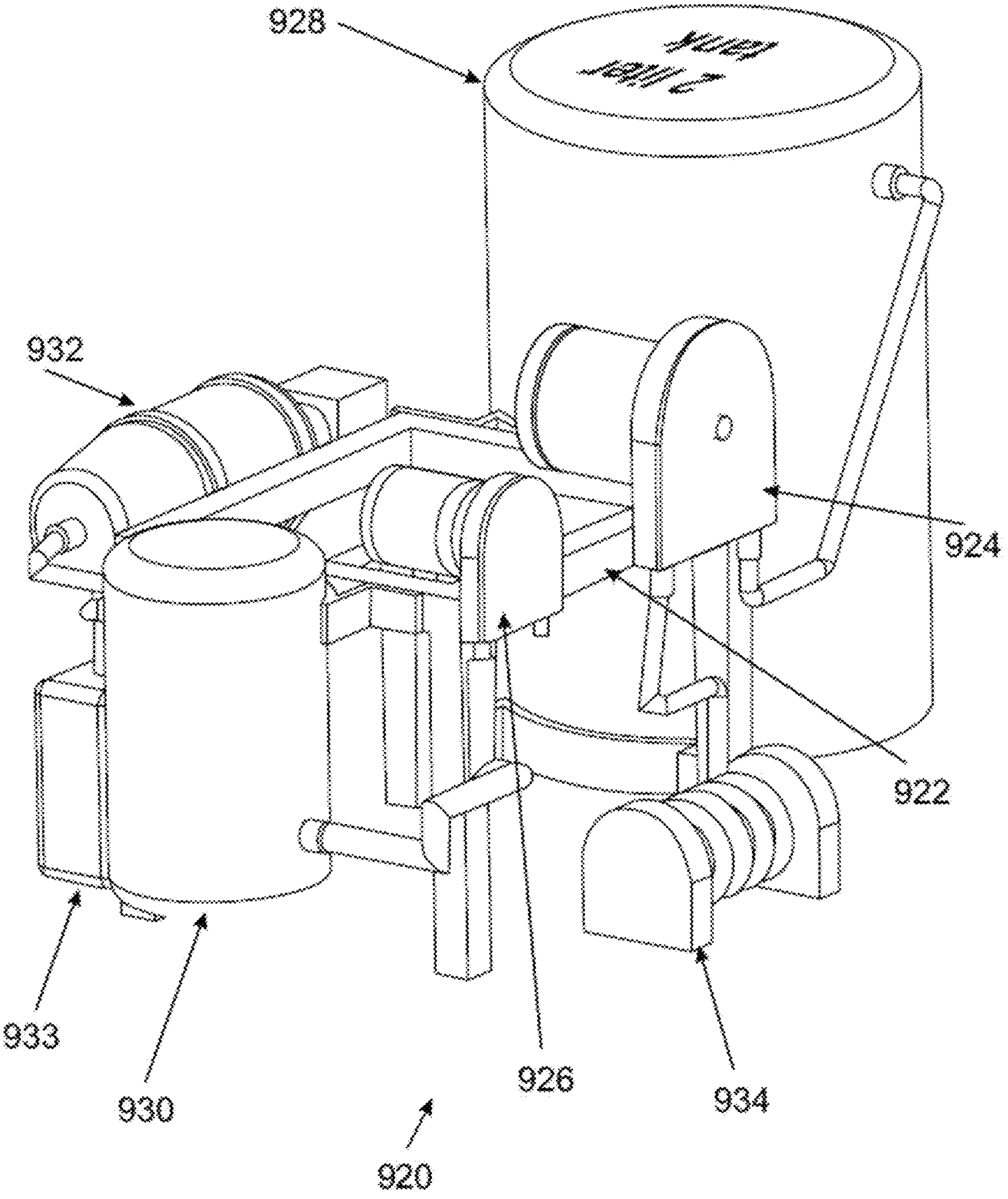
FIG. 9B is a perspective view simplified illustration of a wine filtering system, according to some embodiments of the invention.

FIG. 9B is a perspective view of a wine filtering system 920 which may be constructed in accordance with the description of FIG. 9A, according to some embodiments of the invention. An optional frame 922 is shown holding the various components.

Wine is pumped by a peristaltic pump 924 from an input hose and into a dirty wine holding tank 928. A centrifugal filtering pump 932 draws wine from tank 928 and filters the wine, depositing the filtered wine in a storage 930, with extracted debris optionally held in a holding cell 933.

A second peristaltic pump, optionally low pressure pump 926 (e.g., taking advantage of the filter pump output pressure) returns the filtered wine form storage tank 930 towards the barrel.

The hose (e.g., two hoses, one for extraction and one for return) are optionally rolled on a hose reel 934.

Figure 10:
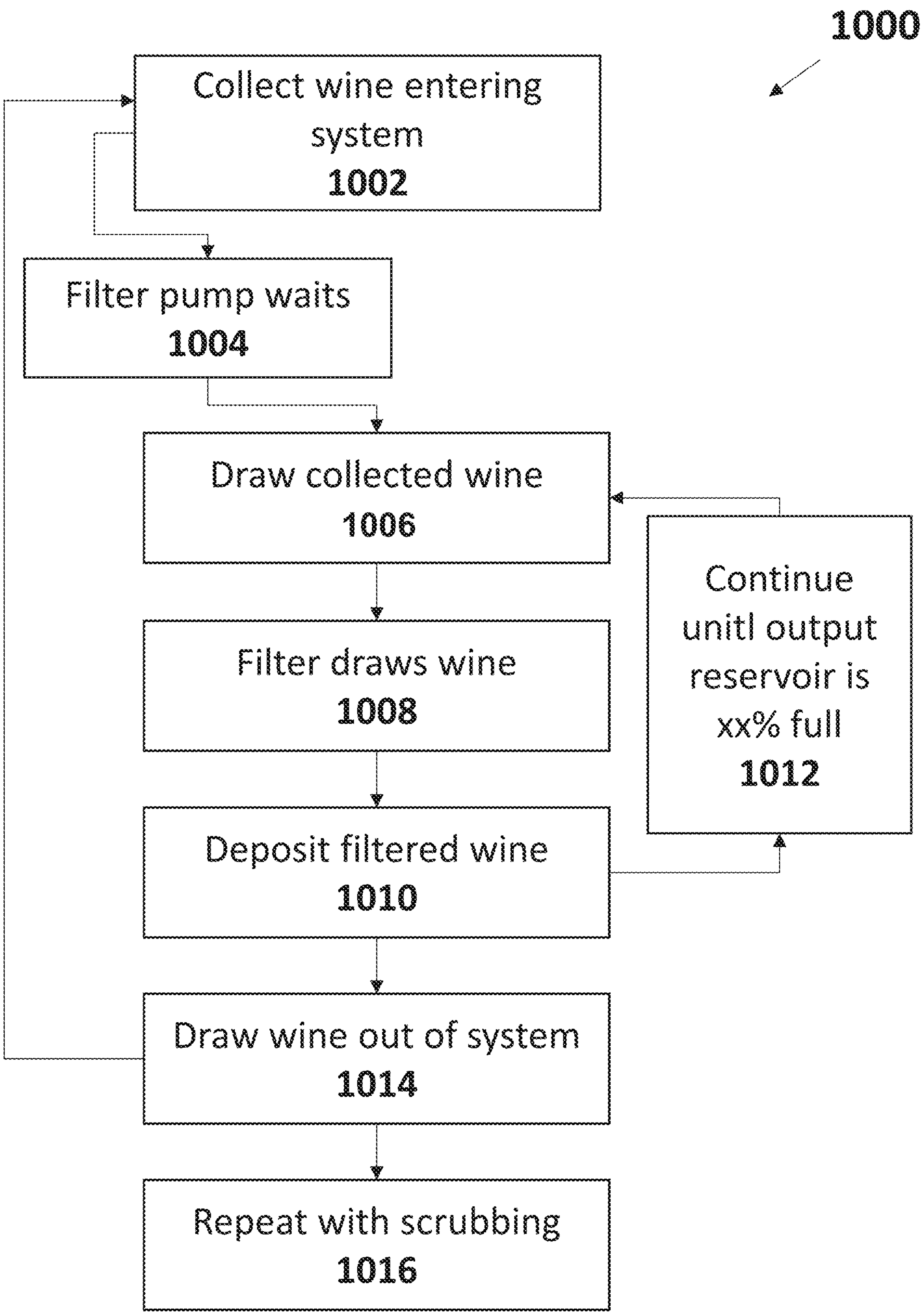
FIG. 10 is a flow chart of an exemplary method for filtering wine, according to some embodiments of the invention.

Reference is now made to FIG. 10, showing a method 1000 of filtering wine while buffering flows of input, filtering, and output, according to some exemplary embodiments of the present invention.

In some embodiments, an input reservoir collects wine entering the filtering system (step 1002). Optionally, an extraction pump, external to filtering system, pumps wine into the filtering system. Optionally, the extraction pump is part of a low-mixing exchange system 302, discussed in further detail in this application. As noted above, an initial extraction of wine may occur during insertion of snout 401 into the barrel.

In some embodiments, a filter pump waits to begin drawing of wine from the input reservoir (step 1004). Optionally, the filter pump waits until the input reservoir is full.

Optionally, the input reservoir is sized according to a desired amount of wine extraction, for example, 1, 2, 3 liters or intermediate volumes. Alternatively, the filter pump waits until an input flow has terminated; for example, a turbidity sensor reading measures clean wine, e.g. measured turbidity is below a requisite level, indicating that a sediment-laden layer of wine from the bottom of a barrel has been transferred to the input reservoir. Alternatively, the filter pump waits until the input reservoir reaches a specified level; for example, 50% full. After waiting, the filter pump draws wine from the input reservoir (step 1006).

In some embodiments, the wine drawn from the input reservoir is filtered (step 1008) and deposited into an output reservoir (step 1010). Optionally, wine drawing (step 1006), filtering (step 1008), and depositing (step 1010) continue (step 1012) until the output reservoir is, for example, 80% full. As noted, the duration of stay in the centrifugal pump may depend on the wine turbidity and/or other wine parameters. Optionally, a sensor on the output from the pump helps decide a needed duration of stay, optionally based on a pre-set and/or user entered desired NTU or other target variable.

In some embodiments, wine is drawn (step 1014) from the output reservoir when it fills. In some embodiments the drawing is synchronized. In some embodiments, however, drawing is asynchronous e.g., drawing is when the output reservoir fills and/or when cleaning is completed. Similarly, wine extraction may be asynchronous and continue until the storage tank is full and/or clean wine is detected and/or the cleaning process is completed.

Optionally, a return pump, external to the filtering system, draws wine from the filtering system. Optionally, the return pump is part of a low-mixing exchange system 302, discussed in further detail in this application.

Optionally, after the wine is cleaned, the barrel bottom is scrubbed (step 1016) such scrubbing may also include extracting wine with the product of scrubbing. A two step operation may be useful to prevent the movements associated with the scrubbing from causing dispersion of sediments. Optionally or alternatively, also cleaning involves lateral movement of snout 401 (for example as described below).

Alternatively, at least some scrubbing may be carried out without completing removal of the sedimented wine, for example, a single operation of filtering and scrubbing may be carried out.

In some exemplary embodiments of the invention, the amount of wine extracted during scrubbing is between 1 and 20 liters, for example, between 8 and 12 liters. Optionally, scrubbing includes scanning between 20 and 80% of a bottom of the barrel. Optionally, scrubbing continues for between 6 and 15 minutes, for example, about 10 minutes. Optionally, initial sediment removal takes between 0.2 and 5 minutes, for example, between 0.8 and 3 minutes.

Optionally or alternatively, scrubbing and wine cleaning are performed at each of several locations in the barrel bottom, for example, before snout 401 is moved.

In some embodiments, the system is treated periodically and/or between barrels and/or between wine types and/or as needed. For example, the system may be flushed with water or water with SO2 and/or sediments may be removed from the filter and/or filter medium replaced. Optionally, a fill indicator is provided in a particle collection compartment of the filter.

Optionally, the system is filled with an inert gas after use.

Barrel Interior Surface Treatment

Figure 11:
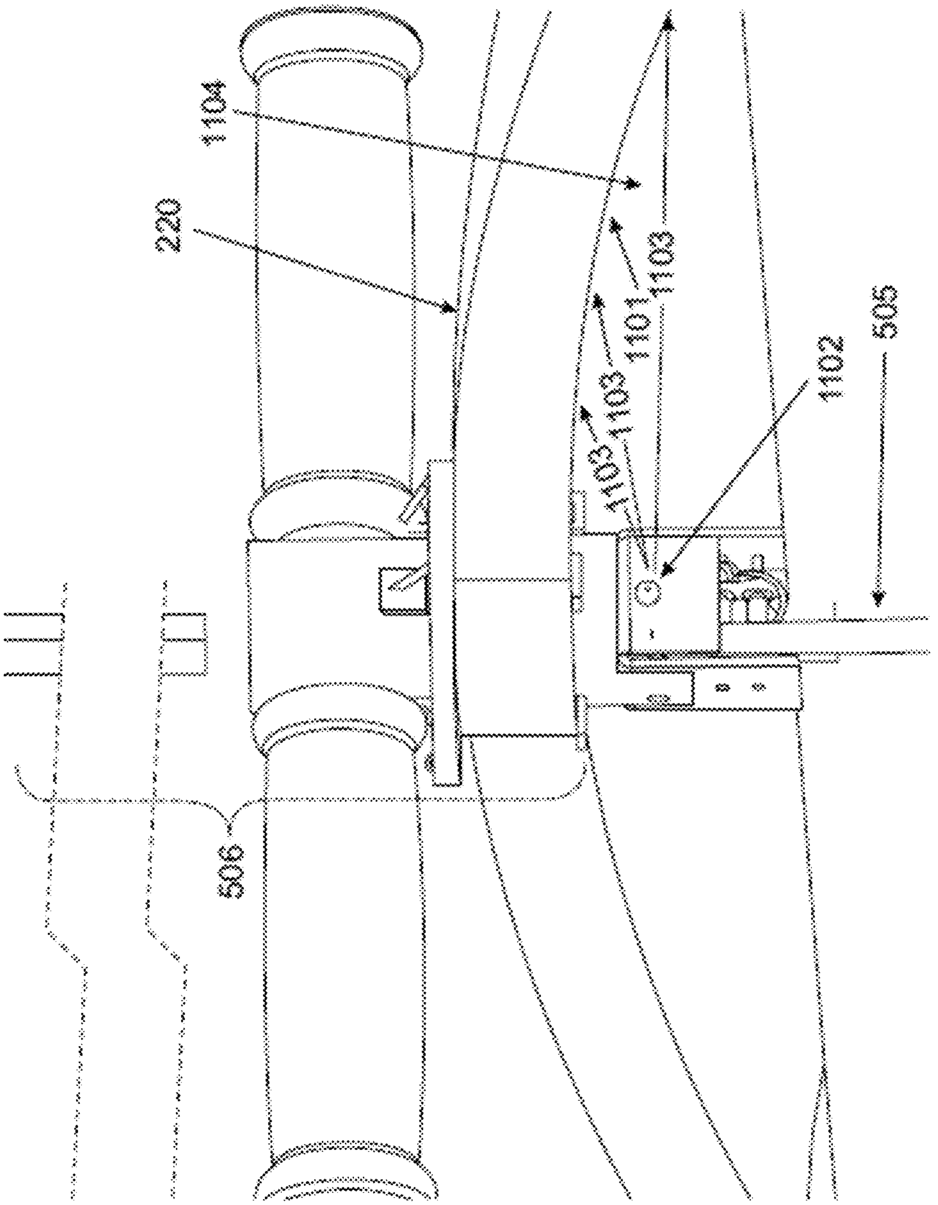
FIG. 11 is a side view simplified illustration of an upper segment with an UV sterilization light source for disinfecting an inside surface of a wine barrel, according to some embodiments of the invention.

Reference is now also made to FIG. 11, which shows an energy source treating an interior surface of a wine barrel 220, according to some embodiments of the present invention. Optionally, region 1101 is alongside a cavity 1104 in barrel 220 that is empty of wine.

Optionally, the energy source(s) are in an upper segment 506 that is part of a wine cleaning system's 300 internal apparatus 501. Cavity 1104 is present periodically during a wine cleaning method. Optionally, the energy source(s) are disposed inside of cavity 1104.

In some embodiments, the energy source(s) are one or more UV sterilization light sources 1102. UV radiation 1103 from UV sterilization light source(s) 1102 disinfects inside surface 1101. Optionally, there are two UV sterilization light sources 1102. Each UV sterilization source is optionally on opposite sides of upper segment 506. Optionally, the UV light is aimed generally upwards towards the vault of the barrel, for example, near the bung-hole, for example, at a radius of between 5 and 20 cm therefrom, for example, between 9 and 12 cm therefrom. Optionally, this corresponds to areas exposed due to natural receding of wine level. Optionally, aiming is using one or more of a lens, a beam shaper, a mirror and/or other light manipulating elements and/or a light blocking element. Optionally or alternatively, the light source is directional and appropriately aimed.

Optionally, UV sterilization light sources 1102 are turned off when not in a cavity.

In some exemplary embodiments of the invention, UV sterilization is applied continuously. In some embodiments, UV sterilization is applied when the wine is at its lowest or near its lowest level, for example, when both the intake and outflow buffers are full. For example, at this point, between 1 and 6 liters of wine may have been removed.

Barrel Scrubbing

Figure 12:
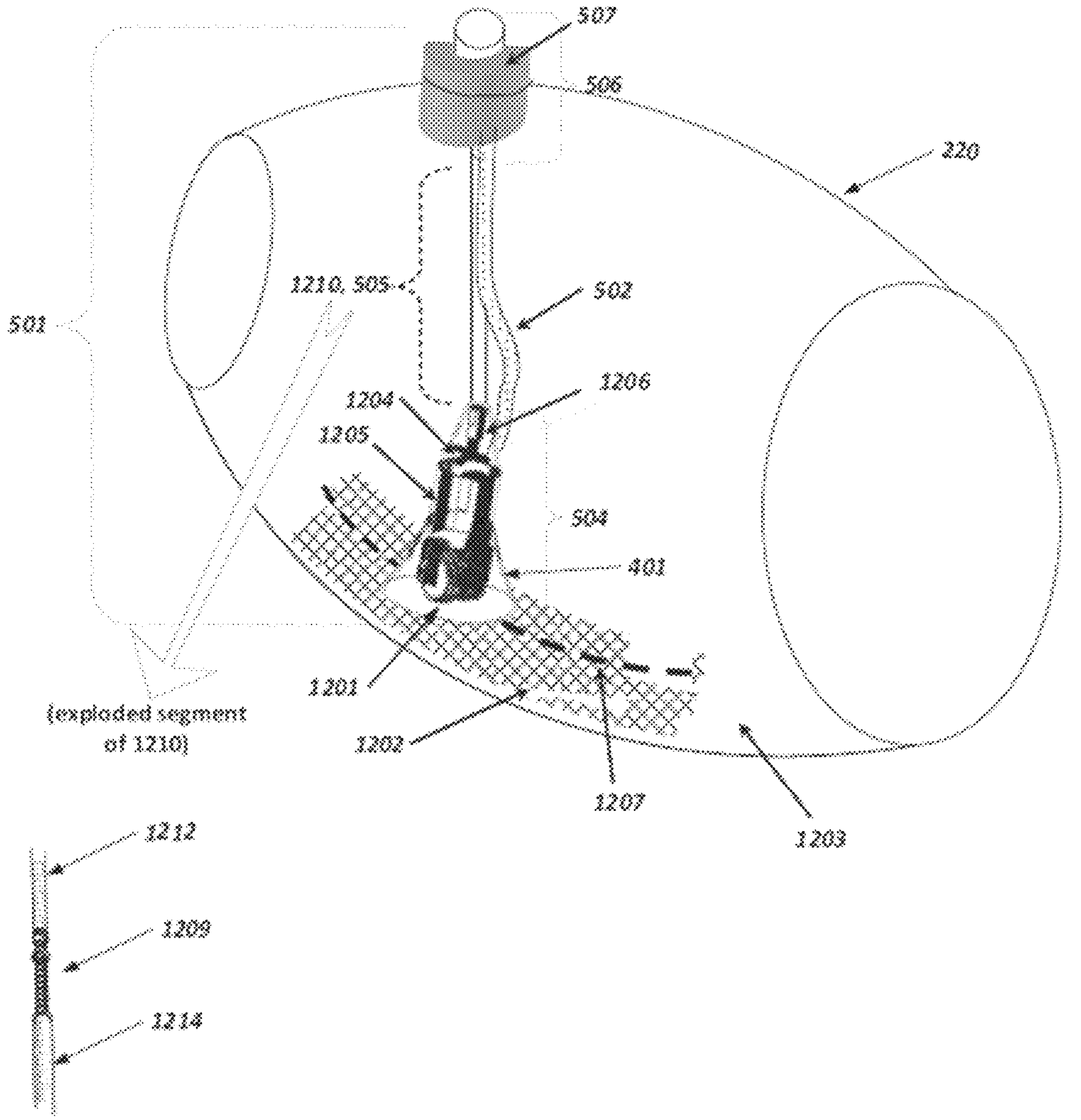
FIG. 12 is a perspective view simplified illustration of a system for cleaning an interior surface of a barrel, according to some embodiments of the invention.

Reference is now also made to FIG. 12, showing a scrubbing element 1201 disposed inside a wine barrel 220 that scrubs encrusted matter off an interior surface 1203 barrel 220, according to some exemplary embodiments of the invention.

It is noted that in some types of wine the encrustations block the flavor mediating properties of the barrel wall from acting on the wine and/or may have other effects (e.g., chemical) on wine quality. In some types of wine the encrustation may support growth of desirable or undesirable microorganisms and/or have other effect on biological processing of the wine. The effect of the encrustations on the particular wine and/or its history and/or aging status may affect the amount (e.g., volume) and/or area to be treated by encrustation removal.

Optionally, scrubbing is carried out after sedimented wine is removed and filtered. Such removal may be carried out without moving snout 401 laterally. In some exemplary embodiments of the invention, scrubbing does include moving scrubbing element 1201 (optionally with and while it is inside snout 401). In some embodiments, the movement mechanism described herein is used also during sediment removal, for example, to scan a same sized or smaller region of the barrel bottom.

In some exemplary embodiments of the invention, moving of snout 401 is provided by rotation of the scrubbing element against the barrel bottom and control of such movement is provided by upper mechanism 526, for example, as described herein. In other embodiments, both motive power and control are provided by upper mechanism 526.

Optionally scrubbing element 1201 is transported over an arc 1207 along inside surface 1203 of barrel 220. Scrubbing element 1201 thereby scrubs over a distance along an encrusted surface 1202 of the inside surface of the barrel.

In some exemplary embodiments of the invention, element 1201 (and snout 401) scan the barrel in a series of parallel strips, changing direction when reaching the end of a scanned region. Optionally, the strips overlap, for example, between 10% and 80%. Alternatively, the strips are spaced form each other. In some embodiments, at least part of the barrel bottom is scanned and scrubbed at least twice, in separate scans, in a same cleaning session. Optionally, a sediment removal step and/or a settling step (e.g., waiting) are applied between repeats.

Optionally, a suspended swinging member 1210 holding the scrubbing element transports the scrubbing element. Optionally, swinging member 1210 applies a lateral force on scrubbing element 1201, with a vertical force being applied by rod 505. A potential advantage of applying a force on scrubbing element 1201 is maintaining contact between scrubbing element 1201 and inside surface 1203 during transport of scrubbing element 1201.

In some exemplary embodiments of the invention, rod 505 comprises two tubes 1212 and 1214, one within the other and interconnected by a spring 1209 which tends to push them apart. O-rings may be used to seal between the tubes. Optionally or alternatively, other telescoping self-lengthening designs may be used.

A potential advantage of a spring supplying the force is that the spring adjusts the length of swinging member 1210 to match changes in distance to interior surface 1203 during swinging.

In some embodiments, scrubbing element 1201 is a rotating brush. Optionally, a scrubbing motor 1205 rotates the scrubbing element 1201. Optionally, element 1201 is collapsible, for example, for insertion. Optionally or alternatively, element 1201, or portion thereof that contact the barrel are softer than the barrel materials (e.g., wood) so as to reduce damage thereto.

It is a particular feature of some embodiments of the invention that barrel 220 contains wine 210 (e.g., at least 50% full) during scrubbing off of encrusted matter.

Optionally, scrubbing element is disposed in a snout 401 of a low-mixing wine cleaning system 300. Optionally, low-mixing wine cleaning system 300 cleans wine containing scrubbed encrusted matter. Optionally, snout 401 prevents encrusted matter from escaping into nearby wine.

In some exemplary embodiments of the invention, turbidity sensor 546 is used to detect an amount of matter removed by scrubbing, possibly indicating when scrubbing is completed.

Optionally, one or more moving knife blades 1204 chop large pieces of loosened encrusted matter into finer particles A potential advantage of chopping encrusted matter is to prevent an extraction hose 502 from getting clogged.

Optionally, a knife blade motor 1206 moves knife blades 1204.

In some exemplary embodiments of the invention, scrubbing is blind.

Alternatively, scrubbing uses a turbidity sensor to estimate the amount of removed material and thus the amount of existing material. Optionally, a small area (or the entire area to be scrubbed bottom in a first scan) is scrubbed and based on the turbidity of the removed wine, an estimate of one or more scrubbing parameters is made (e.g., % of area to scrub, number of repeats, speed of scrubber).

Figure 13:
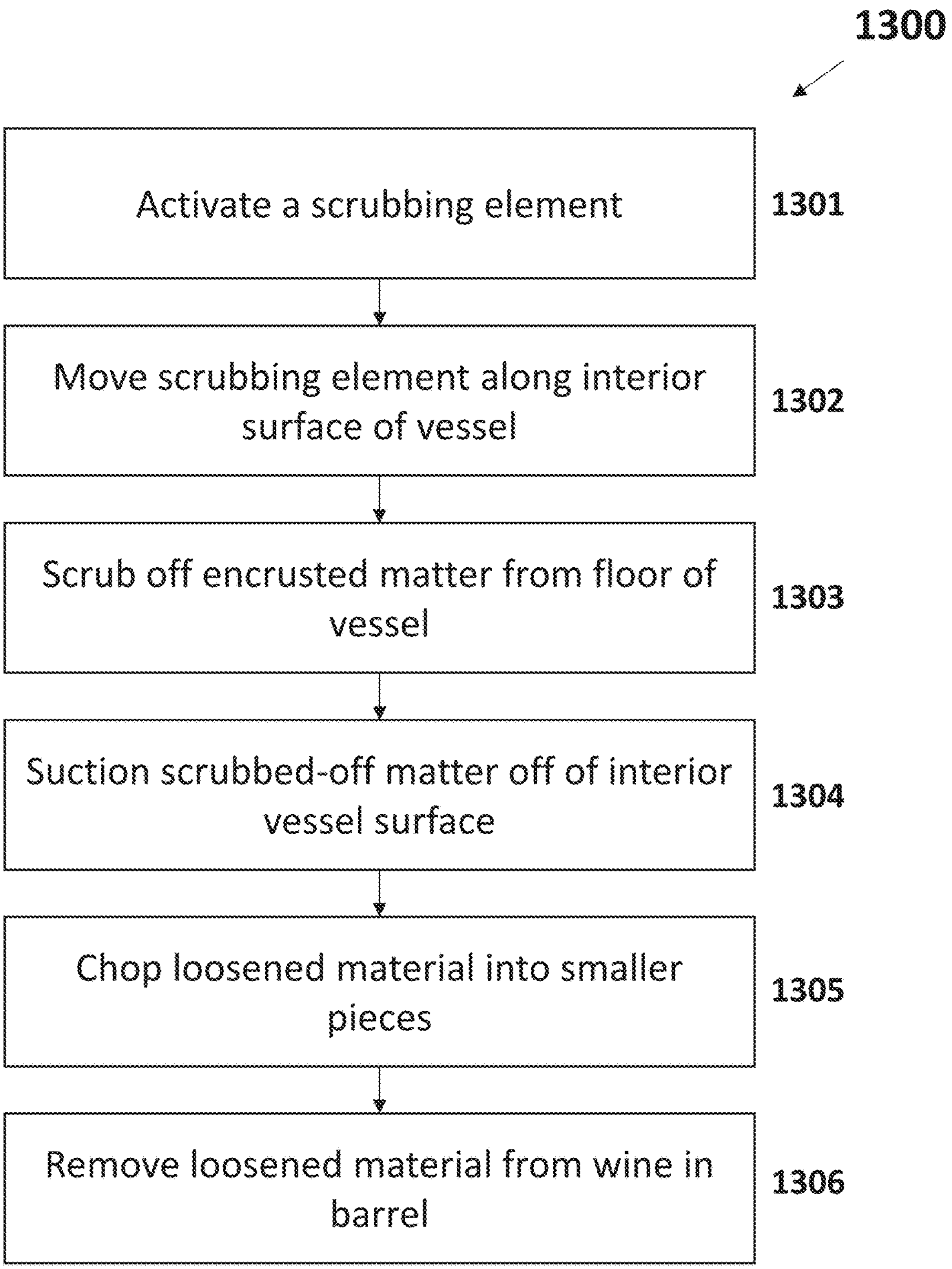
FIG. 13 is a flow chart of an exemplary method for cleaning the interior surface of a barrel, according to some embodiments of the invention.

Reference is now made to FIG. 13, showing a flow chart of a method for cleaning an interior surface of a barrel 1300, according to some embodiments of the invention. Optionally, the method 1300 occurs after a wine cleaning method. Optionally, the method 1300 occurs after a wine cleaning method has extracted and filtered a layer of sediment. A scrubbing element is activated (step 1301). Optionally, the scrubbing element is rotated by a motor. The activated scrubbing element can be moved along the interior surface of the barrel (step 1302), in order to cover an area of the barrel. Encrusted matter can be scrubbed off the interior surface of the barrel (step 1303) by the scrubbing element. Scrubbed-off encrusted matter can be suctioned off an interior surface of the barrel (step 1304). Optionally, scrubbed-off encrusted matter is chopped into smaller pieces 1305, for example, so as not to clog an extraction tube. Optionally, encrusted matter is removed from within wine in the barrel (step 1306). Optionally, encrusted matter is removed from the barrel by cleaning wine in the barrel with other remaining particles, if present. Optionally, cleaning the wine to remove encrusted matter is done using one or more embodiments of the present invention.

In some exemplary embodiments of the invention, the scrubber moves at a low speed, for example, between 1 and 10 cm/second, for example, about 7 cm/sec.

In some exemplary embodiments of the invention, the rotation of scrubbing elements 1201 is low, for example, fewer than 60, 30, 20, 10, 5 or intermediate number of rotations per second.

In some exemplary embodiments of the invention, different repeats of scrubbing have different parameters, such as one or more of scrubber speed, scan speed, scan shape and/or scan alignment.

Exemplary Swing-Drive Mechanism

Figure 14A:
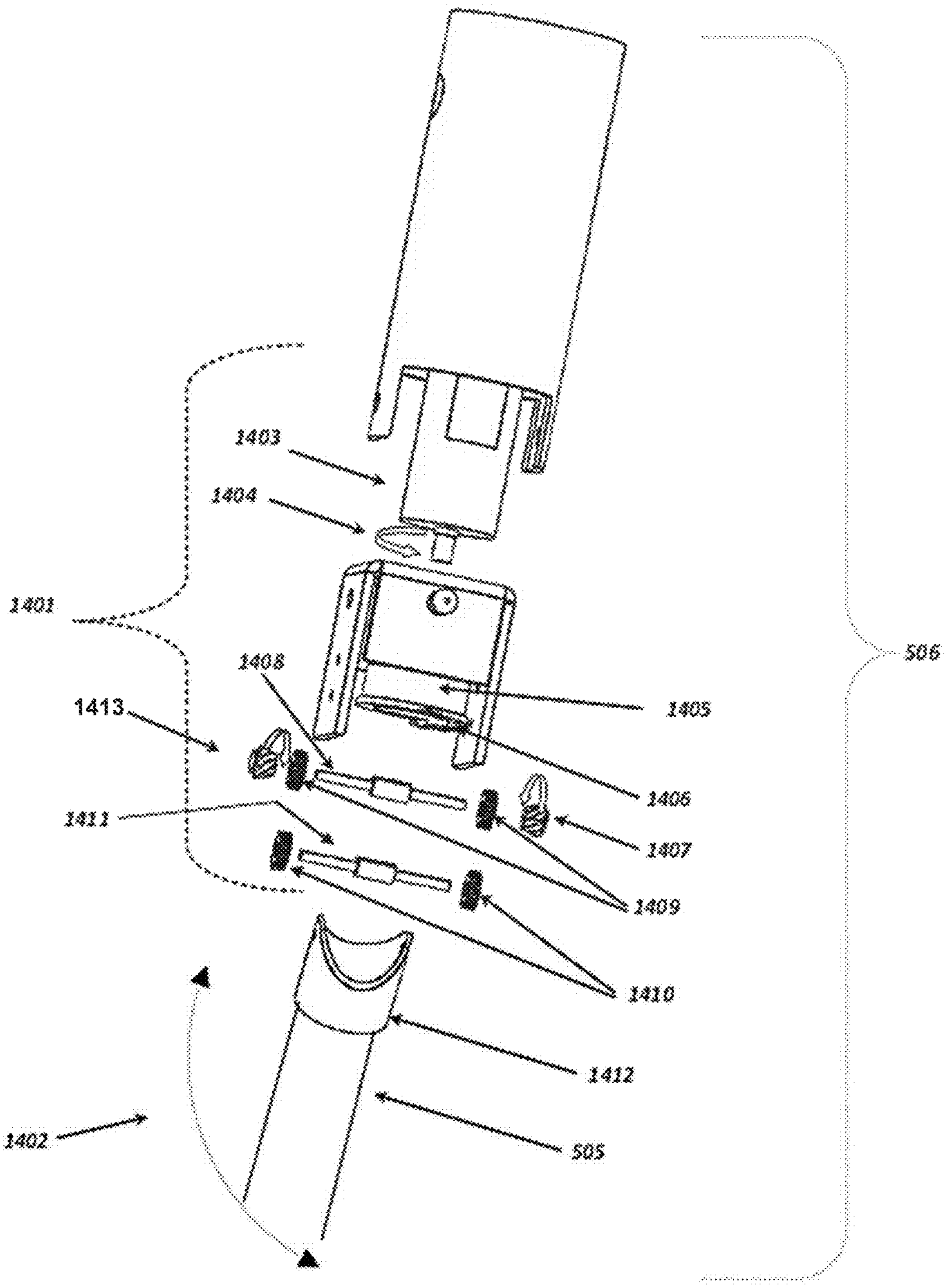
FIG. 14A is an exploded view simplified illustration of a swing-drive mechanism, according to some embodiments of the invention.

Reference is now made to FIGS. 14A, 14B, 14C and 14D, which are a side view and exploded view simplified illustrations of a wine filtering system in accordance to some embodiments of the invention. FIG. 14A, showing an exploded view of a swing-drive mechanism 1401, according to some embodiments of the present invention.

Optionally, swing-drive mechanism 1401 is employed to swing a supporting member 505 of a scrubbing element 542. Optionally, swing-drive mechanism 1401 is employed to swing snout 540 and scrubbing element 542.

In some exemplary embodiments of the invention, motive force is provided by scrubbing elements 542/1201 rotating against the barrel bottom and control by mechanism 1401, for example, by mechanism 1401 constraining the movement of rod 505 and snout 401 to follow a desired path.

In other embodiments of the invention, motive power is provided by mechanism 1401 and this may cause rotating scrubbers 542 to slip (and scrape) against the barrel bottom, if there rotational vector is different from that provided by mechanism 1401, this may be desirable in some embodiments.

Optionally, swing-drive mechanism 1401 produces bi-directional swinging 1402 from single-direction rotation, for example, using the following mechanism, which allows a single motor to cause snout 401 to scan the bottom of the barrel.

Optionally, swing-drive motor 1403 drives single-direction rotation 1404 of an upper gear 1405 that has teeth along a toothed arc 1406. Optionally, toothed arc 1406 alternately engages and rotates a first 1406 and second 1407 pinion gear, which can be bevel gears. Optionally, consecutive engagements of first 1406 and second 1407 pinion gears by toothed arc 1406 rotates first 1413 and second 1407 pinion gears in opposite directions. Optionally, consecutive alternate engagements by toothed arc 1406 of first 1413 and second 1407 pinion gears cause extension rod 505 to swing in opposite directions 1402. Optionally, alternate consecutive engagements by toothed arc 1406 of a first 1413 and second 1407 pinion gear rotate a transfer shaft 1408, to which one or more transfer gears 1409 are joined, in opposite directions. Optionally, opposite rotations of transfer shaft 1408 rotate transfer gears 1409, which are joined to transfer shaft 1408, in opposite directions. Optionally, opposite rotations of transfer gears 1409 rotate swing gears 1410, with which transfer gears are meshed, in opposite directions. Optionally, opposite rotations of swing gears 1410 rotate a swing shaft 1411, to which swing gears 1410 are joined. Optionally, a first of two opposite rotations of swing shaft 1411 cause extension rod 505, which is attached to swing shaft 1411 either directly or by a connecting element 1412, to swing from its equilibrium orientation. Optionally, upon disengagement of toothed arc 1406 from first pinion gear 1413, extension rod 505 is free to swing back to its equilibrium orientation. Optionally, a rotation speed of swing-drive motor 1403 is timed so that toothed arc 1406 reaches second pinion gear 1407 when extension rod 505 is substantially in its equilibrium orientation. Optionally, while swing-drive motor 1403 continues to rotate, extension rod 505 continues to swing.

Exemplary Optional in-Barrel Portion Driving Assembly

Figure 14B:
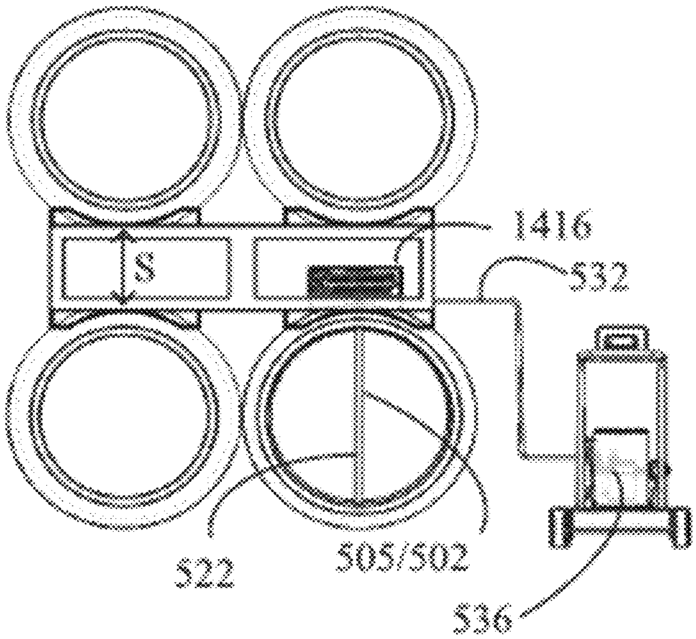
FIGS. 14B and 14C are side view simplified illustrations of a wine cleaning systems in accordance with some embodiments of the invention.

As shown in FIG. 14B, which is a side view simplified illustration of a wine cleaning system in accordance with the invention, space between respective layers of wine barrels may be quite limited. Most barrel racks allow 15-20 cm space(S) between the respective layers of barrels providing limited access to a wine barrel bung hole, let alone inserting a cleaning head assembly into the barrel.

In an exemplary embodiment of the invention depicted in FIG. 14B a driving assembly 1416 is sized to fit over a bung hole of a barrel between respective layers of barrels. In some embodiments, driving assembly 1416 is a low profile driving system. In some embodiments, driving assembly 1416 is coupled to and drives in-barrel portion 522. In the exemplary embodiment depicted in FIG. 14B, a rod 505 of in-barrel portion 522 is, for example, an integral rod.

Figure 14C:
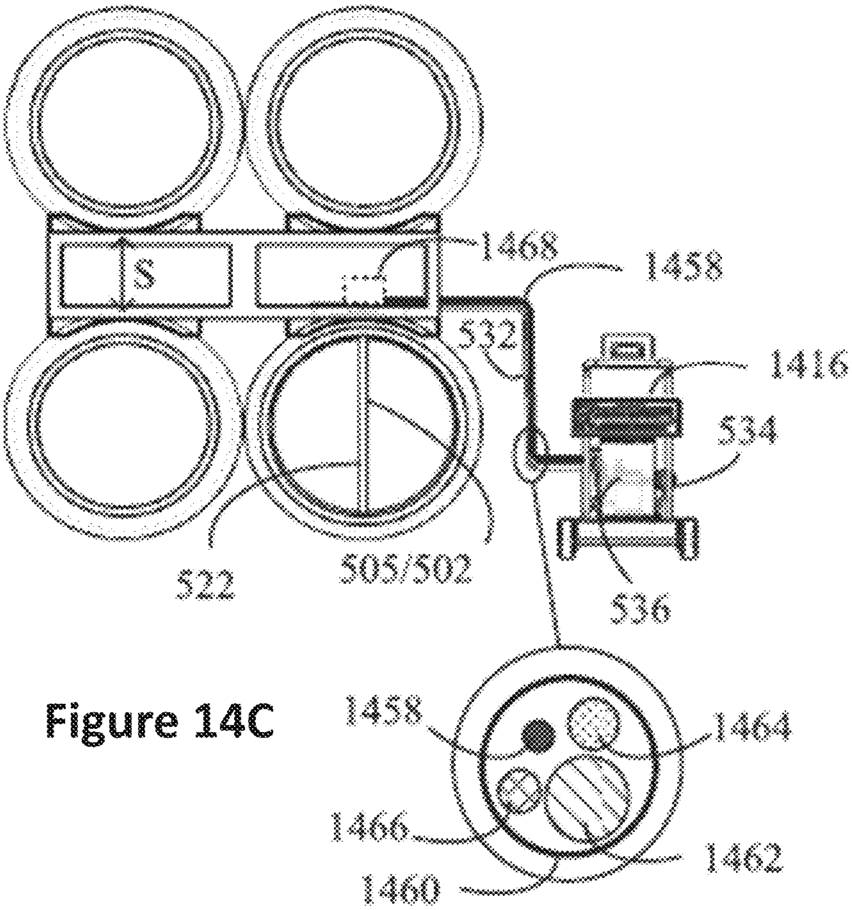

Optionally, and as shown in FIG. 14C, which is a side view and cross-section view simplified illustration of an aging wine barrel cleaning system for cleaning wine and/or treating a containing barrel in accordance with some embodiments of the invention, driving assembly 1416 of a wine barrel cleaning system is placed on outer system portion 534. In some embodiments, a driver cable 1458 connects driving assembly 1416 and in-barrel portion 522. In some embodiments, cable 1458 is a flexible rotatable driver cable. In some embodiments, a harness 1460 connects outer system portion 534 and in-barrel portion 522. In some embodiments, harness 1460 includes at least one of a liquid withdrawal conduit 1462, a power cable 1464 supplying power to at least sensors 546/701 and/or UV sterilization light sources 1102/599, a data input/output cable 1466 and a flexible rotatable driver cable 1458.

Optionally, in some embodiments, a gearbox 1468 is placed over a bung hole of a barrel and transfers and/or converts mechanical movement from flexible rotatable driver cable 1458 to in-barrel portion 522. In some embodiments, the gearbox is pneumatically or hydraulically driven. In some embodiments, hydraulic and/or pneumatic generators (not shown) on outer system portion 534 supply hydraulic and/or pneumatic pressure via one or more hydraulic/pneumatic hoses to gearbox 1468. In some embodiments, hydraulic and/or pneumatic generators (not shown) power pumps (e.g., extraction pump 404, return pump, filter pumps and others). In some embodiments, outer system portion 534 includes gas and oil reservoirs that supply the hydraulic and/or pneumatic generators. In some embodiments, harness 1460 includes tubes that provide hydraulic and/or pneumatic pressure directly to scrubbers 542.

Figure 14D:
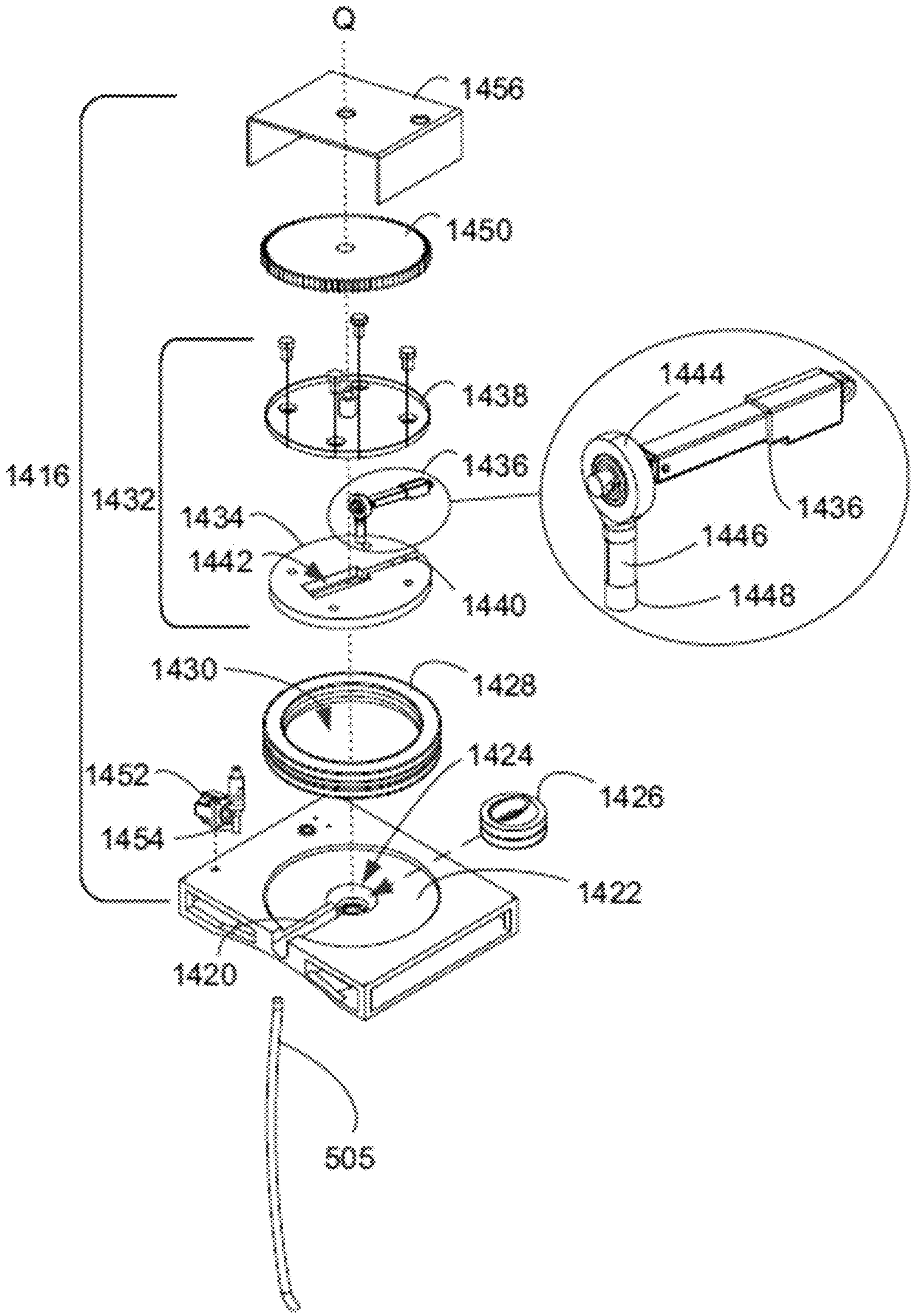
FIG. 14D is an exploded view simplified illustration of an exemplary embodiment of an in-barrel-portion driving assembly in accordance with the invention.

Reference is now made to FIG. 14D, which is an exploded view simplified illustration of an exemplary embodiment of an in-barrel portion driving assembly 1416 in accordance with the invention. In the exemplary embodiment of FIG. 14D, driving assembly 1416 rotates in-barrel portion 522. In some embodiments, driving assembly 1416 moves in-barrel portion 522 in a pendulous motion. In some embodiments, driving assembly 1416 combines rotational and pendulous movement of in-barrel portion 522.

In some embodiments, driving assembly is supported by a frame. In some embodiments, frame is sized and shaped to fit on top of a wine barrel. In some embodiments, a portion of frame 1418 resting on a barrel is concave. In some embodiments, at least a portion of frame 1418 includes openings, grooves, notches, holes and other geometrically shaped recesses and protrusions. In some embodiments, frame 1418 includes one or more first grooves 1420 cut out along one or more radii of a shallow recess 1422. In some embodiments recess 1422 is round. In some embodiments, recess 1422 includes an aperture 1424 in the center thereof sized to generally correspond to and be aligned with a bung hole of a barrel. In some embodiments, aperture 1424 houses a first bearing 1426, for example, a hollow pivot ball bearing. In some embodiments, first ball bearing 1426 is partially disposed inside a bung hole.

In some embodiments, one or more first grooves 1420 accommodate tubes, for example one or more bendable and/or flexible tubes 532 (FIG. 14B). In some embodiments, recess 1422 accommodates a second bearing 1428, for example, an axial ball bearing concentrically aligned with aperture 1424. In some embodiments second axial ball bearing 1428 rotates about an opening 1430 in bearing 1428.

In some embodiments, driving assembly 1416 includes at least one linear movement assembly 1432. In some embodiments, linear movement assembly 1432 includes at least a base 1434, a linear actuator 1436 and a cover 1438. In some embodiments, linear movement assembly 1432 is a pendulous movement assembly. In some embodiments, linear movement assembly 1432 is round. In some embodiments, linear movement assembly 1432 concentrically rests on top of second axial bearing 1428. In some embodiments, linear movement assembly 1432 rotates in concert with a rotating second axial bearing 1428. In some embodiments, linear movement assembly 1432 rotates about an axis (Q) aligned with a bung hole.

In the exemplary embodiment depicted in FIG. 14D, linear movement assembly 1432 base 1434 includes one or more second grooves 1440 cut out radially inwardly along one or more radii of base 1434. In some embodiments, as it approaches axis (Q) of base 1434 second groove 1440 opens to an elongated cutout 1442. Elongated cutout 1442 is in continuum to second groove 1440, beyond axis (Q).

In an exemplary embodiment, second groove 1440 accommodates one or more linear actuators 1436. In some embodiments, linear actuators 1436 is attached at a first end thereof to second groove 1440 at a peripheral location thereof and at a second end to a rod-end ball joint 1444. In some embodiments, linear actuator 1436 moves rod-end ball joint 1444 axially back and forth. In some embodiments, when linear actuator 1436 rests in second groove 1440, rod-end ball joint 1444 is disposed within elongated cutout 1442, free to move axially back and forth along the cutout.

In some embodiments, rod-end 1446 of rod-end ball joint 1444 includes a connector 1448 sized and shaped to connect to in-barrel portion 522. In some embodiments, cover 1438 rests on base 1434 sandwiching one or more linear actuators 1436 in between. In an exemplary embodiment, a first cog 1450 rests concentrically aligned with axis (Q) on cover 1438 of linear movement assembly 1432. In some embodiments, first cog 1450 rotates about axis (Q).

In the exemplary embodiment shown in FIG. 14C, a motor 1452 is mounted on frame. In some embodiments, motor 1452 includes a second cog 1454 in contact with first cog 1450. In some embodiments, rotation of first cog 1450 rotatingly drives linear movement assembly 1432 and linear actuator 1436 therewithin about axis (Q). In some embodiments, frame 1418 includes an enclosure 1456 enclosing driving assembly 1416.

In an exemplary embodiment, in-barrel portion 522, for example, a rod 505, is coupled to driving assembly 1416. In some embodiments, rod 505 is coupled to connector 1448 of rod-end ball joint 1444. In some embodiments, rod 505 is threaded through first bearing 1426 and coupled to connector 1448 of rod-end ball joint 1444. In some embodiments, when connected, at least a portion of rod 505 threaded through first bearing 1426 and connector 1448 form a hub (not shown) along at least a portion of axis (Q).

In some embodiments, linear actuator 1436 axially moves rod-end ball joint 1444 back and forth. In some embodiments, first bearing 1426, partially located inside a bung hole, acts as a ball joint about which rod 505 rotates. In some embodiments, when linear actuator axially moves rod-end ball joint in a first direction, in-barrel portion 522 rod moves in a second, opposite direction. In some embodiments, when linear actuator axially moves rod-end ball joint back and forth, in-barrel portion 522 rod 1605 moves in a pendulous motion.

In some embodiments, in operation driving assembly 1416 rotates in-barrel portion 522 rod 1605. In some embodiments, in operation driving assembly 1416 concurrently rotates and moves rod 1605 pendulously. In some embodiments, driving assembly 1416 moves rod 505 in two planes concurrently. In some embodiments, the in-barrel tip of rod 505 moves along a shape of a star.

In an exemplary embodiment, in-barrel portion 522 rod 1605 is an integral rod. Optionally, rod 1605 is an elastically telescoping rod. Optionally, rod 1605 is a flexible cable. In some embodiments, rod 1605 is a hollow rod. In some embodiments, rod 1605 is curved. In some embodiments, rod 1605 is made of an inert material, for example, stainless steel.

Reference is now made to FIGS. 15A, 15B, 15C and 15D, which are perspective view and cross-section view (W-W) simplified illustrations of an exemplary method of insertion of an in-barrel portion 522 rod 1505 into a wine barrel in accordance with the invention. Optionally and as shown in the exemplary embodiment illustrated in FIGS. 15A-D, rod 1505 is curved.

Figures 15A, 15B, 15C, 15D, 15E:
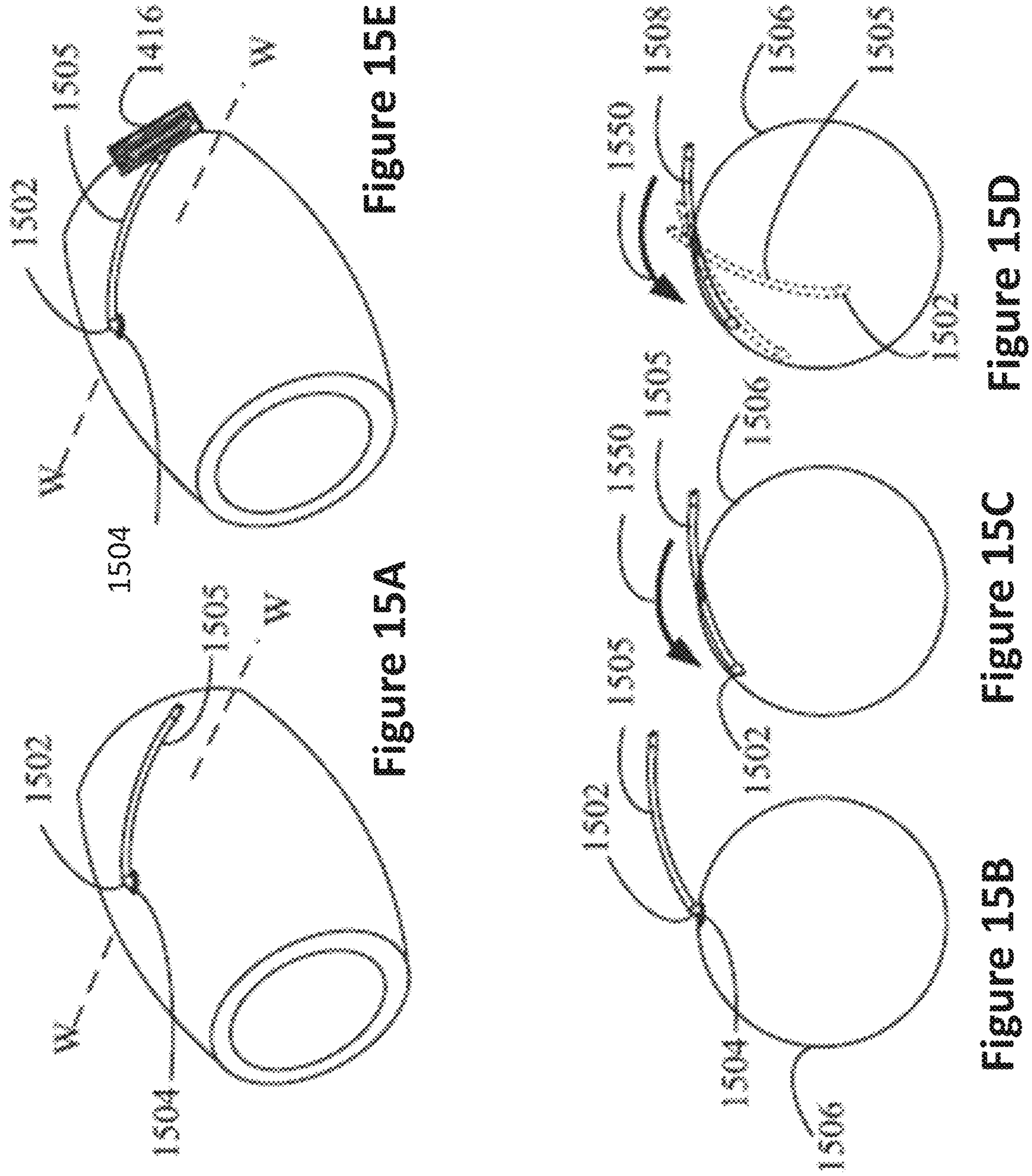
FIGS. 15A, 15B, 15C, 15D and 15E are perspective view and cross-section view (W-W) simplified illustrations of an exemplary method of insertion of an in-barrel portion into a wine barrel in accordance with the invention.

As shown in the exemplary embodiment shown in FIG. 15A, an in-barrel tip 1502 of rod 1505 is positioned over a bung hole 1504 of a wine barrel, rod 1505 oriented substantially horizontally (approximately 0 to 30 degrees from the horizontal). In some embodiments, the curve of rod 1505 generally parallels the curve of the barrel wall 1506. In some embodiments, tip 1502 is inserted into bung hole 1504 in a direction indicated by arrow 1550 and manipulated to follow the internal contour of barrel wall 1506. In some embodiments, rod 1505 is inserted up to a point at which a portion 1508 of rod 1505 remaining outside bung hole 1504 is at a sufficient length to connect to connector 1448 (FIG. 14C) with driving assembly 1416 positioned in place.

In some embodiments, and as shown in FIG. 15E, the coupling of rod 1505 to driving assembly 1416 connector 1448 allows coupled rod 1505 to be angled in a substantially horizontal orientation (approximately 0 to 30 degrees from the horizontal) and be introduced into bung hole 1504 attached to driving assembly 1416 as explained herein.

Exemplary Control Circuitry

In some exemplary embodiments of the invention, system includes control circuitry. Optionally, the control circuitry is packaged with UI 538 (FIG. 5A).

Alternatively, separate circuitry is provided. Optionally, the circuitry is provided with a wireless link to, for example, a central or remote serve.

In some exemplary embodiments of the invention, the circuitry applies various logics and/or protocols, for example, controlling scan parameters, such as one or more of scan shape, scan speed, scrubber speed; controlling filter parameters, such as one or more of speed, dwell time and thresholds for activating inlet and/or outlet buffers; sediment removal parameters, such as one or more of movement, flow rate, stops and changes in flow rate.

In some cases the treatment of a particular barrel may depend on one or more of the type of wine, the history of treatment, measurements from the barrel (e.g., using in-barrel and out of barrel sensors) and input by a user. For example, encrustations may affect different wines differently leading to different requirements in removal thereof, vs. different dangers of over agitation of wine. In another example, the amount and/or ratios and/or sedimentation rates of different type of sedimentation may depend on wine type, age and/or previous treatment, for example, with young wine having more organic debris and/or old wine having more encrustation.

Optionally, UI 538 is used to perform such input and/or display data and/or instructions and/or to allow a user to choose action and/or initiate action. Optionally, the input includes an identification of the barrel and/or wine type (e.g., using a 1D or 2D bar code reader or using RFID or other machine readable method, or by a user entering a human readable code form the barrel). Optionally, a user enters a desired target turbidity and/or other wine processing goal.

In some embodiments of the invention, the circuitry includes logic, for example, rules, tables, expert system, machine learning or and/or other arrangement, which allows the system to recommend an action based on one or more wine or barrel parameters.

In some exemplary embodiments of the invention, after the user enters a barrel ID, the system displays barrel data, past results, recommended treatment parameters (optionally subject to override). After treatment, the system may store sensor readings and/or subjective information, such as taste indication by a taster.

Potential Exemplary System Compactness and/or Other Parameters

Figure 16:
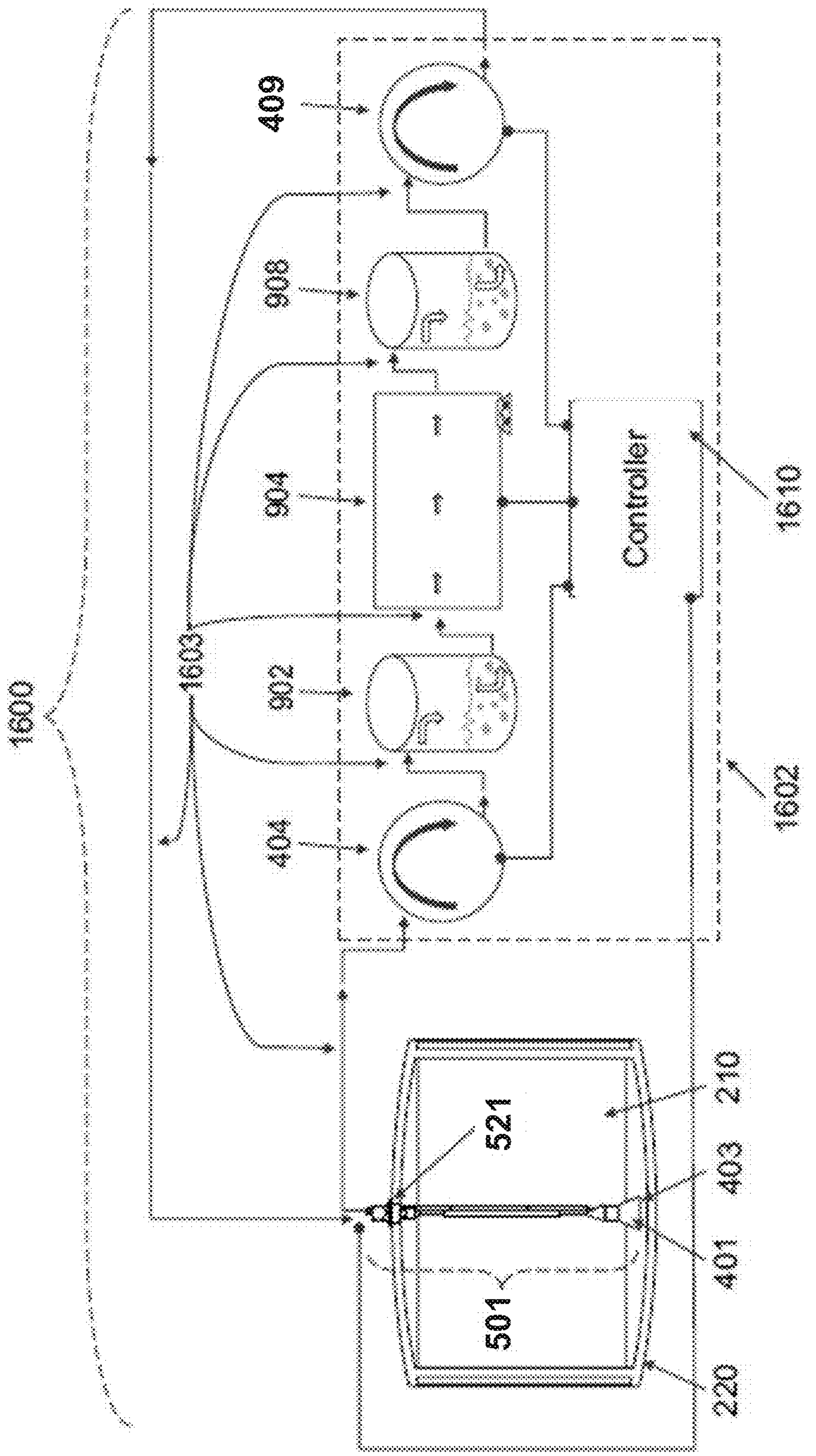
FIG. 16 is a simplified diagram illustration of a system for cleaning wine and/or its containing barrel, according to some embodiments of the invention.

Reference is now also made to FIG. 16, which shows an aging wine barrel cleaning system 1600 for cleaning wine and/or a treating a containing barrel, in accordance with some embodiments of the invention.

In some embodiments, a wine cleaning method 100 cleans wine in a barrel while the barrel contains a volume of the wine comprising most of the wine.

Optionally, the cleaning system 300 reduces mixing of layers during a wine cleaning method 600.

Optionally, barrel treatment methods include treating an interior surface adjacent to an unfilled cavity in the barrel 602 and/or scrubbing and removing encrusted matter from an encrusted interior surface 1300.

Optionally, an inner apparatus 501 of wine cleaning system 300 is installed with a minimum of 20 cm of clearance above the barrel 220.

Optionally, the wine cleaning system 300 contains an extraction pump 404, a filtering system, a return pump 409, and a control unit 1610. Optionally, the filtering system 303 contains an input reservoir, a filter pump, and an output reservoir, interconnecting tubing, and/or a controller 1610.

Optionally, extraction pump 404, return pump 409, and/or filtering system 303 are disposed inside barrel 220. Alternatively, one or more of these are disposed in an outer apparatus 1602, external to the barrel. Optionally, the outer apparatus is transportable on a cart that is moved by one person. Optionally, movement of cart is powered by the person without automotive assistance. Optionally, the outer apparatus 1602 is transportable with only 80 or 60 cm of transverse clearance; for example, between rows of barrels.

Optionally, during a wine cleaning method 100, a maximum of 10%, 20% 30% or intermediate amounts of wine is outside the barrel at any time and/or as part of a complete racking process. Optionally, wine cleaning method 100 cleans multiple layers of wine 210.

Optionally, controller 1610 receives reported data from sensors of a wine cleaning system 300, for example, a turbidity sensor 414 and/or a liquid contact sensor 701.

Optionally, controller 1610 controls system pumps 404, 409; a scrubbing element motor 1206; and/or a swing-drive motor 1403.

Optionally, all controller inputs and outputs are managed by the controller 1610 in a closed-loop system.

Optionally, a turbidity of 10 NTU is achieved within 20, 15 10 or 5 minutes of processing.

Exemplary Wine Barrel Cleaning Robot

An exemplary concept of some embodiments of the wine barrel cleaning system is a system that comprises a robot for cleaning the wine barrel from its sediments. In some embodiments, the robot is small enough to fit in an opening of a wine barrel. In some embodiments, the robot pumps out the sediments while traveling the bottom of the wine barrel. In some embodiments, the robot travels or stops and pumps out sediments according to levels of turbidity sensed by the robot. In some embodiments, while extracting the sediments, some wine is extracted as well. In some embodiments, that wine is cleaned from the sediments and then returned to the wine barrel after it has been treated by filtration, in addition, it may be treated by exposure to UV and/or exposure to inert gases, and measured for turbidity.

Figure 17:
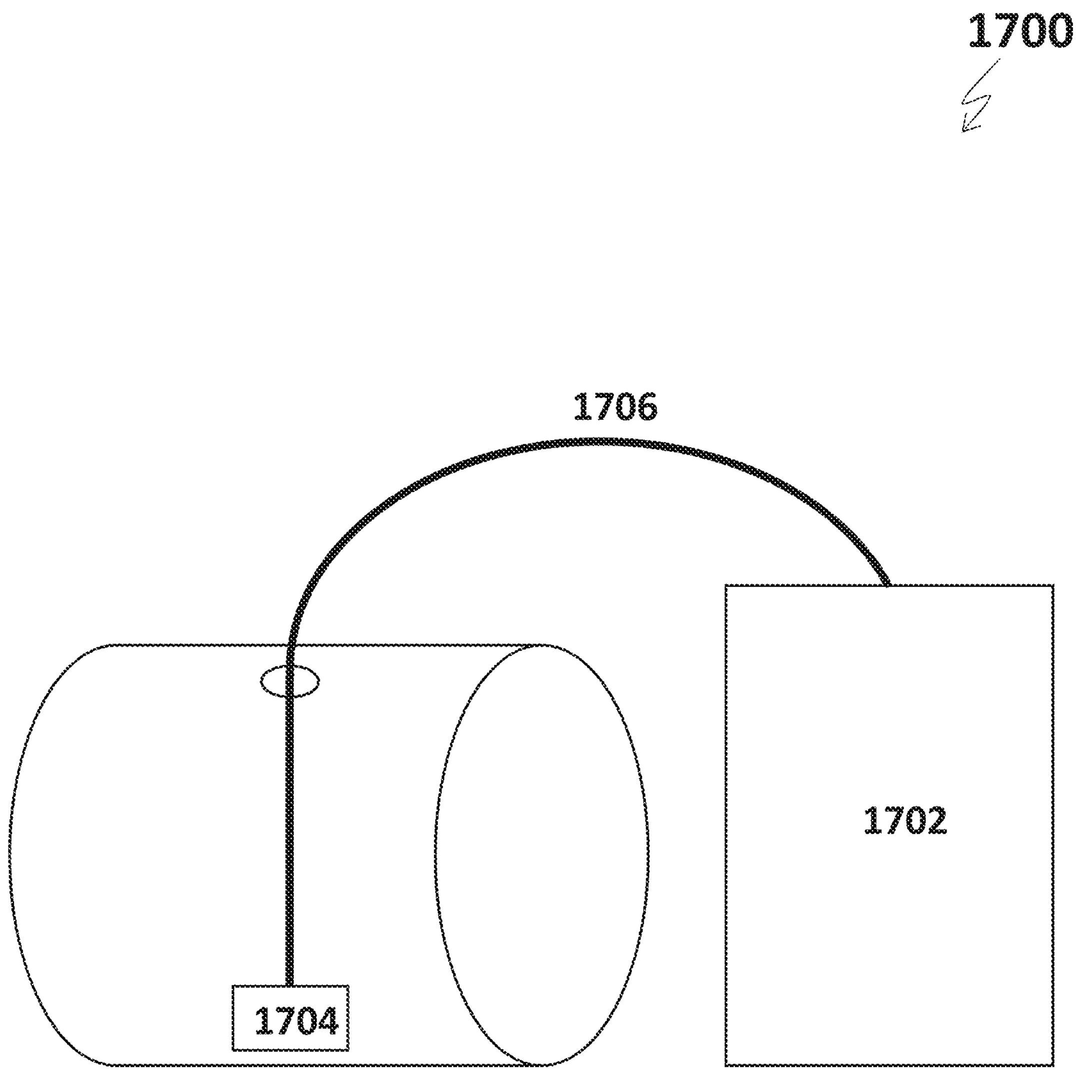
FIG. 17 is a schematic representation of a system for cleaning a wine barrel, according to some embodiments of the invention.

Referring now to FIG. 17 showing a schematic representation of a system for cleaning a wine barrel 1700, according to some embodiments of the invention. In some embodiments, the system 1700 comprises an external unit 1702, an internal unit 1704 and a flexible cable 1706 interconnecting the external unit 1702 and the internal unit 1704 between each other. In some embodiments, the words "external" and "internal" are related to the location where they are actuated in relation to the barrel, for example: external unit refers to a unit that is actuated externally to the barrel, and internal unit refers to a unit that is actuated inside (internally) the barrel. In some embodiments, the internal unit is inserted into the barrel through an opening in the barrel. In some embodiments, the internal unit comprises a robot, which is connected to the external unit through the flexible tube, and the external unit comprises a plurality of subunits, which will be further disclosed below.

Exemplary Mechanism of Action of the System

In some embodiments, the system comprises one or more sensors and a software comprising instructions to clean the wine barrel from its sediment. In some embodiments, this is performed while the wine is in the barrel. In some embodiments, this is performed while maintaining the quality values of the wine as is customary in the wine industry. In some embodiments, the system removes organic and inorganic precipitates (for example, bitartrate salts) accumulating at the bottom of the barrel.

Exemplary Internal Unit

Figure 18A:
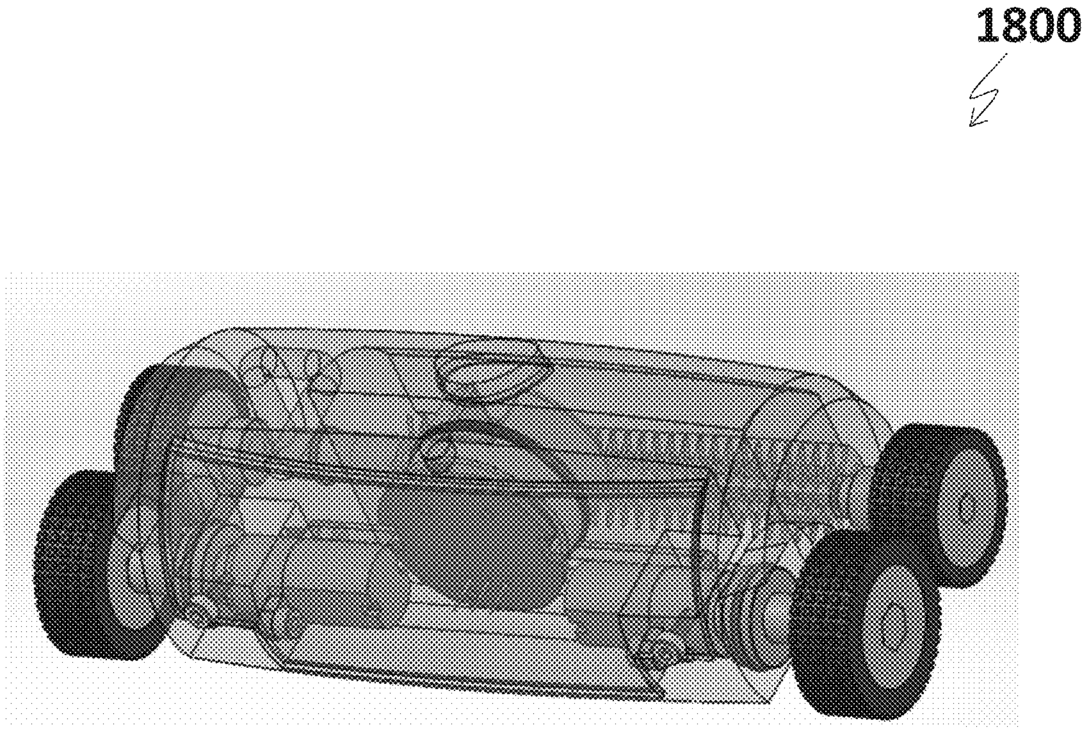
FIGS. 18A-C are a schematic representation (FIG. 18*a*), a picture of a prototype (FIG. 18*b*) and an exploded view of the parts (FIG. 18*c*) of an exemplary internal unit robot, according to some embodiments of the invention.
Figure 18B:
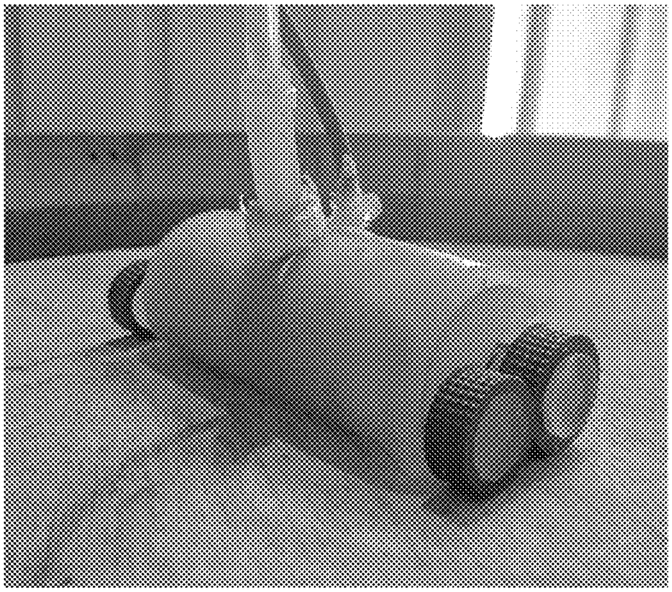
Figure 18C:
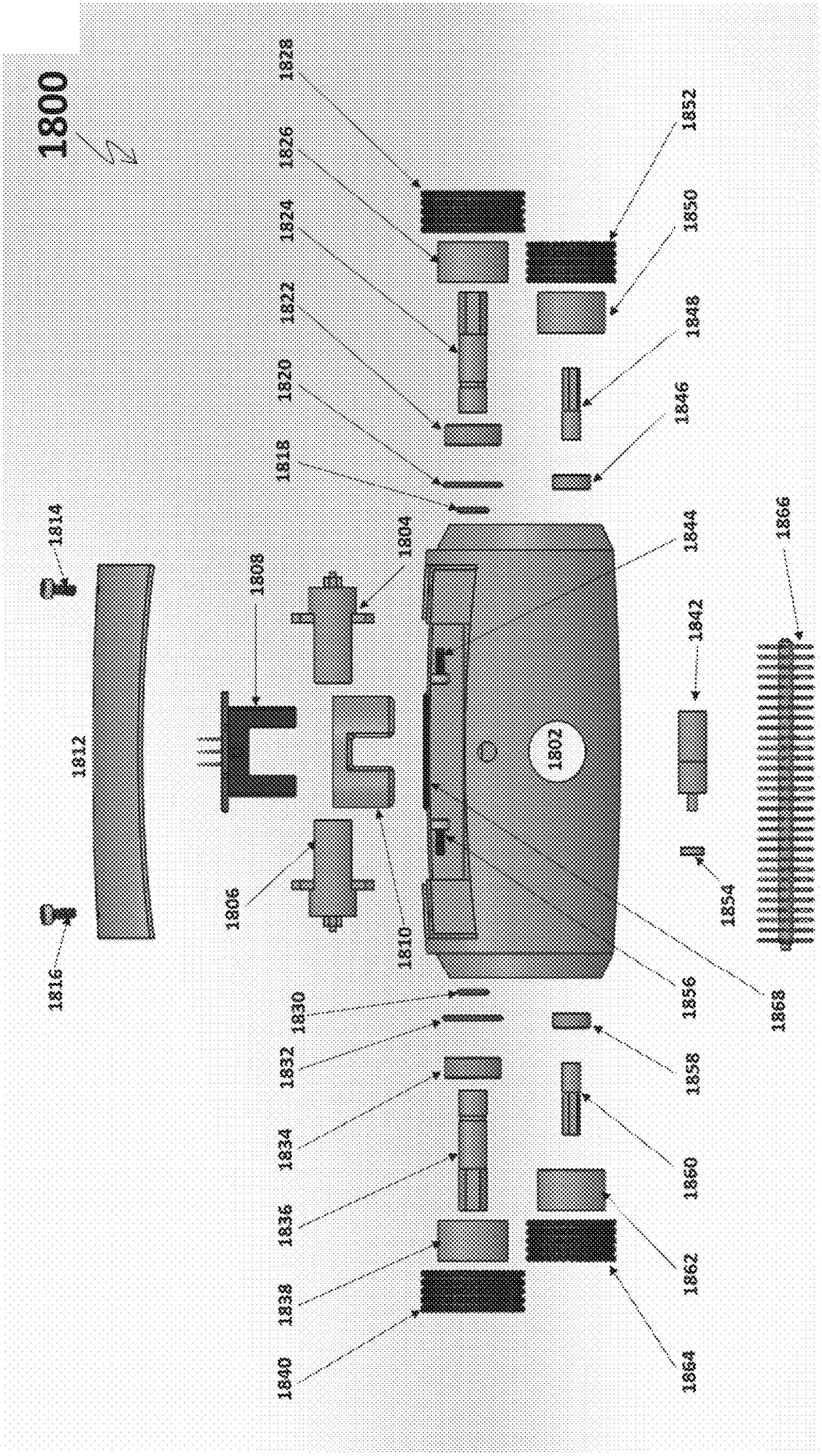

Referring now to FIGS. 18*a-c*, showing a schematic representation (FIG. 18*a*), a picture of a prototype (FIG. 18*b*) and an exploded view of the parts (FIG. 18*c*) of an exemplary internal unit robot 1800, according to some embodiments of the invention.

In some embodiments, the internal unit robot 1800 has a size that fits an opening on the barrel, and once inside the barrel, the robot pumps out sediment while pumping out a relatively small volume of liquid. In some embodiments, the volume of wine is treated outside the barrel, and it is then returned to the barrel once it is significantly clear.

Figure 18D:
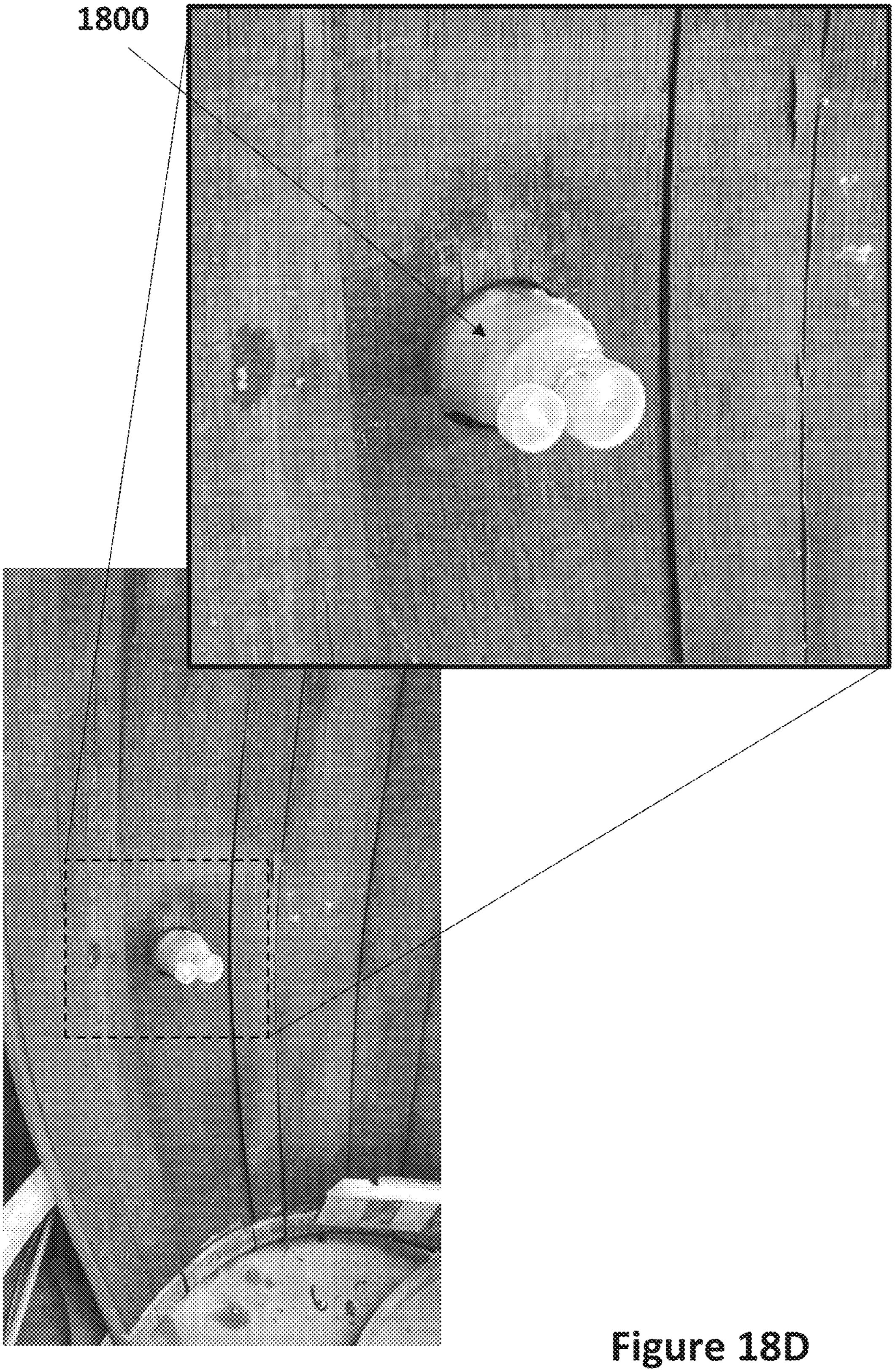
FIG. 18D are images of an exemplary internal unit robot fitted in a hole of a barrel, according to some embodiments of the invention.

In some embodiments, the opening in the barrel is from about 30 mm to about 50 mm, optionally from about 25 mm to about 60 mm, optionally from about 20 mm to about 100 mm, for example, 25 mm, 30 mm, 35 mm, 40 mm or 45 mm. In some embodiments, the internal unit robot is configured in size to fit in the opening of the barrel, as shown for example in FIG. 18*d*, showing a picture of an exemplary prototype of an internal unit robot fitted in a hole of a barrel, according to some embodiments of the invention.

Referring now to FIG. 18*c*, showing an exploded view of the parts of an exemplary internal unit robot, according to some embodiments of the invention.

It should be understood that the following part list is just an exemplary part list and the scope of providing said part list is to allow a person having skills in the art to understand better the invention, therefore the following part list does not intend to limit the invention in any way.

| Part # | Part name |
|---|---|
| 1802 | Robot body |
| 1804 | Motor A |
| 1806 | Motor B |
| 1808 | Turbidity sensor |
| 1810 | Turbidity sensor cover |
| 1812 | Rear cover |
| 1814 | Rear cover socket head cap screw |
| 1816 | Rear cover socket head cap screw |
| 1818 | Right rear wheel O-ring |
| 1820 | Right rear wheel O-ring |
| 1822 | Right rear wheel bearing |
| 1824 | Right rear wheel axle |
| 1826 | Right rear wheel base |
| 1828 | Right rear wheel tire |
| 1830 | Left rear wheel O-ring |
| 1832 | Left rear wheel O-ring |
| 1834 | Left rear wheel bearing |
| 1836 | Left rear wheel axle |
| 1838 | Left rear wheel base |
| 1840 | Left rear wheel tire |
| 1842 | Brush motor |
| 1844 | Motor socket head cap screw |
| 1846 | Right front wheel bearing |
| 1848 | Right front wheel axle |
| 1850 | Right front wheel base |
| 1852 | Right front wheel tire |
| 1854 | Brush bearing |
| 1856 | Motor socket head cap screw |
| 1858 | Left front wheel bearing |
| 1860 | Left front wheel axle |
| 1862 | Left front wheel base |
| 1864 | Left front wheel tire |
| 1866 | Brush |
| 1868 | Turbidity sensor O-ring |

In some embodiments, the wheels of the internal unit robot are made of food grade elastic material, for example rubber, which potentially provide to the robot a higher level of friction that allows movement on slippery precipitation. In some embodiments, the system is configured to control each wheel independently. In some embodiments, this is used to maneuver the robot inside the wine barrel. In some embodiments, different activation of each wheel can be in the velocity they rotate and/or rotation or non-rotation of the wheels and/or forward or backward rotation of the wheels.

In some embodiments, the internal unit robot comprises one or more food grade materials, for example stainless steel, plastic and silicone. In some embodiments, the diameter of the internal unit robot is smaller than 45 mm, for example from about 40 mm to about 44 mm, optionally from about 35 mm to about 44.5 mm. Optionally from about 30 mm to about 44.9 mm. In some embodiments, the length of the internal unit robot is from about 8 cm to about 12 cm. Optionally from about 6 cm to about 14 cm. Optionally from about 4 cm to about 16 cm. For example 8 cm, 9 cm, 10 cm, 11 cm, 12 cm.

In some embodiments, the internal unit robot begins to pump about 200 ml of wine when inserted into the barrel to prevent overflowing of wine due to its own volume.

Exemplary External Unit

Figure 19A:
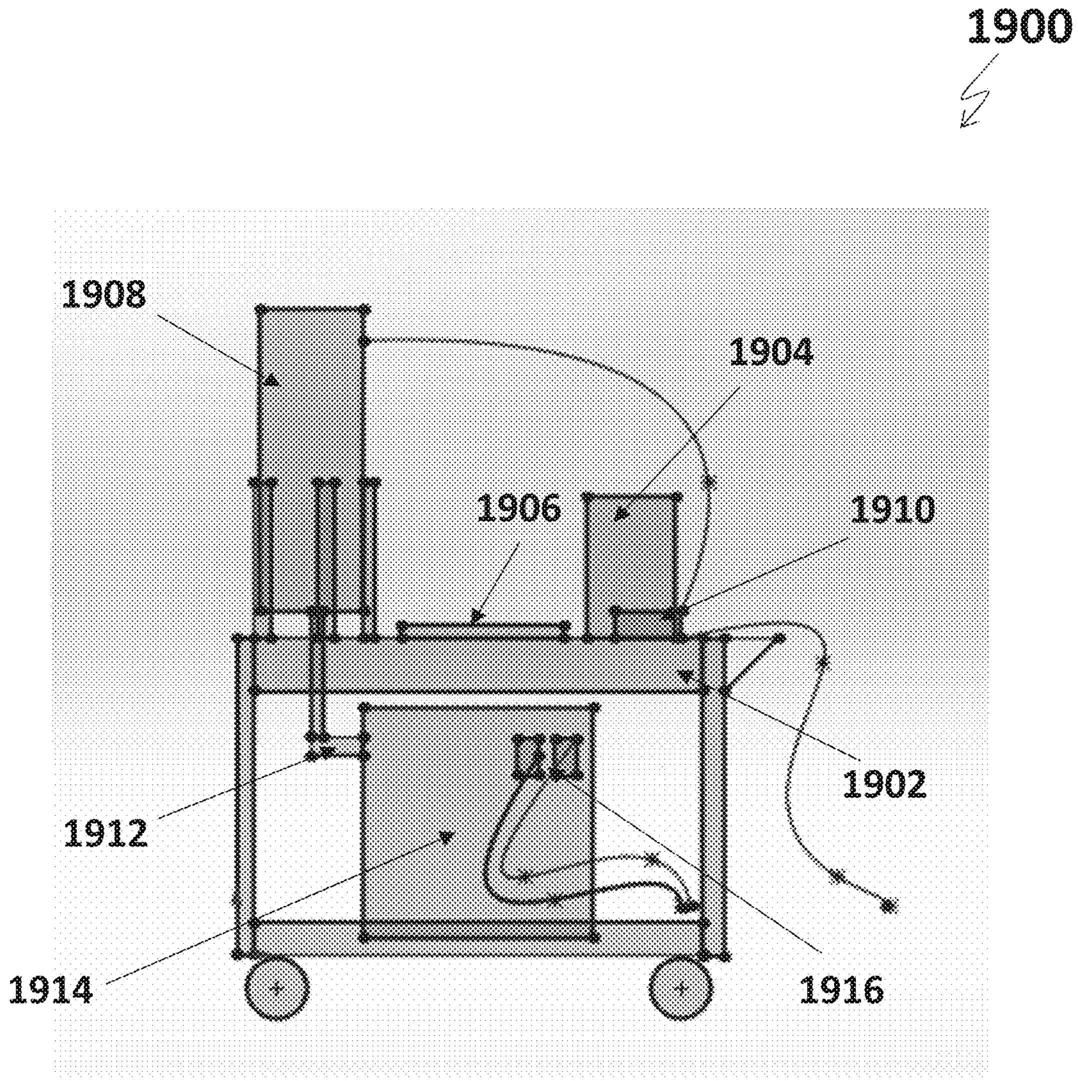
FIGS. 19A-C are a schematic representation (FIG. 19*a*), schematic illustration (FIG. 19*b*) and a picture of an exemplary prototype (FIG. 19*c*) of an exemplary external unit, according to some embodiments of the invention.
Figure 19B:
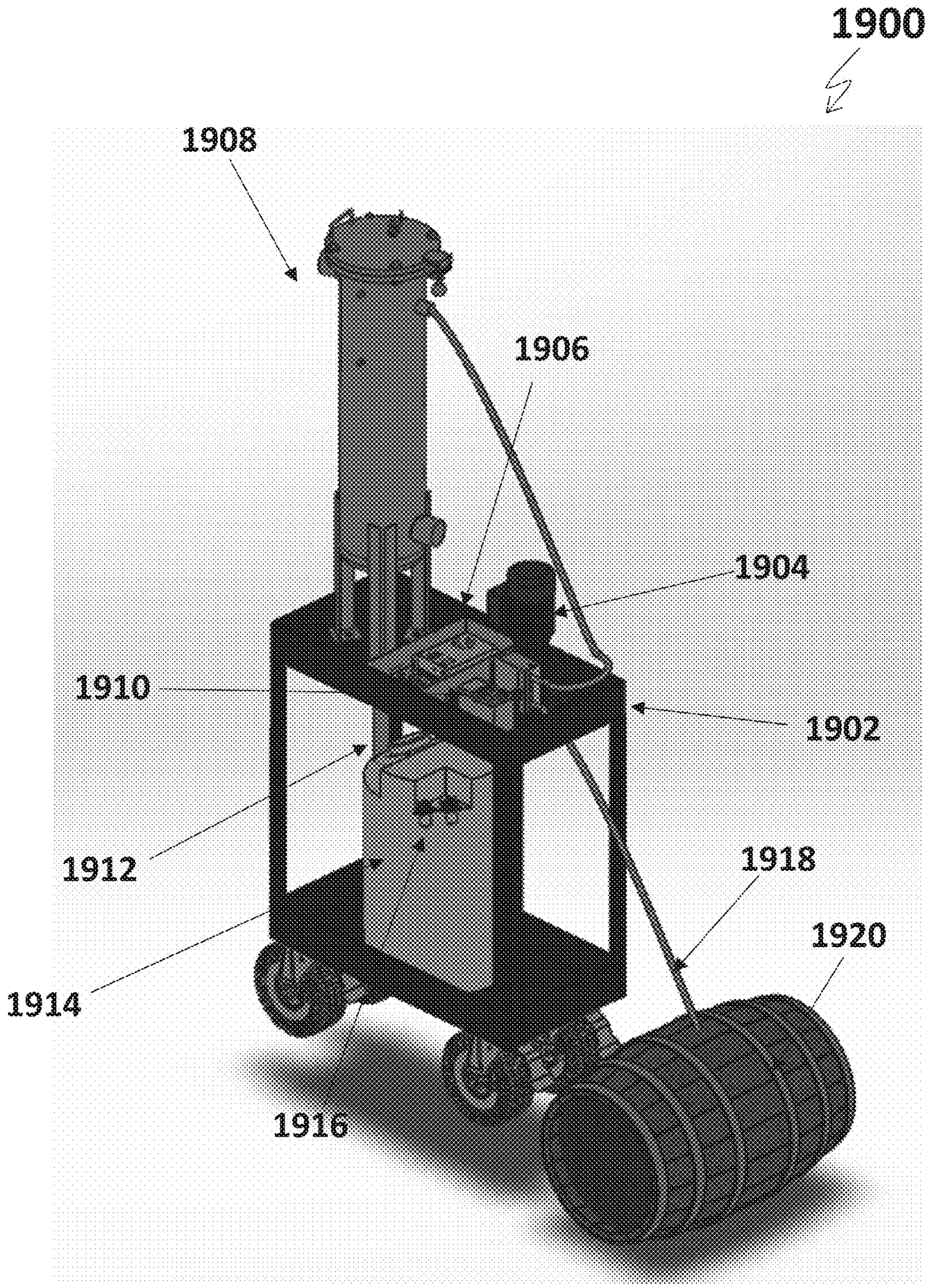
Figure 19C:
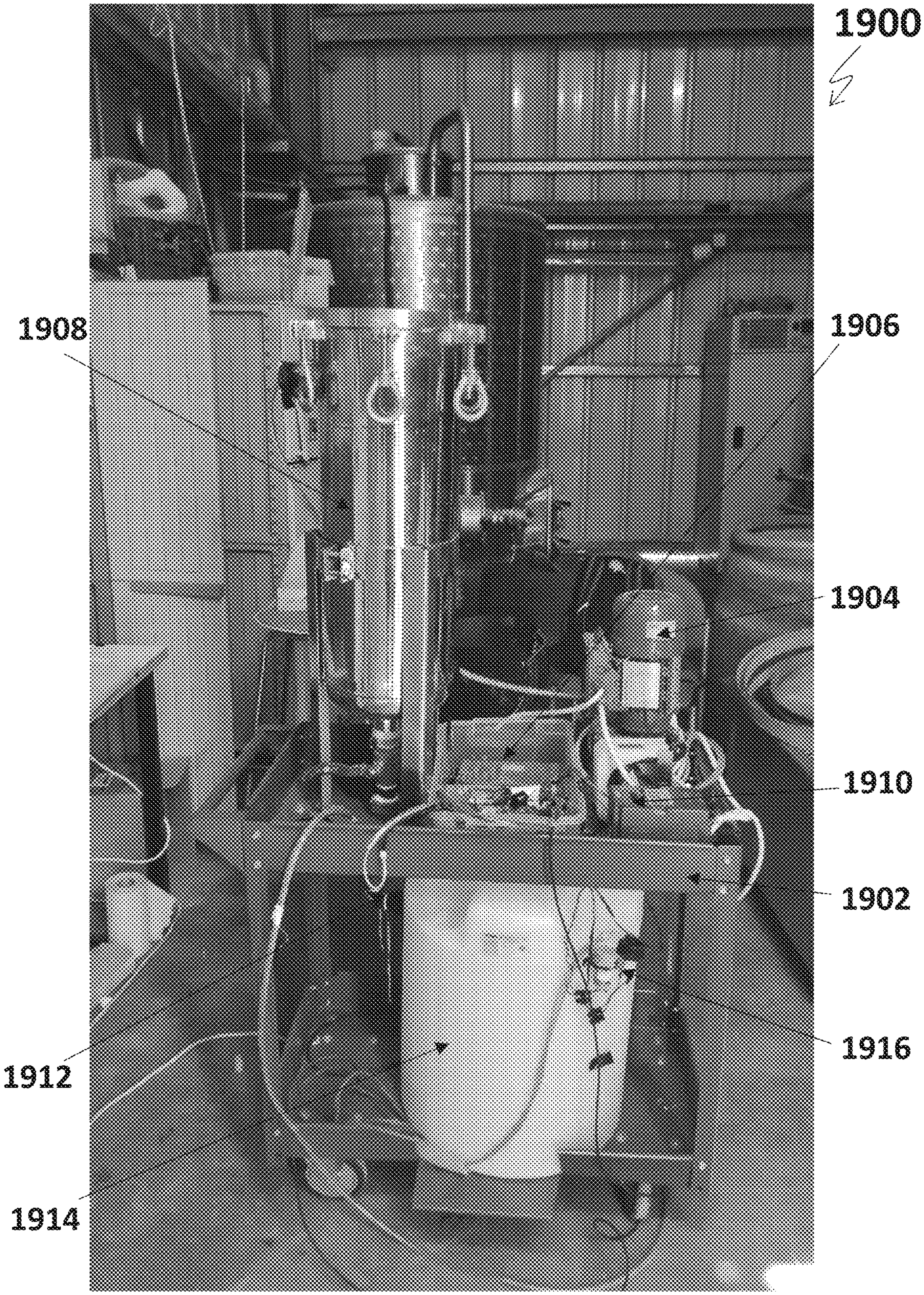

Referring now to FIGS. 19*a-c*, showing a schematic representation (FIG. 19*a*), schematic illustration (FIG. 19*b*) and a picture of an exemplary prototype (FIG. 19*c*) of an exemplary external unit, according to some embodiments of the invention.

In some embodiments, the external unit 1900 comprises one or more of the following parts:

| Part # | Part name |
|---|---|
| 1902 | Cart |
| 1904 | Pump |
| 1906 | Controller |
| 1908 | Filtration subunit |
| 1910 | Velocity controller |
| 1912 | Passage tube |
| 1914 | Collection tank |
| 1916 | Peristaltic pumps |

It should be understood that the following part list is just an exemplary part list and the scope of providing said part list is to allow a person having skills in the art to understand better the invention, therefore the following part list does not intend to limit the invention in any way.

In some embodiments, the external unit 1900 comprises a cart 1902 comprising all the other components of the external unit 1900, for easily moving the external unit 1900 between barrels. In some embodiments, a potential advantage of this is that the cart 1902 potentially allows the easy movement of the system 1700 in the limited space usually encountered in wineries.

In some embodiments, the pump 1904 drives the wine through the internal unit robot 1800 (via the flexible tube 1918) into the filter of the filtration subunit 1908, the filter optionally being a 1-50 microns filter, for example, cartridge filter, centrifugal filter. In some embodiments, the external unit comprises a controller 1906 for controlling the activities of the internal unit robot 1800. In some embodiments, the external unit comprises a collection tank 1914 that receives the wine after filtration, and peristaltic pumps 1916 that return the filtered wine to the barrel 1920.

In some embodiments, the filtration unit comprises a replaceable filter, which can be easily exchanged when necessary. In some embodiments, the filtration unit optionally comprises centrifugal filters, which optionally work under an inert gas atmosphere, such as argon or nitrogen. In some embodiments, a potential advantage of using this filtration systems is that it improves the filtration and reduces the chances to damage the wine during the process.

In some embodiments, flexible tube 1918 comprises both the tube for the extraction of materials from the barrel, and the electrical wiring necessary for the internal unit robot 1800.

Exemplary Flexible Tube

In some embodiments, the flexible tube interconnects between the internal unit and the external unit. In some embodiments, the length of the tube is from about 2 m to about 10 m. In some embodiments, the flexible tube is made of food grade flexible material, for example plastic, rubber and/or silicone. In some embodiments, the role of the flexible tube is to allow the movement of the extracted material from the barrel to the external unit, and to allow access for the necessary electrical cables to the robot. In some embodiments, the flexible tube allows free movement of the robot inside the barrel. In some embodiments, the flexible tube is a telescopic tube, which increases and decreases its length according to what is required by the movements of the internal robot unit.

Exemplary Materials

In some embodiments, the robot and/or the flexible tube are made of materials that are suitable for use in liquids and/or foods.

Exemplary Treatment

In some embodiments, the treatment of the wine does not influence the organoleptic characteristics of the wine. In some embodiments, the treatment improves the organoleptic characteristics of the wine in relation to wine that has not been treated and/or that has been treated with alternative treatment methods. In some embodiments, the treatment does not affect the chemical characteristics of the wine. In some embodiments, the treatment improves the chemical characteristics of the wine in relation to untreated wine and/or that has been treated with alternative treatment methods. In some embodiments, the treatment is filtration. In some embodiments, the treatment is filtration in the presence of an inert gas, optionally at atmospheric pressure. In some embodiments, treatment is exposing the wine to UV. In some embodiments, treatment is a combination of filtration and UV irradiation. In some embodiments, treatment comprises the addition of SO2 into the wine, when necessary. In some embodiments, treatment is a combination of one or more of filtration, UV irradiation and SO2 addition. In some embodiments, treatment comprises successfully removing the sediment while reducing to a minimum the volume of wine removed from the barrel (max 10%), treating the wine in the external unit, comprising an effective separation of the sediment from the wine to prevent depreciation, while maintaining low microbial contamination, and preventing wine oxidation or loss of color.

In some embodiments, treatment of the wine provides one or more of the following: no apparent change in color and/or total phenolics (max 5%); no change in alcohol levels; no change in pH and titratable acidity; no change to volatile acidity; reduction in the turbidity and biological charge, as compared to untreated wine; diminishing reduction aromas (H2S, mercaptans).

Exemplary Controller

In some embodiments, the system 1700 comprises a controller 1906, which comprises a programing (or software) to control all the components of the system 1700. In some embodiments, the software comprises instructions to monitor, optionally in real-time, the actions of the different components of the system 1700, for example, the actions of the pumps, the motors of the internal unit robot and the information received by the sensors. In some embodiments, the software comprises instructions to evaluate the information received by the sensors and direct the robot towards the higher values of turbidity according to a gradient of turbidity, for example, the robot will stop at high turbidity zones and command the initiation of pumping, then upon decrease of the turbidity, will change course towards zones where readings on turbidity are increasing in comparison to previous locations where the robot has been. In some embodiments, the software comprises instructions to record the movements of the robot in order to monitor the movements and ensure that the robot passes through the entire bottom of the barrel.

In some embodiments, the system optionally comprises an electronic device (for example a tablet) where a user can interface with the controller (a graphical interface unit-GUI) and activate and/or monitor and/or troubleshoot the system.

Potential Advantages of the System

In some embodiments, a potential advantage of the system is that it potentially reduces the required manpower needed for the treatment of wine aging in a barrel.

In some embodiments, a potential advantage of the system is that it potentially reduces the effects of treatments to less than 5% effects in the aroma and/or color of the wine.

In some embodiments, a potential advantage of the system is that it saves time due to the fact that the barrels are not needed to be moved and/or emptied in order to be cleaned, since the cleaning is performed while the wine is in the barrel.

In some embodiments, a potential advantage of the system is that it potentially allows the use of technology that do not harm the aging process of the wine.

In some embodiments, a potential advantage of the system is that it potentially reduces the loss of wine by 75% in comparison with known alternative cleaning methods.

In some embodiments, a potential advantage of the system is that it potentially saves tens of thousands of dollars in maintenance, manpower, water and/or mechanization.

Exemplary Additional Elements in the System

In some embodiments, the system optionally comprises a sulfur dioxide (SO2) monitoring element for continuously monitoring and adjusting the SO2 levels in the wine and/or the barrel. In some embodiments, adjusting the SO2 levels is performed by treating the wine by adding SO2 into the wine at the external unit.

In some embodiments, the system comprises a real-time automated monitoring system for continuously monitoring the performance of the system as it performs the cleaning and/or treating of the barrels and/or wine.

Exemplary Method of Cleaning a Wine Barrel

Figure 20:
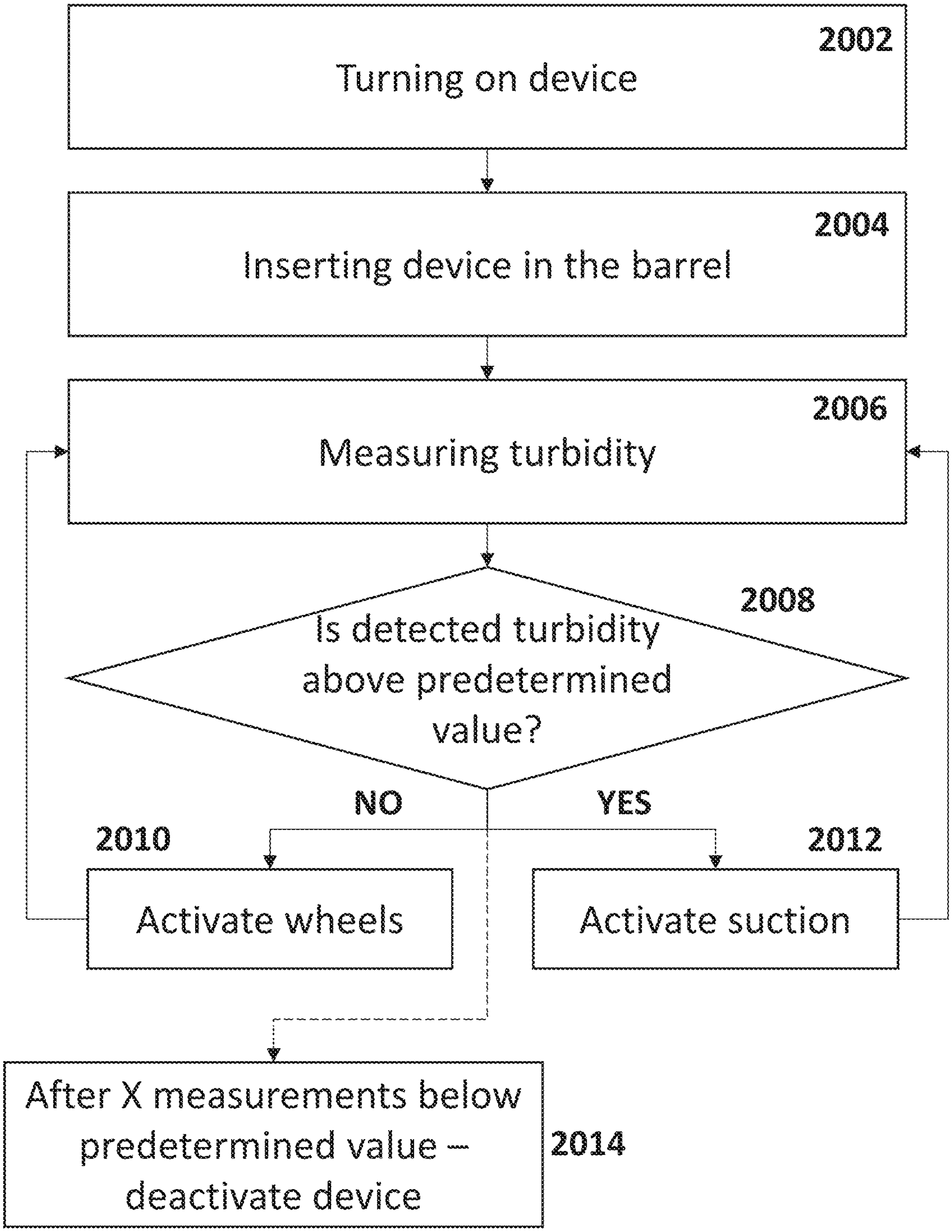
FIG. 20 is a flowchart of an exemplary method of cleaning a barrel, according to some embodiments of the invention.

Referring now to FIG. 20, showing a flowchart of an exemplary method of cleaning a barrel, according to some embodiments of the invention. In some embodiments, the system 1700 performs the following actions during the cleaning process of a wine barrel.

In some embodiments, the user turns on the machine (step 2002). In some embodiments, the robot is inserted in the wine barrel (step 2004). In some embodiments, the robot begins by pumping out about 200 ml of wine to prevent overflowing of the wine due to its own volume. In some embodiments, the robot begins measuring turbidity in the wine (step 2006). In some embodiments, the controller assesses the turbidity data received from the sensor in the robot and checks if it is above a predetermined value (step 2008). In some embodiments, the predetermined value changes according to the type of wine. In some embodiments, when the measured turbidity and/or the scrubbing is below the predetermined value, the system activates the wheels of the robot (step 2010). In some embodiments, measurements of turbidity are constantly performed during the activation of the wheels. In some embodiments, measurements of turbidity are performed a few seconds after the activation of the wheels, for example, after 1 second, after 2 seconds, after 5 seconds. In some embodiments, the robot measures again the turbidity (step 2008). In some embodiments, when the measured turbidity is above a predetermined value, the system activates the suction (step 2012). In some embodiments, measurements of turbidity are constantly performed during the activation of the suction. In some embodiments, measurements of turbidity are performed a few seconds after the activation of the suction, for example, after 1 second, after 2 seconds, after 5 seconds. In some embodiments, once the measured turbidity arrives below the predetermined value, the system activates the wheels (step 2010) so the system can continue to extract the sediments from other locations in the wine barrel. In some embodiments, after a certain numbers of measurements where all are below the predetermined value, the system deactivates the robot (step 2014), since it probably has finished cleaning the barrel. In some embodiments, the certain number of measurements are between 5 and 10, optionally between 4 and 15, optionally between 3 and 20. In some embodiments, optionally, when the sensed turbidity is below a predetermined value, the internal unit robot conducts a scrubbing movement to detach the sediments that are crested, using for example the brush 1866, operated by engine 1842.

In some embodiments, during the activation of the wheels, the system measures the turbidity to assess the difference in turbidity while moving, therefore allowing the measurement of a gradient of turbidity. In some embodiments, according to the gradient of turbidity measured in the wine, the system can maneuver the robot towards the higher levels of turbidity (by the differential activation of the wheels).

Exemplary Experiments on Cleaning Performance of the System

Figure 22A:
FIGS. 22A-B are images of a plastic container used in an exemplary experiment (FIG. 22*a*) and comparative wines before and after treatment (FIG. 22*b*), according to some embodiments of the invention.

The following experiment was performed in order to assess the performance of the system. The experiment aimed to allow the robot to clean the bottom of a 67 cm×35 cm plastic container with a bottom area of 2345 $cm^2$, which is about half the standard surface of a 225 liter barrel, as shown for example in FIG. 22*a*.

Figure 21:
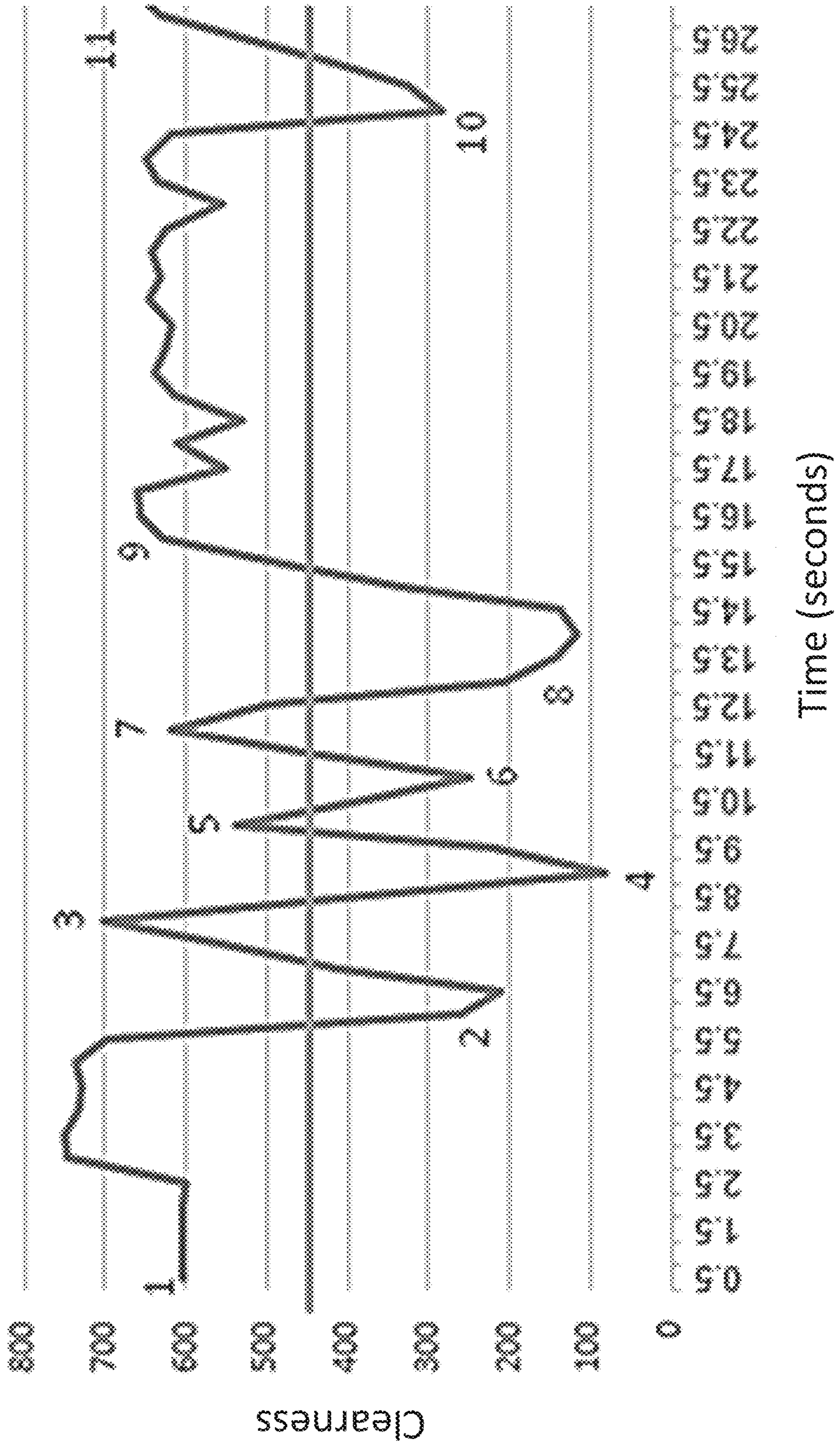
FIG. 21 is a graph of data received by the turbidity sensor of the robot during an exemplary experiment, according to some embodiments of the invention.

Referring now to FIG. 21, showing a graph of the data received by the turbidity sensor of the robot during the experiment. The description of the course of the experiment can be explained through the data received by the sensor in the robot as following:

- At point 1: the device is activated and the robot begins measuring the turbidity. At point 1, during the time the robot is still outside the liquid and the sensor records a level of clarity of 600, then the robot is inserted in the liquid, and the graph shows how from second 4.5, the level of clarity decreases as the robot continues to be submerged in the liquid, as it would normally happen when performed in a wine barrel-clearer liquid at the top and more turbid liquid at the bottom.
- At point 2, the robot has reached the bottom, the propulsion system of the robot is silenced to avoid stirring the sediments, and the suction is activated, therefore the sediments are being pumped out the container. The line in the graph represents the limit line, initiating the suction by the system.
- At point 3, once the level of clarity detected increases to an acceptable number, in this case 700, the robot stops the pumping and begins to move towards the more turbid parts of the container following the turbidity gradient detected by the sensors, which can be seen by the graph dropping from point 3 to point 4.
- At point 4, the robot begins again to pump the sediments while stopping the propulsion of the robot.
- At point 5, once the level of clarity detected increases to an acceptable number, in this case about 550, the robot stops the pumping and begins to move towards the more turbid parts of the container following the turbidity gradient detected by the sensors, which can be seen by the graph dropping from point 5 to point 6.

The robot then continues this cycle of pumping and moving (points 7, 8, 9, 10 and 11), optionally until no more areas of turbidity are found.

It should be reminded that while sediments were pumped out, also some wine was extracted. The extracted wine was filtered and then returned to the container during the experiment, as it would do in a wine barrel.

System efficiency: At the end of the experiment, about 3 liters of liquid were taken out of the container and filtered using the system, and about 200 cc of sediment was removed, which is about 22% of the sediment volume added to the bottom at the beginning of the experiment (900 cc). According to this calculation, the current efficiency of the system can be calculated as follows: for a 225-liter wine barrel containing 1 liter of sediment, it will require the removal of about 15 liters of wine and its treatment in the pumping and filtration system to remove all sediment. This wine volume is equivalent to less than 7% of the wine volume in the barrel.

Figure 22B:

Referring now to FIG. 22*b*, showing on the right side a bottle of liquid before the experiment, and on the left side, a bottle of liquid after the experiment. As it can be seen, the liquid after the experiment is much clearer due to the removal of the sediments.

Figure 23A:
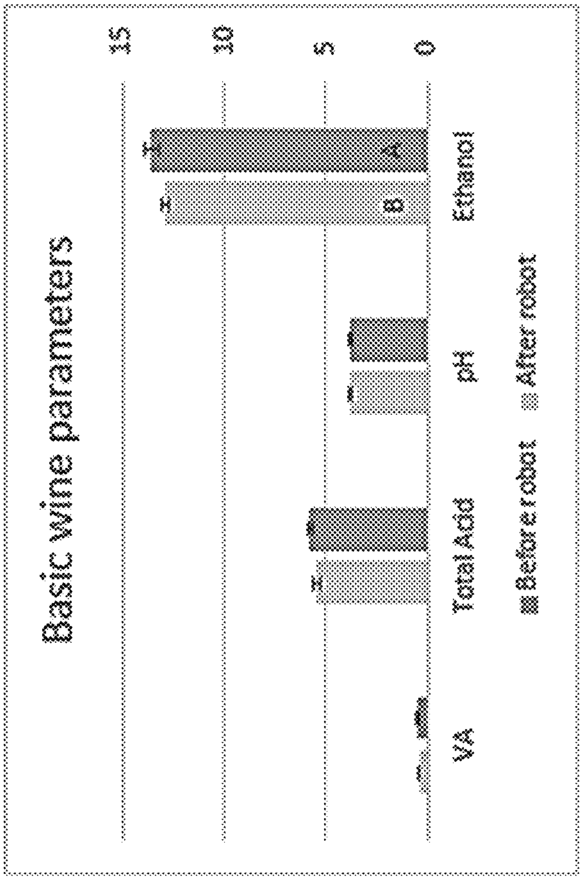
FIGS. 23A-B are graphs showing analysis of the parameters of the wine before and after the passage in the system.
Figure 23B:
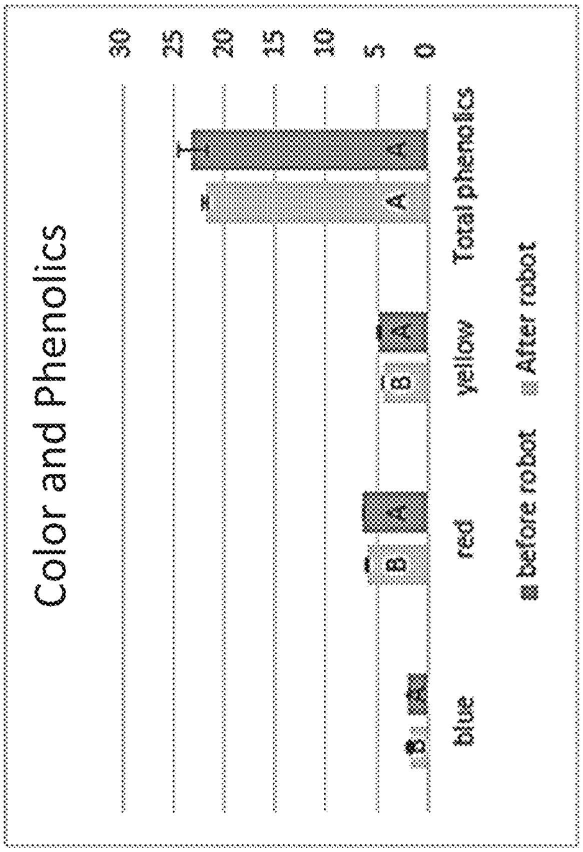

Referring to FIGS. 23*a-b*, showing the analysis of the parameters of the wine before and after the passage in the system. This was performed to evaluate possible damage of the system on the wine during the cleaning process. As can be seen in FIG. 23*a*, the basic wine parameters were almost unaffected by the passage through the system. Similarly, shown in FIG. 23*b*, the color and phenolics of the wine were almost unaffected as well by the passage through the system.

General

It is expected that during the life of a patent maturing from this application, many relevant liquid processing systems and wine cleaning systems will be developed and the scope of the terms "liquid processing system" and "wine cleaning system" is intended to include all such new technologies a priori.

As used herein with reference to quantity or value, the term "about" means "within ±10% of".

The terms "comprises," "comprising," "includes," "including," "having" and their conjugates mean "including but not limited to."

The term "consisting of" means "including and limited to."

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular forms "a", "an" and "the" include plural references unless the context clearly dictates otherwise. For example, the term "a compound" or "at least one compound" may include a plurality of compounds, including mixtures thereof.

Throughout this application, embodiments of this invention may be presented with reference to a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as “from 1 to 6” should be considered to have specifically disclosed subranges such as “from 1 to 3”, “from 1 to 4”, “from 1 to 5”, “from 2 to 4”, “from 2 to 6”, “from 3 to 6”, etc.; as well as individual numbers within that range, for example, 1, 2, 3, 4, 5, and 6. This applies regardless of the breadth of the range.

Whenever a numerical range is indicated herein (for example “10-15”, “10 to 15”, or any pair of numbers linked by these another such range indication), it is meant to include any number (fractional or integral) within the indicated range limits, including the range limits, unless the context clearly dictates otherwise. The phrases “range/ranging/ranges between” a first indicate number and a second indicate number and “range/ranging/ranges from” a first indicate number “to”, “up to”, “until” or “through” (or another such range-indicating term) a second indicate number are used herein interchangeably and are meant to include the first and second indicated numbers and all the fractional and integral numbers therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It is the intent of the applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A barrel cleaning system, comprising (a) an internal unit sized for insertion into an opening in a wine barrel and including an extraction cleaning head assembly and a return feed;

(b) an external unit;

(c) a first tube coupled to said internal unit and leading to said external unit and a second tube leading from said external unit to said return feed; and (d) at least one pump to drive wine in said system;

wherein said internal unit comprises a robot comprising:

i. a robot body;

ii. a plurality of wheels for moving the robot, said wheels characterized by having a rugged surface configured to provide friction that allows movement of said robot on slippery surfaces;

iii. a movement mechanism comprising at least two motors housed within the robot body, wherein for at least two wheels from said plurality of wheels each wheel comprises a motor;

iv. an elongated brush and a brush motor for driving the brush, wherein the brush motor is housed within the robot body;

wherein the robot body comprises a width that is sized for insertion into an opening having a diameter in the range of 20 mm to 100 mm;

wherein said first tube and said second tube are flexible tubes.

2. The barrel cleaning system according to claim 1, wherein said first tube and said second tube are telescopic tubes.

3. The barrel cleaning system according to claim 1, further comprising at least one turbidity sensor.

4. The barrel cleaning system according to claim 3, wherein said at least one turbidity sensor is located in said robot.

5. The barrel cleaning system according to claim 3, wherein said at least one turbidity sensor is located in the first tube.

6. The barrel cleaning system according to claim 3, wherein said at least one turbidity sensor is located in said external unit.

7. The barrel cleaning system according to claim 1, wherein said plurality of wheels are made of elastic material.

8. The barrel cleaning system according to claim 1, wherein said width of said robot body is sized for insertion into an opening having a diameter of about 45 mm.

9. The barrel cleaning system according to claim 1, further comprising circuitry for controlling said at least one pump and said robot.

10. The barrel cleaning system according to claim 9, wherein at least one turbidity sensor delivers turbidity information to said circuitry.

11. The barrel cleaning system according to claim 9, wherein said circuitry comprises instructions to activate said plurality of wheels of said internal unit to move said internal unit towards a second location comprising higher levels of turbidity as sensed by at least one turbidity sensor in comparison with a first location comprising lower levels of turbidity.

12. The barrel cleaning system according to claim 1, wherein said at least two motors are activated by a circuitry.

13. The barrel cleaning system according to claim 1, wherein each motor from said at least two motors is activated independently.

14. The barrel cleaning system according to claim 1, wherein said plurality of wheels are configured to rotate forwards and backwards.

15. The barrel cleaning system according to claim 1, wherein said first tube and said second tube are connected to a top of said internal unit.

16. The barrel cleaning system according to claim 1, wherein said external unit comprises a filtration unit for separating wine from sediments.

17. The barrel cleaning system according to claim 16, wherein said first tube is connected to said filtration unit.

18. The barrel cleaning system according to claim 16, wherein said external unit comprises a collection tank for receiving filtered wine from said filtration unit.

19. The barrel cleaning system according to claim 18, wherein said second tube is connected to said collection tank.

20. The barrel cleaning system according to claim 1, further comprising a cable running from said external unit to said internal unit inside or outside said first tube for providing electrical and electronic needs to said internal unit.

21. The barrel cleaning system according to claim 1, further comprising a SO2 monitoring element.

22. The barrel cleaning system according to claim 1, further comprising a SO2 gas unit for adding SO2 into wine as treatment.

23. The barrel cleaning system according to claim 1, further comprising UV radiation means.

24. The barrel cleaning system according to claim 1, wherein said external unit is configured to treat extracted wine by one or more of filtering by means of a filtration unit, UV radiation by means of a UV radiation means and SO2 addition by means of a SO2 gas unit.

25. A method of cleaning a wine barrel using the barrel cleaning system according to claim 1, the method comprising:

a. inserting the robot in the barrel through an opening in said barrel and allowing said robot to reach a bottom of said barrel;

b. moving said robot, thereby cleaning said barrel by means of said robot.

26. The method according to claim 25, further comprising treating the wine with UV radiation.

27. The method according to claim 25, further comprising activating said at least one pump, thereby extracting materials from said barrel.

28. The method according to claim 27, further comprising filtering said extracted materials to separate wine from said extracted materials.

29. The method according to claim 28, further comprising returning said separated wine to said barrel.

30. The method according to claim 29, further comprising measuring SO2 levels in said separated wine before said returning.

31. The method according to claim 30, further comprising adding SO2 into said separated wine when said measuring provides a value below a predetermined value.

32. The method according to claim 27, further comprising activating a turbidity sensor to sense said extracted materials.

33. The method according to claim 32, further comprising further moving said robot when a sensed level of turbidity of said extracted materials reaches a predetermined level.

34. A method of cleaning a wine barrel using the barrel cleaning system according to claim 1, the method comprising:

a. inserting the robot in the barrel through an opening in said barrel and allowing said robot to reach a bottom of said barrel;

b. activating a turbidity sensor to sense turbidity levels of wine;

when sensed turbidity levels are higher than a predetermined turbidity level value, then:

c. activating said at least one pump, thereby extracting sediments from said bottom of said barrel;

when sensed turbidity levels reach or are lower than said predetermined turbidity level value:

d. moving said robot to another location in said barrel where turbidity levels are higher than said predetermined turbidity level value;

e. repeating (b) through (d) until said bottom of said barrel is absent of said sediments or until said turbidity sensor cannot find another location where turbidity levels are higher than said predetermined turbidity level value.

* * * * *